US009611283B1

(12) United States Patent
Zhang et al.

(10) Patent No.: US 9,611,283 B1
(45) Date of Patent: Apr. 4, 2017

(54) METHODS FOR INHIBITING CELL PROLIFERATION IN ALK-DRIVEN CANCERS

(71) Applicant: ARIAD Pharmaceuticals, Inc., Cambridge, MA (US)

(72) Inventors: Sen Zhang, Newton, MA (US); William C. Shakespeare, Southborough, MA (US); Victor M. Rivera, Arlington, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/249,483

(22) Filed: Apr. 10, 2014

Related U.S. Application Data

(60) Provisional application No. 61/810,554, filed on Apr. 10, 2013.

(51) Int. Cl.
*A61K 31/675* (2006.01)
*A01N 57/00* (2006.01)
*C07F 9/54* (2006.01)

(52) U.S. Cl.
CPC ................. *C07F 9/5442* (2013.01)

(58) Field of Classification Search
CPC .................................... C07F 9/5442
USPC ........................................... 514/86
See application file for complete search history.

(56) References Cited

U.S. PATENT DOCUMENTS

| | | |
|---|---|---|
| 4,966,622 A | 10/1990 | Rempfler et al. |
| 5,521,184 A | 5/1996 | Zimmermann |
| 5,612,340 A | 3/1997 | Zimmermann |
| 6,008,234 A | 12/1999 | Kochanny et al. |
| 6,015,455 A | 1/2000 | Yano et al. |
| 6,030,977 A | 2/2000 | Stock et al. |
| 6,048,390 A | 4/2000 | Yano et al. |
| 6,107,301 A | 8/2000 | Aldrich et al. |
| 6,432,963 B1 | 8/2002 | Hisamichi et al. |
| 6,573,044 B1 | 6/2003 | Gray et al. |
| 6,770,652 B2 | 8/2004 | Gangjee |
| 6,878,697 B2 | 4/2005 | Metcalf et al. |
| 6,949,644 B2 | 9/2005 | Ding et al. |
| 7,151,096 B2 | 12/2006 | Ren et al. |
| 7,169,817 B2 | 1/2007 | Pan et al. |
| 7,176,312 B2 | 2/2007 | Ding et al. |
| 7,189,729 B2 | 3/2007 | Chopiuk et al. |
| 7,253,166 B2 | 8/2007 | Ding et al. |
| 7,256,206 B2 | 8/2007 | Pan et al. |
| 7,338,957 B2 | 3/2008 | Ding et al. |
| 7,371,750 B2 | 5/2008 | Sim et al. |
| 7,423,031 B2 | 9/2008 | Wan et al. |
| 7,423,038 B2 | 9/2008 | Ren et al. |
| 7,449,582 B2 | 11/2008 | Ding et al. |
| 7,514,446 B2 | 4/2009 | Davis-Ward et al. |
| 7,521,457 B2 | 4/2009 | Stadtmueller et al. |
| 7,569,561 B2 | 8/2009 | Stadtmueller et al. |
| 7,569,593 B2 | 8/2009 | Gray et al. |
| 7,589,101 B2 | 9/2009 | Okram et al. |
| 7,605,131 B2 | 10/2009 | Mano et al. |
| 7,642,255 B2 | 1/2010 | Sim et al. |
| 7,671,063 B2 | 3/2010 | Baenteli et al. |
| 7,713,958 B2 | 5/2010 | Wan et al. |
| 7,728,120 B2 | 6/2010 | Mano et al. |
| 7,745,437 B2 | 6/2010 | Ren et al. |
| 7,868,018 B2 | 1/2011 | Xie et al. |
| 7,893,074 B2 | 2/2011 | Garcia-Echeverria et al. |
| 7,939,519 B2 | 5/2011 | Pan et al. |
| 7,943,629 B2 | 5/2011 | Luecking et al. |
| 7,964,592 B2 | 6/2011 | Garcia-Echeverria et al. |
| 7,964,710 B2 | 6/2011 | Mano et al. |
| 7,968,557 B2 | 6/2011 | Choi et al. |
| 8,039,479 B2 | 10/2011 | Michellys et al. |
| 8,071,609 B2 | 12/2011 | Wang et al. |
| 8,101,608 B2 | 1/2012 | Wan et al. |
| 8,197,818 B2 | 6/2012 | Mano et al. |
| 8,383,793 B2 | 2/2013 | Morris et al. |
| 8,450,335 B2 | 5/2013 | Singh et al. |
| 9,012,462 B2 | 4/2015 | Wang et al. |
| 9,273,077 B2 * | 3/2016 | Wang ................. C07F 9/65583 |
| 2003/0171583 A1 | 9/2003 | Ding et al. |
| 2003/0186324 A1 | 10/2003 | Liao et al. |

(Continued)

FOREIGN PATENT DOCUMENTS

CA 2598893 A1 4/2008
EP 0242081 A1 10/1987

(Continued)

OTHER PUBLICATIONS

Zhang et al., "Crizotinib-Resistant Mutants of EML4-ALK Identified Through an Accelerated Mutagenesis Screen", Dec. 2011, Chemical Biology & Drug Design, vol. 78, Issue 6, pp. 999-1005.*
Abbott, "On the Offensive", Nature, 2002, pp. 470-474, vol. 416.
Bennet & Plum (edited by), Cecil Textbook of Medicine, 1996, W.B. Saunders Co., pp. 1004-1010, 20th edition, vol. 1.
Bruning et al., "Role of Brain Insulin Receptor in Control of Body Weight and Reproduction", Science, 2000, pp. 2122-2125, vol. 289.
Carmi et al., "Novel Irreversible Epidermal Growth Factor Receptor Inhibitors by Chemical Modulation of the Cysteine-Trap Portion", J. Med. Chem., 2010, pp. 2038-2050, vol. 53.
Chiarle et al, "The Anaplastic Lymphoma Kinase in the Pathogenesis of Cancer", Nature Reviews, 2008, pp. 11-23, vol. 8.
Cohen, "The Development and Therapeutic Potential of Protein Kinase Inhibitors", Current Opinion in Chemical Biology, 1999, pp. 459-465, vol. 3.
Dalgarno et al., "Structural Basis of Src Tyrosine Kinase Inhibition with a New Class of Potent and Selective Trisubstituted Purine-based Compounds", Chem. Biol. Drug Des., 2006, pp. 46-57, vol. 67.

(Continued)

*Primary Examiner* — My-Chau T Tran
(74) *Attorney, Agent, or Firm* — Proskauer Rose LLP; Fangli Chen

(57) ABSTRACT

The invention features a method for treating patients who have an ALK-driven cancer, which is, or has become, refractory to one or more of crizotinib, CH5424802 and ASP3026, or which bears an ALK mutation identified herein, by administering a compound of formula (I) to the patient. The invention also features methods, kits, and compositions for characterizing ALK-driven cancers to determine whether they express an ALK mutant.

17 Claims, 19 Drawing Sheets

(56) References Cited

U.S. PATENT DOCUMENTS

| | | |
|---|---|---|
| 2003/0191312 A1 | 10/2003 | Ding et al. |
| 2004/0048857 A1 | 3/2004 | Pan et al. |
| 2004/0121316 A1 | 6/2004 | Birkus et al. |
| 2004/0235841 A1 | 11/2004 | Ren et al. |
| 2004/0248952 A1 | 12/2004 | Pan et al. |
| 2005/0014753 A1 | 1/2005 | Ding et al. |
| 2005/0038049 A1 | 2/2005 | Ding et al. |
| 2005/0113398 A1 | 5/2005 | Argade et al. |
| 2005/0124637 A1 | 6/2005 | Cheng et al. |
| 2005/0136396 A1 | 6/2005 | McDermott |
| 2005/0136397 A1 | 6/2005 | McDermott |
| 2005/0136398 A1 | 6/2005 | McDermott |
| 2005/0153955 A1 | 7/2005 | Wan et al. |
| 2005/0159391 A1 | 7/2005 | Ding et al. |
| 2005/0159446 A1 | 7/2005 | Chew et al. |
| 2005/0171105 A1 | 8/2005 | Chopiuk et al. |
| 2005/0187230 A1 | 8/2005 | Ding et al. |
| 2005/0192301 A1 | 9/2005 | Li |
| 2005/0197320 A1 | 9/2005 | Chen et al. |
| 2005/0203114 A1 | 9/2005 | Armistead et al. |
| 2005/0209197 A1 | 9/2005 | Arimilli et al. |
| 2005/0209224 A1 | 9/2005 | Singh et al. |
| 2005/0209285 A1 | 9/2005 | Gray et al. |
| 2005/0222177 A1 | 10/2005 | Sim et al. |
| 2005/0234049 A1 | 10/2005 | Singh et al. |
| 2005/0239054 A1 | 10/2005 | Arimilli et al. |
| 2005/0261295 A1 | 11/2005 | Stadtmueller |
| 2005/0267304 A1 | 12/2005 | Cox et al. |
| 2005/0288327 A1 | 12/2005 | Uesugi et al. |
| 2006/0009642 A1 | 1/2006 | Ding et al. |
| 2006/0035891 A1 | 2/2006 | Li et al. |
| 2006/0079543 A1 | 4/2006 | Sum et al. |
| 2006/0115815 A1 | 6/2006 | Birkus et al. |
| 2006/0128692 A1 | 6/2006 | Chen et al. |
| 2006/0148800 A1 | 7/2006 | Stadtmueller |
| 2006/0167249 A1 | 7/2006 | Argade et al. |
| 2006/0211709 A1 | 9/2006 | Buhr et al. |
| 2006/0229329 A1 | 10/2006 | Heaton et al. |
| 2006/0247241 A1 | 11/2006 | Garcia-Echeverria et al. |
| 2006/0247262 A1 | 11/2006 | Baenteli et al. |
| 2007/0010489 A1 | 1/2007 | Arimilli et al. |
| 2007/0010668 A1 | 1/2007 | Davis-Ward et al. |
| 2007/0032514 A1 | 2/2007 | Zahn et al. |
| 2007/0032637 A1 | 2/2007 | Yokoyama et al. |
| 2007/0066660 A1 | 3/2007 | Stahle et al. |
| 2007/0167439 A1 | 7/2007 | Singh et al. |
| 2007/0179140 A1 | 8/2007 | Argade et al. |
| 2007/0190523 A1 | 8/2007 | Birkus et al. |
| 2007/0191380 A1 | 8/2007 | Ding et al. |
| 2007/0203161 A1 | 8/2007 | Argade et al. |
| 2007/0207999 A1 | 9/2007 | Stadtmueller |
| 2007/0208164 A1 | 9/2007 | Olszewski et al. |
| 2007/0225286 A1 | 9/2007 | Ren et al. |
| 2007/0225495 A1 | 9/2007 | Singh et al. |
| 2007/0259904 A1 | 11/2007 | Noronha et al. |
| 2007/0299060 A1 | 12/2007 | Li et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0051412 A1 | 2/2008 | Argade et al. |
| 2008/0058358 A1 | 3/2008 | Luecking et al. |
| 2008/0090776 A1 | 4/2008 | Mano et al. |
| 2008/0108616 A1 | 5/2008 | Ding et al. |
| 2008/0113986 A1 | 5/2008 | Ren et al. |
| 2008/0132504 A1 | 6/2008 | Garcia-Echeverria et al. |
| 2008/0167330 A1 | 7/2008 | Luecking et al. |
| 2008/0176866 A1 | 7/2008 | Jautelat et al. |
| 2008/0188483 A1 | 8/2008 | Ren et al. |
| 2008/0194605 A1 | 8/2008 | Heinrich et al. |
| 2008/0221098 A1 | 9/2008 | Sim et al. |
| 2008/0221192 A1 | 9/2008 | Wan et al. |
| 2008/0227783 A1 | 9/2008 | Wan et al. |
| 2008/0227786 A1 | 9/2008 | Ferlita et al. |
| 2008/0255112 A1 | 10/2008 | Zhang et al. |
| 2008/0269170 A1 | 10/2008 | Bosch et al. |
| 2008/0280946 A1 | 11/2008 | Nazare et al. |
| 2008/0287432 A1 | 11/2008 | Okram et al. |
| 2008/0300246 A1 | 12/2008 | Xie et al. |
| 2008/0300267 A1 | 12/2008 | Okram et al. |
| 2008/0312438 A1 | 12/2008 | Singh et al. |
| 2009/0036423 A1 | 2/2009 | Pan et al. |
| 2009/0069327 A1 | 3/2009 | Ding et al. |
| 2009/0099193 A1 | 4/2009 | Mano et al. |
| 2009/0105250 A1 | 4/2009 | Sim et al. |
| 2009/0118273 A1 | 5/2009 | Nagle et al. |
| 2009/0137555 A1 | 5/2009 | Wan et al. |
| 2009/0137804 A1 | 5/2009 | Ding et al. |
| 2009/0156596 A1 | 6/2009 | Wang et al. |
| 2009/0181991 A1 | 7/2009 | Zhang et al. |
| 2009/0221555 A1 | 9/2009 | Ahmed et al. |
| 2009/0258910 A1 | 10/2009 | Gray et al. |
| 2009/0286789 A1 | 11/2009 | Hood et al. |
| 2009/0306101 A1 | 12/2009 | Solca et al. |
| 2009/0312321 A1 | 12/2009 | Ren et al. |
| 2009/0318687 A1 | 12/2009 | Singh et al. |
| 2010/0016296 A1 | 1/2010 | Singh et al. |
| 2010/0029610 A1 | 2/2010 | Singh et al. |
| 2010/0081679 A1 | 4/2010 | Greul et al. |
| 2010/0093668 A1 | 4/2010 | Babin et al. |
| 2010/0240673 A1 | 9/2010 | Mano et al. |
| 2010/0249092 A1 | 9/2010 | Singh et al. |
| 2010/0249126 A1 | 9/2010 | Burger et al. |
| 2010/0298156 A1 | 11/2010 | Lee-Hoeflich et al. |
| 2010/0298295 A1 | 11/2010 | Marsilje et al. |
| 2010/0324062 A1 | 12/2010 | Nagle et al. |
| 2011/0021524 A1 | 1/2011 | Adrian et al. |
| 2011/0046108 A1 | 2/2011 | Kettle et al. |
| 2011/0053932 A1 | 3/2011 | Sim et al. |
| 2011/0092491 A1 | 4/2011 | Cheng et al. |
| 2011/0098280 A1 | 4/2011 | Garcia-Echeverria et al. |
| 2011/0105472 A1 | 5/2011 | Greul et al. |
| 2011/0144107 A1 | 6/2011 | Chatterjee et al. |
| 2011/0207736 A1 | 8/2011 | Gray et al. |
| 2011/0212077 A1 | 9/2011 | Noronha et al. |
| 2011/0230478 A1 | 9/2011 | Greul et al. |
| 2011/0230494 A1 | 9/2011 | Singh et al. |
| 2011/0230545 A1 | 9/2011 | Mano et al. |
| 2011/0263541 A1 | 10/2011 | Luo et al. |
| 2011/0288091 A1 | 11/2011 | Gray et al. |
| 2011/0312908 A1 | 12/2011 | Gray et al. |
| 2012/0024620 A1 | 2/2012 | Parodi |
| 2012/0040961 A1 | 2/2012 | Gray et al. |
| 2012/0094999 A1 | 4/2012 | Gray et al. |
| 2012/0108572 A1 | 5/2012 | Wagner et al. |
| 2012/0122902 A1 | 5/2012 | Chen et al. |
| 2012/0252818 A1 | 10/2012 | Chiosis et al. |
| 2013/0158095 A1 | 6/2013 | Mano et al. |
| 2013/0225527 A1 | 8/2013 | Wang et al. |
| 2013/0225528 A1 | 8/2013 | Wang et al. |
| 2014/0024620 A1 | 1/2014 | Dalgarno et al. |
| 2014/0066406 A1 | 3/2014 | Wang et al. |
| 2015/0166591 A1 | 6/2015 | Zhu et al. |
| 2015/0225436 A1 | 8/2015 | Wang et al. |

FOREIGN PATENT DOCUMENTS

| | | |
|---|---|---|
| EP | 0382375 A2 | 8/1990 |
| EP | 0468684 A2 | 1/1992 |
| EP | 0472053 A2 | 2/1992 |
| EP | 0542420 A1 | 5/1993 |
| EP | 0564409 B1 | 10/1993 |
| EP | 0372729 B1 | 1/1995 |
| EP | 0763576 A2 | 3/1997 |
| EP | 1054004 A1 | 11/2000 |
| EP | 1132387 A1 | 9/2001 |
| EP | 2123654 A1 | 11/2009 |
| EP | 2172461 A1 | 4/2010 |
| FR | 2911138 A1 | 7/2008 |
| GB | 1129797 | 10/1968 |
| JP | 11-60573 | 3/1999 |
| WO | WO 95/09847 | 4/1995 |
| WO | WO 96/28427 | 9/1996 |
| WO | WO 97/10887 | 3/1997 |

(56) References Cited

FOREIGN PATENT DOCUMENTS

| | | |
|---|---|---|
| WO | WO 97/19065 | 5/1997 |
| WO | WO 97/20822 | 6/1997 |
| WO | WO 98/11094 | 3/1998 |
| WO | WO 98/15547 | 4/1998 |
| WO | WO 99/03854 | 1/1999 |
| WO | WO 99/63821 | 12/1999 |
| WO | WO 00/15645 | 3/2000 |
| WO | WO 00/27825 | 5/2000 |
| WO | WO 00/31068 | 6/2000 |
| WO | WO 00/33844 | 6/2000 |
| WO | WO 00/46203 | 8/2000 |
| WO | WO 00/67900 | 11/2000 |
| WO | WO 00/78731 | 12/2000 |
| WO | WO 01/09134 | 2/2001 |
| WO | WO 01/47507 | 7/2001 |
| WO | WO 01/64200 | 9/2001 |
| WO | WO 01/64654 | 9/2001 |
| WO | WO 01/64656 | 9/2001 |
| WO | WO 01/72744 | 10/2001 |
| WO | WO 01/85699 | 11/2001 |
| WO | WO 01/85700 | 11/2001 |
| WO | WO 02/00024 | 1/2002 |
| WO | WO 02/04429 | 1/2002 |
| WO | WO 02/22597 | 3/2002 |
| WO | WO 02/46318 | 6/2002 |
| WO | WO 02/059110 | 8/2002 |
| WO | WO 02/083653 | 10/2002 |
| WO | WO 02/102800 | 12/2002 |
| WO | WO 03/000186 | 1/2003 |
| WO | WO 03/030909 | 4/2003 |
| WO | WO 03/037891 | 5/2003 |
| WO | WO 03/057165 | 7/2003 |
| WO | WO 03/066601 | 8/2003 |
| WO | WO 03/078404 | 9/2003 |
| WO | WO 03/094920 | 11/2003 |
| WO | WO 2004/011443 | 2/2004 |
| WO | WO 2004/014382 | 2/2004 |
| WO | WO 2004/018435 | 3/2004 |
| WO | WO 2004/041789 | 5/2004 |
| WO | WO 2004/046118 | 6/2004 |
| WO | WO 2004/074244 | 9/2004 |
| WO | WO 2004/074261 | 9/2004 |
| WO | WO 2004/074262 | 9/2004 |
| WO | WO 2004/080980 | 9/2004 |
| WO | WO 2004/085385 | 10/2004 |
| WO | WO 2004/085409 | 10/2004 |
| WO | WO 2004/096818 | 11/2004 |
| WO | WO 2005/013996 | 2/2005 |
| WO | WO 2005/016528 | 2/2005 |
| WO | WO 2005/016893 | 2/2005 |
| WO | WO 2005/016894 | 2/2005 |
| WO | WO 2005/026130 | 3/2005 |
| WO | WO 2005/026158 | 3/2005 |
| WO | WO 2005/061458 | 7/2005 |
| WO | WO 2005/070890 | 8/2005 |
| WO | WO 2006/021454 | 3/2006 |
| WO | WO 2006/038594 | 4/2006 |
| WO | WO 2006/068826 | 6/2006 |
| WO | WO 2006/074057 | 7/2006 |
| WO | WO 2006/078846 | 7/2006 |
| WO | WO 2006/084015 | 8/2006 |
| WO | WO 2006/101977 | 9/2006 |
| WO | WO 2006/123165 | 11/2006 |
| WO | WO 2006/124874 | 11/2006 |
| WO | WO 2006/128129 | 11/2006 |
| WO | WO 2006/128172 | 11/2006 |
| WO | WO 2006/129100 | 12/2006 |
| WO | WO 2006/133426 | 12/2006 |
| WO | WO 2007/015923 | 2/2007 |
| WO | WO 2007/021937 | 2/2007 |
| WO | WO 2007/042299 | 4/2007 |
| WO | WO 2007/043835 | 4/2007 |
| WO | WO 2007/048064 | 4/2007 |
| WO | WO 2007/053452 | 5/2007 |
| WO | WO 2007/056151 | 5/2007 |
| WO | WO 2007/067506 | 6/2007 |
| WO | WO 2007/071455 | 6/2007 |
| WO | WO 2007/085833 | 8/2007 |
| WO | WO 2007/089768 | 8/2007 |
| WO | WO 2007/113254 | 10/2007 |
| WO | WO 2007/113256 | 10/2007 |
| WO | WO 2007/120339 | 10/2007 |
| WO | WO 2007/125351 | 11/2007 |
| WO | WO 2007/130468 | 11/2007 |
| WO | WO 2008/005538 | 1/2008 |
| WO | WO 2008/009458 | 1/2008 |
| WO | WO 2008/009963 | 1/2008 |
| WO | WO 2008/039359 | 4/2008 |
| WO | WO 2008/045978 | 4/2008 |
| WO | WO 2008/049123 | 4/2008 |
| WO | WO 2008/051493 | 5/2008 |
| WO | WO 2008/057280 | 5/2008 |
| WO | WO 2008/073687 | 6/2008 |
| WO | WO 2008/079719 | 7/2008 |
| WO | WO 2008/079907 | 7/2008 |
| WO | WO 2008/080964 | 7/2008 |
| WO | WO 2008/080965 | 7/2008 |
| WO | WO 2008/092049 | 7/2008 |
| WO | WO 2008/092199 | 8/2008 |
| WO | WO 2008/099073 | 8/2008 |
| WO | WO 2008/115738 | 9/2008 |
| WO | WO 2008/115742 | 9/2008 |
| WO | WO 2008/118822 | 10/2008 |
| WO | WO 2008/121670 | 10/2008 |
| WO | WO 2008/151183 | 12/2008 |
| WO | WO 2009/012421 | 1/2009 |
| WO | WO 2009/020990 | 2/2009 |
| WO | WO 2009/032668 | 3/2009 |
| WO | WO 2009/032694 | 3/2009 |
| WO | WO 2009/032703 | 3/2009 |
| WO | WO 2009/051822 | 4/2009 |
| WO | WO 2009/071535 | 6/2009 |
| WO | WO 2009/080638 | 7/2009 |
| WO | WO 2009/082697 | 7/2009 |
| WO | WO 2009/082701 | 7/2009 |
| WO | WO 2009/087225 | 7/2009 |
| WO | WO 2009/102446 | 8/2009 |
| WO | WO 2009/109605 | 9/2009 |
| WO | WO 2009/112490 | 9/2009 |
| WO | WO 2009/126514 | 10/2009 |
| WO | WO 2009/126515 | 10/2009 |
| WO | WO 2009/127642 | 10/2009 |
| WO | WO 2009/127822 | 10/2009 |
| WO | WO 2009/131687 | 10/2009 |
| WO | WO 2009/143018 | 11/2009 |
| WO | WO 2009/143389 | 11/2009 |
| WO | WO 2009/158571 | 12/2009 |
| WO | WO 2010/008739 | 1/2010 |
| WO | WO 2010/028236 | 3/2010 |
| WO | WO 2010/048149 | 4/2010 |
| WO | WO 2010/051781 | 5/2010 |
| WO | WO 2010/056311 | 5/2010 |
| WO | WO 2010/062571 | 6/2010 |
| WO | WO 2010/068292 | 6/2010 |
| WO | WO 2010/093928 | 8/2010 |
| WO | WO 2010/098866 | 9/2010 |
| WO | WO 2010/106097 | 9/2010 |
| WO | WO 2010/111406 | 9/2010 |
| WO | WO 2010/112210 | 10/2010 |
| WO | WO 2010/123870 | 10/2010 |
| WO | WO 2010/129053 | 11/2010 |
| WO | WO 2010/136559 | 12/2010 |
| WO | WO 2010/142766 | 12/2010 |
| WO | WO 2010/146132 | 12/2010 |
| WO | WO 2011/002807 | 1/2011 |
| WO | WO 2011/002808 | 1/2011 |
| WO | WO 2011/022440 | 2/2011 |
| WO | WO 2011/031896 | 3/2011 |
| WO | WO 2011/034907 | 3/2011 |
| WO | WO 2011/036566 | 3/2011 |
| WO | WO 2011/053518 | 5/2011 |
| WO | WO 2011/079231 | 6/2011 |
| WO | WO 2011/082285 | 7/2011 |
| WO | WO 2011/090760 | 7/2011 |

(56) References Cited

FOREIGN PATENT DOCUMENTS

| WO | WO 2011/103196 | 8/2011 |
|---|---|---|
| WO | WO 2011/140338 | 11/2011 |
| WO | WO 2011/143495 | 11/2011 |
| WO | WO 2011/162515 | 12/2011 |
| WO | WO 2012/021444 | 2/2012 |
| WO | WO 2012/022045 | 2/2012 |
| WO | WO 2012/051587 | 4/2012 |
| WO | WO 2012/061299 | 5/2012 |
| WO | WO 2012/061303 | 5/2012 |
| WO | WO 2012/064706 | 5/2012 |
| WO | WO 2012/151561 | 11/2012 |
| WO | WO 2013/014448 | 1/2013 |
| WO | WO 2013/042006 | 3/2013 |
| WO | WO 2013/169401 | 11/2013 |
| WO | WO 2015/175632 | 11/2015 |
| WO | WO 2015/195228 | 12/2015 |
| WO | WO 2016/065028 A1 | 4/2016 |

OTHER PUBLICATIONS

Database Caplus on STN. Accession No. 1969:28936. Pesticidal Pyrimidinyl Phosphates. Abstract #28936d, Chem Imperial Industries, 1969, p. 324.

Definition of "moiety", 2013, http://goldbook.iupac.org/M03968.html, accessed Sep. 16, 2013.

Demer, "Another Anniversary for the War on Cancer", Bio/Technology, 1994, p. 12, vol. 320.

Doebele et al, "New Strategies to Overcome Limitations of Reversible EGFR Tyrosine Kinase Inhibitor Therapy in Non-Small Cell Lung Cancer", Lung Cancer, 2010, pp. 1-12, vol. 69.

Dubinina et al, "Novel 5,7-disubstituted 6-amino-5H-pyrrolo [3,2-b]pyrazine-2,3-dicarbonitriles, the promising protein kinase inhibitors with antiproliferative activity", European Journal of Medicinal Chemistry, 2006, pp. 727-737, vol. 41.

Eck et al., "Structural and Mechanistic Underpinnings of the . . . of EGFR Mutations in Non-small Cell Lung Cancer", Biochimica et Biophysica Acta, 2010, pp. 559-566.

Fabbro et al., "Protein Kinases as Targets for Anticancer Agents; from Inhibitors to Useful Drugs", Pharmacology & Therapeutics, 2002, pp. 79-98, vol. 93.

Ferrara, "VEGF as a Therapeutic Target in Cancer", Oncology, 2005, pp. 11-16, vol. 69(suppl).

Fletcher, "Approval Heralds New Generation of Kinase Inhibitors?", Nature Biotechnology, 2001, pp. 599-600, vol. 19.

Fresheny, Culture of Animal Cells, A Manual of Basic Techniques, 1983, Alan R. Liss, Inc., New York, p. 4.

Galkin et al., "Indentification of NVP-TAE684, a Potent, Selective, and Efficacious Inhibitor of NPM-ALK", PNAS, 2007, pp. 270-275 & 2024-2025, vol. 104.

Gautschi et al., "Aurora Kinases as Anticancer Drug Targets", Clin. Cancer Res., 2008, pp. 1639-1648, vol. 14(6).

Giurginca et al., "Subsituted Triazines With Phosphonyl Group as Antioxidants for Elastomers and Their Compounds", Polymer Degradation and Stability, 2001, pp. 477-480, vol.

Golub et al., "Molecular Classification of Cancer: Class Discovery and Class Prediction by Gene Expression Monitoring", Science, 1999, pp. 531-537, vol. 286.

Grande et al., "Targeting Oncogenic ALK: A Promising Strategy for Cancer Treatment", Molecular Cancer Therapeutics, 2011, pp. 569-579 + 1529, vol. 10.

Gundla et al., "Discovery of Novel Small-Molecule Inhibitors of Human Epidermal Growth Factor Receptor-2: Combined Ligand and Target-Based Approach", J. Med. Chem., 2008, pp. 3367-3377, vol. 51.

Haluska et al, "In vitro and In vivo Antitumor Effects of the Dual Insulin-Like Growth Factor-I/Insulin Receptor Inhibitor, BMS-554417", Cancer Res, 2006, pp. 362-371, vol. 66.

Jain et al., "Lessons from Phase III Clinical Trials on Anti-VEGF Therapy for Cancer", Nature Clinical Practice Oncology, 2006, pp. 24-40, vol. 3(I).

Katayama et al., "Therapeutic Strategies to Overcome Crizotinib Resistance in Non-Small Cell Lung Cancers Harboring the Fusion Oncogene EML4-ALK", PNAS, 2011, pp. 7535-7540, vol. 108 (18).

Kitamura et al., "Insulin Receptor Knockout Mice", Annu. Rev. Physiol., 2003, pp. 313-332, vol. 65.

Klutchko et al., "Tyrosine Kinase Ihibitors. 19. 6-Alkynamides of 4-Anilinoquinazolines and 4-Anilinopyrido[3,4-d]pyrimidines as Irreversible Inhibitors of the erbB Family of Tyrosine Kinase Receptors", J. Med. Chem., 2006, pp. 1475-1485, vol. 49.

Kulkarni et al., "Tissue-Specific Knockout of the Insulin Receptor in Pancreatic B Cells Creates an Insulin Secretory Defect Similar to that in Type 2 Diabetes", Cell, 1999, pp. 329-339, vol. 96.

Kwak et al., "Irreversible Inhibitors of the EGF Receptor May Circumvent Acquired Resistance to Gefitinib", PNAS, 2005, pp. 7665-7670, vol. 102, No. 21.

Li et al, "Development of Anaplastic Lymphoma Kinase (ALK) Small-Molecule Inhibitors for Cancer Therapy", Med Res Rev, 2008, pp. 372-412, vol. 28(3).

Liao, "Molecular Recognition of Protein Kinase Binding Pockets for Design of Potent and Selective Kinase Inhibitors", Jrnl of Medicinal Chemistry, 2007, pp. 409-424, vol. 50.

Mass, "The HER Receptor Family: A Rich Target for Therapeutic Development", Int. J. Radiation Oncology Biol. Phys., 2004, pp. 932-940, vol. 58(3).

McCormick, "New-age Drug Meets Resistance", Nature, 2001, pp. 281-282, vol. 412.

McDermott et al., "Identification of Genotype-Correlated Sensitivity to Selective Kinase Inhibitors by Using High-throughput Tumor Cell Line Profiling", PNAS, 2007, pp. 19936-19941, vol. 104(50).

McDermott et al., "Genomic Alterations of Anaplastic Lymphoma Kinase May Sensitize Tumors to Anaplastic Lymphoma Kinase Inhibitors", Cancer Research, 2008, pp. 3389-3395, vol. 68(9).

McDermott et al., "Acquired Resistance of Non-small Cell Lung Cancer Cells to MET Kinase Inhibition is Mediated by a Switch to Epidermal Growth Factor Receptor Dependency", Cancer Research, 2010, pp. 1625-1634, vol. 70(4).

Michael et al., "Loss of Insulin Signaling in Hepatocytes Leads to Severe Insulin Resistance and Progressive Hepatic Dysfunction", Molecular Cell, 2000, pp. 87-97, vol. 6.

Michalczyk et al., "Structural Insights Into How Irreversible Inhibitors Can Overcome Drug Resistance in EGFR", Bioorganic & Medicinal Chem, 2008, pp. 3482-3488, vol. 16.

Mishani et al., "High-Affinity Epidermal Growth Factor Receptor (EGFR) Irreversible Inhibitors with Diminished Chemical Reactivities as Positron Emission Tomography (PET)-Imaging Agent Candidates of EGFR Overexpressing Tumors", J. Med. Chem., 2005, pp. 5337-5348, vol. 48.

Mountzios et al., "Aurora Kinases as Targets for Cancer Therapy", Cancer Treatment Reviews, 2008, pp. 175-182, vol. 34.

NCI-NIH, "Targeted Cancer Therapies", (2010), http://www.cancer.gov/cancertopics/factsheet/therapy/targeted, accessed Jan. 12, 2011.

NCI-NIH, "Cancer Prevention Overview", (2012), http://www.cancer.gov/cancertopics/pdq/prevention/overview/patient, accessed Nov. 14, 2012.

Ogiso et al., "Crystal Structure of the Complex of Human Epidermal Growth Factor and Receptor Extracellular Domains", Cell., 2002, pp. 775-787, vol. 110.

Okamoto et al., "Transgenic Rescue of Insulin Receptor-deficient Mice", The Journal of Clinical Investigation, 2004, pp. 214-223, vol. 114.

Palmer et al, "Anaplastic Lymphoma Kinase: Signaling in Development and Disease", Biochem J., 2009, pp. 345-361, vol. 420.

Pao et al., "Rational, Biologically Based Treatment of EGFR-mutant Non-small-cell Lung Cancer", Nature, 2010, pp. 760-774, vol. 10.

Porter et al, "Discovery of 4-azaindoles as novel inhibitors of c-Met kinase", Bioorganic & Medicinal Chemistry Letters, 2009, pp. 2780-2784, vol. 19.

Pyne et al., "Sphingosine Kinase Inhibitors and Cancer: Seeking the Golden Sword of Hercules", Cancer Res, 2011, pp. 6576-6582, vol. 71.

Qiu et al., "Signaling Network of the BTK Family Kinases", Oncogene, 2000, pp. 5651-5661, vol. 19.

(56) References Cited

OTHER PUBLICATIONS

Remon et al., "Beyond EGFR TKI in EGFR-mutant Non-Small Cell Lung Cancer Patients: Main Challenges Still to be Overcome", Cancer Treatment Reviews, 2014, pp. 723-729, vol. 40.
Schindler et al, "Structual Mechanism for STI=571 Inhibition of Abelson Tyrosine Kinase", Science, 2000, pp. 1938-1942, vol. 289.
Simone, "Oncology; Introduction", Cecil Textbook of Medicine, 20th Edition, 1996, pp. 1004-1010, vol. 1.
Smaill et al., "Tyrosine Kinase Inhbitors. 18. 6-Substituted 4-Anilinoquinazolines and 4-Anilinopyrido[3,4-d]pyrimidines as Soluble, Irreversible Inhibitors of the Epidermal Growth Factor Receptor", J. Med. Chem., 2001, pp. 429-440, vol. 44.
Sos et al., "Chemogenomic Profiling Provides Insights into the Limited Activity of Irreversible EGFR Inhibitors in Tumor Cells Expressing the T790M EGFR Resistance Mutation", Cancer Research, 2010, pp. 868-874, vol. 70.
Tartari et al, "Characterization of Some Molecular Mechanisms Governing Autoactivation of the Catalytic Domain of the Anaplastic Lymphoma Kinase", Journal of Biological Chemistry, 2008, pp. 3743-3750, vol. 283(7).
Traxler, "Review: Onocolgic, Endocrine, Metabolic Protein Tyrosine Kinase Inhibitors in Cancer Treatment", Exp.Opin. Ther. Patents, 1997, pp. 571-588, vol. 7(6).
Voskoglou-Nomikos et al, "Clinical Predictive Value of the In Vitro Cell Line, Human Xenograft, and Mouse Allograft Preclinical Cancer Models", Clinical Cancer Research, 2003, pp. 4227-4239, vol. 9.
Wakeling et al., "ZD1839 (Iressa): An Orally Active Inhibitor of Epidermal Growth Factor Signaling with Potential for Cancer Therapy", Cancer Research, 2002, pp. 5749-5754.
Wang et al., "Bone-Targeted 2,6,9-Trisubstituted Purines: Novel Inhibitors of Src Tyrosine Kinase for the Treatment of Bone Diseases", Bioorganic & Medicinal Chemistry Letters, 2003, pp. 3067-3070, vol. 13.
Wissner et al., Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)J. Med. Chem., 2003, pp. 49-63, vol. 46.
Wu et al., "Design and Synthesis of Tetrahydropyridothieno[2,3-d]pyrimidine Scaffold Based Epidermal Growth Factor Receptor (EGFR) Kinase Inhibitors: The Role of Side Chain Chirality and Michael Acceptor Group for Maximal Potency", J. Med. Chem., 2010, pp. 7316-7326, vol. 53.
Yun et al., "The T790M Mutation in EGFR Kinase Causes Drug Resistance by Increasing the Affinity for ATP", PNAS, 2008, pp. 2070-2075, vol. 105, No. 6.
Zhou et al., "Novel Mutant-Selective EGFR Kinase Inhibitors Against EGFR T790M", Nature, 2009, pp. 1070-1074, vol. 462.
Zhou et al., "Cell Culture and Reagents", Nature, Supplemental Information, 2009, pp. 1-39, vol. 462.
Zimmerman et al, "Potent and selective inhibitors of the ABL-kinase: phenylamino-pyrimidine (PAP) derivatives", Biorg. Med. Chem. Letters, 1997, pp. 187-192, vol. 7(2).
Office Action from the European Patent Office for EP Patent Appl. No. 09751617.3, dated Apr. 14, 2014, 7 pages.
Response to Office Action filed in the European Patent Office for EP Patent Appl. No. 09751617.3 dated Aug. 13, 2014, 126 pages.
CN Search Report dated Oct. 14, 2014 for CN Appl. 2012800217027, 2 pages.
EA Search Report dated Jul. 1, 2011 for EA Appl. 201071339, 3 pages.
EA Search Report dated Sep. 4, 2013 for EA Appl. 201390550, 4 pages.
Extended EP Search Report dated May 31, 2005 for EP Appl. 02742236.9, 5 pages.
Extended EP Search Report dated Jul. 10, 2012 for EP Appl. 09832253.0, 6 pages.
Extended EP Search Report dated Aug. 13, 2012 for EP Appl. 09751617.3, 7 pages.
Extended EP Search Report dated Oct. 5, 2012 for EP Appl. 09826414.6, 7 pages.
Extended EP Search Report dated Feb. 27, 2014 for EP Appl. 11833524.9, 9 pages.
Extended EP Search Report dated Oct. 9, 2014 for EP Appl. 12779411.3, 4 pages.
Extended EP Search Report dated Oct. 21, 2015 for EP Appl. 13788352.6, 5 pages.
Int'l Search Report dated Jan. 7, 2003 for PCT/US2002/19631 filed Jun. 21, 2002, 3 pages.
Int'l Search Report & Written Opinion dated Aug. 24, 2009 for PCT/US2009/44918 filed May 21, 2009, 8 pages.
Int'l Search Report & Written Opinion dated Feb. 24, 2010 for PCT/US2009/06520 filed Dec. 11, 2009, 9 pages.
Int'l Search Report & Written Opinion dated Mar. 11, 2010 for PCT/US2009/06057 filed Nov. 12, 2009, 9 pages.
Int'l Search Report & Written Opinion dated Mar. 1, 2012 for PCT/US2011/56457 filed Oct. 14, 2011, 9 pages.
Int'l Search Report & Written Opinion dated Aug. 7, 2012 for PCT/US2012/36683 filed May 4, 2012, 8 pages.
Int'l Search Report & Witten Opinion dated Jun. 12, 2013 for PCT/US2013/032713 filed Mar. 15, 2013, 9 pages.
Int'l Search Report & Written Opinion dated Aug. 7, 2015 for PCT/US2015/30576 filed May 13, 2015, 31 pages.
Int'l Search Report & Written Opinion dated Aug. 14, 2015 for PCT/US2015/30522 filed May 13, 2015, 22 pages.
U.S. Appl. No. 14/995,787, filed Jan. 14, 2016, ARIAD Pharmaceuticals, Inc.
Caira, "Crystalline Polymorphism of Organic Compounds", *Topics in Current Chemistry*, Springer, Berlin, DE, vol. 198; pp. 163-208, 1998.
Godin-Heymann et al., "The T790M "Gatekeeper" Mutation in EGFR Mediates Resistance to Low Concentrations of an Irreversible EGFR Inhibitor", *Mol Cancer Ther*, vol. 7, pp. 874-879, 2008.
Solomon et al., "Current Status of Targeted Therapy for Anaplastlo Lymphoma Kinase-Rearranged Non-Small Cell Lung Cancer", *Clinical Pharmacology & Therapeutics*, vol. 95(1), pp. 15-23, 2013.
Zhou et al., "Discovery of Selective Irreversible Inhibitors for EGFR-T790M", *Bioorganic & Medicinal Chemistry Letters*, vol. 21, pp. 638-843, 2011.
International Search Report & Written Opinion mailed Feb. 11, 2016 for PCT/US2015/056701 (filed Oct. 21, 2015), 15 pages.

\* cited by examiner mRNA Sequence for Human ALK

SEQ ID NO: 1

```
   1 aagcgggggc ggcagcggtg gtagcagctg gtacctcccg ccgcctctgt tcggagggtc
  61 gcggggcacc gaggtgcttt ccggccgccc tctggtcggc cacccaaagc cgcgggcgct
 121 gatgatgggt gaggaggggg cggcaagatt tcgggcgccc ctgccctgaa cgccctcagc
 181 tgctgccgcc ggggccgctc cagtgcctgc gaactctgag gagccgaggc gccggtgaga
 241 gcaaggacgc tgcaaacttg cgcagcgcgg gggctggat tcacgcccag aagttcagca
 301 ggcagacagt ccgaagcctt cccgcagcgg agagatagct tgagggtgcg caagacggca
 361 gcctccgccc tcggttcccg cccagaccgg gcagaagagc ttggaggagc cacaaggaac
 421 gcaaaaggcg gccaggacag cgtgcagcag ctgggagccg ccgttctcag ccttaaaagt
 481 tgcagagatt ggaggctgcc ccgagagggg acagacccca gctccgactg cgggggggcag
 541 gagaggacgg tacccaactg ccacctccct tcaaccatag tagttcctct gtaccgagcg
 601 cagcgagcta cagacggggg cgcggcactc ggcgcggaga gcgggaggct caaggtccca
 661 gccagtgagc ccagtgtgct tgagtgtctc tggactcgcc cctgagcttc caggtctgtt
 721 tcatttagac tcctgctcgc ctccgtgcag ttgggggaaa gcaagagact tgcgcgcacg
 781 cacagtcctc tggagatcag gtggaaggag ccgctgggta ccaaggactg ttcagagcct
 841 cttcccatct cggggagagc gaaggtgag gctgggcccg gagagcagtg taaacggcct
 901 cctccggcgg gatgggagcc atcgggctcc tgtggctgct gccgctgctg cttttccacgg
 961 cagctgtggg ctccgggatg ggaccggcc agcgcgcggg ctccccagct gcggggtcgc
1021 cgctgcagcc ccgggagcca ctcagctact cgcgcctgca gaggaagagt ctggcagttg
1081 acttcgtggt gccctcgctc ttccgtgtct acgcccggga cctactgctg ccaccatcct
1141 cctcggagct gaaggctggc aggcccgagg cccgcggctc gctagctctg gactgcgccc
1201 cgctgctcag gttgctgggg ccggcgccgg gggtctcctg gaccgccggt tcaccagccc
1261 cggcagaggc ccggacgctg tccagggtgc tgaagggcgg ctccgtgcgc aagctccggc
1321 gtgccaagca gttggtgctg gagctgggcg aggaggcgat cttggagggt tgcgtcgggc
1381 cccccgggga ggcggctgtg gggctgctcc agttcaatct cagcgagctg ttcagttggt
1441 ggattcgcca aggcgaaggg cgactgagga tccgcctgat gcccgagaag aaggcgtcgg
1501 aagtgggcag agagggaagg ctgtccgcgg caattcgcgc tcccagccc cgccttctct
1561 tccagatctt cgggactggt catagctcct tggaatcacc aacaaacatg ccatctcctt
1621 ctcctgatta ttttacatgg aatctcacct ggataatgaa agactccttc cctttcctgt
1681 ctcatcgcag ccgatatggt ctggagtgca gctttgactt cccctgtgag ctggagtatt
1741 cccctccact gcatgacctc aggaaccaga gctggtcctg gcgccgcatc ccctccgagg
1801 aggcctccca gatggacttg ctggatgggc tggggcaga gcgttctaag gagatgccca
1861 gaggctcctt tctccttctc aacaccctcag ctgactccaa gcacaccatc ctgagtccgt
1921 ggatgaggag cagcagtgag cactgcacac tggccgtctc ggtgcacagg cacctgcagc
1981 cctctggaag gtacattgcc cagctgctgc cccacaacga ggctgcaaga gagatcctcc
2041 tgatgcccac tccagggaag catggttgga cagtgctcca gggaagaatc gggcgtccag
2101 acaacccatt tcgagtggcc ctggaataca tctccagtgg aaaccgcagc ttgtctgcag
2161 tggacttctt tgccctgaag aactgcagtg aaggaacatc cccaggctcc aagatggccc
2221 tgcagagctc cttcacttgt tggaatggga cagtcctcca gcttgggcag gcctgtgact
2281 tccaccagga ctgtgcccag ggagaagatg agagccagat gtgccgggaaa ctgcctgtgg
2341 gtttttactg caactttgaa gatggcttct gtggctggac ccaaggcaca ctgtcacccc
2401 acactcctca gtggcaggtc aggaccctaa aggatgcccg gttccaggac caccaagacc
2461 atgctctatt gctcagtacc actgatgtcc ccgcttctga aagtgctaca gtgaccagtg
2521 ctacgtttcc tgcaccgatc aagagctctc catgtgagct ccgaatgtcc tggctcattc
2581 gtggagtctt gaggggaaac gtgtccttgg tgctagtgga aacaaaacc gggaaggagc
2641 aaggcaggat ggtctggcat gtcgccgcct atgaagcttg agcctgtgg cagtggatgg
2701 tgttgcctct cctcgatgtg tctgacaggt tctggctgca gatggtcgca tggtggggac
2761 aaggatccag agccatcgtg gcttttgaca atatctccat cagcctggac tgctaccctca
2821 ccattagcgg agaggacaag atcctgcaga atacagcacc caaatcaaga aacctgtttg
2881 agagaaaccc aaacaaggag ctgaaacccg gggaaaattc accaagacag ccccccatct
2941 ttgaccctac agttcattgg ctgttcacca catgtgggggc cagcgggccc catggcccca
```

Figure 8-1

```
3001 cccaggcaca gtgcaacaac gcctaccaga actccaacct gagcgtggag gtggggagcg
3061 agggccccct gaaaggcatc cagatctgga aggtgccagc caccgacacc tacagcatct
3121 cgggctacgg agctgctggc gggaaaggcg ggaagaacac catgatgcgg tcccacggcg
3181 tgtctgtgct gggcatcttc aacctggaga aggatgacat gctgtacatc ctggttgggc
3241 agcagggaga ggacgcctgc cccagtacaa accagttaat ccagaaagtc tgcattggag
3301 agaacaatgt gatagaagaa gaaatccgtg tgaacagaag cgtgcatgag tgggcaggag
3361 gcggaggagg aggggtgga gccacctacg tatttaagat gaaggatgga gtgccggtgc
3421 ccctgatcat tgcagccgga ggtggcggca gggcctacgg ggccaagaca gacacgttcc
3481 acccagagag actggagaat aactcctcgg ttctagggct aaacggcaat tccggagccg
3541 caggtggtgg aggtggctgg aatgataaca cttccttgct ctgggccgga aaatctttgc
3601 aggagggtgc caccggagga cattcctgcc cccaggccat gaagaagtgg gggtgggaga
3661 caagaggggg tttcggaggg ggtggagggg ggtgctcctc aggtggagga ggcggaggat
3721 atataggcgg caatgcagcc tcaaacaatg accccgaaat ggatggggaa gatgggggttt
3781 ccttcatcag tccactgggc atcctgtaca ccccagcttt aaaagtgatg gaaggccacg
3841 gggaagtgaa tattaagcat tatctaaact gcagtcactg tgaggtagac gaatgtcaca
3901 tggaccctga aagccacaag gtcatctgct tctgtgacca cggacggtg ctggctgagg
3961 atggcgtctc ctgcattgtg tcacccaccc cggagccaca cctgccactc tcgctgatcc
4021 tctctgtggt gacctctgcc ctcgtggccg ccctggtcct ggctttctcc ggcatcatga
4081 ttgtgtaccg ccggaagcac caggagctgc aagccatgca gatggagctg cagagccctg
4141 agtacaagct gagcaagctc cgcacctcga ccatcatgac cgactacaac cccaactact
4201 gctttgctgg caagacctcc tccatcagtg acctgaagga ggtgccgcgg aaaaacatca
4261 ccctcattcg gggtctgggc catggcgcct ttggggaggt gtatgaaggc caggtgtccg
4321 gaatgcccaa cgacccaagc cccctgcaag tggctgtgaa gacgctgcct gaagtgtgct
4381 ctgaacagga cgaactggat ttcctcatgg aagccctgat catcagcaaa ttcaaccacc
4441 agaacattgt tcgctgcatt ggggtgagcc tgcaatccct gccccggttc atcctgctgg
4501 agctcatggc ggggggagac ctcaagtcct tcctccgaga gacccgcccct cgcccgagcc
4561 agccctcctc cctggccatg ctggaccttc tgcacgtggc tcgggacatt gcctgtggct
4621 gtcagtattt ggaggaaaac cacttcatcc accgagacat tgctgccaga aactgcctct
4681 tgacctgtcc aggccctgga agagtggcca agattggaga cttcgggatg ccccgagaca
4741 tctacagggc gagctactat agaaaggag gctgtgccat gctgccagtt aagtggatgc
4801 ccccagaggc cttcatggaa ggaatattca cttctaaaac agacacatgg tcctttggag
4861 tgctgctatg ggaaatcttt tctcttggat atatgccata ccccagcaaa agcaaccagg
4921 aagttctgga gtttgtcacc agtggaggcc ggatggaccc acccaagaac tgccctgggc
4981 ctgtataccg gataatgact cagtgctgga acatcagcc tgaagacagg cccaactttg
5041 ccatcatttt ggagaggatt gaatactgca cccagaaccc ggatgtaatc aacaccgctt
5101 tgccgataga atatggtcca cttgtggaag aggaagagaa agtgcctgtg aggcccaagg
5161 accctgaggg ggttcctcct ctcctggtct ctcaacaggc aaaacgggag gaggagcgca
5221 gcccagctgc cccaccacct ctgcctacca cctcctctgg caaggctgca agaaaaccca
5281 cagctgcaga ggtctctgtt cgagtcccta gagggccggc cgtggaaggg ggacacgtga
5341 atatggcatt ctctcagtcc aaccctcctt cggagttgca caaggtccac ggatccagaa
5401 acaagcccac cagcttgtgg aacccaacgt acggctcctg gtttacagag aaacccacca
5461 aaaagaataa tcctatagca aagaaggagc cacacgacag gggtaacctg gggctggagg
5521 gaagctgtac tgtcccacct aacgttgcaa ctgggagact tccggggggcc tcactgctcc
5581 tagagccctc ttcgctgact gccaatatga aggaggtacc tctgttcagg ctacgtcact
5641 tcccttgtgg gaatgtcaat tacggctacc agcaacaggg cttgccctta gaagccgcta
5701 ctgccctgg agctggtcat tacgaggata ccattctgaa aagcaagaat agcatgaacc
5761 agcctggcc ctgagctcgg tcgcacactc acttctcttc cttgggatcc ctaagaccgt
5821 ggaggagga gaggcaatgg ctccttcaca aaccagagac caaatgtcac gttttgtttt
5881 gtgccaacct attttgaagt accaccaaaa aagctgtatt ttgaaaatgc tttagaaagg
5941 ttttgagcat gggttcatcc tattctttcg aaagaagaaa atatcataaa aatgagtgat
6001 aaatacaagg cccagatgtg gttgcataag gttttatgc atgtttgttg tatacttcct
6061 tatgcttctt ttaaattgtg tgtgctctgc ttcaatgtag tcagaattag ctgcttctat
6121 gtttcatagt tggggtcata gatgtttcct tgccttgttg atgtggacat gagccatttg
6181 aggggagagg gaacggaaat aaaggagtta tttgtaatga ctaaaa
```

Figure 8-2

SEQ ID NO: 3

```
   1 agagacttgc gcgcacgcac agtcctctgg agatcaggtg gaaggagccg ctgggtacca
  61 aggactgttc agagcctctt cccatctcgg ggagagcgaa gggtgaggct gggcccggag
 121 agcagtgtaa acggcctcct ccggcgggat gggagccatc gggctcctgt ggctgctgcc
 181 gctgctgctt tccacggcag ctgtgggctc cgggatgggg accggccagc gcgcgggctc
 241 cccagctgcg gggccgccgc tgcagccccg ggagccactc agctactcgc gcctgcagag
 301 gaagagtctg gcagttgact tcgtggtgcc ctcgctcttc cgtgtctacg cccgggacct
 361 actgctgcca ccatcctcct cggagctgaa ggctggcagg cccgagccc gcggctcgct
 421 agctctggac tgcgccccgc tgctcaggtt gctgggccg gcgccggggg tctcctggac
 481 cgccggttca ccagccccgg cagaggcccg gacgctgtcc agggtgctga agggcggctc
 541 cgtgcgcaag ctccggcgtg ccaagcagtt ggtgctggag ctgggcgagg aggcgatctt
 601 ggagggttgc gtcgggcccc cggggaggc ggctgtgggg ctgctccagt tcaatctcag
 661 cgagctgttc agttggtgga ttcgccaagg cgaagggcga ctgaggatcc gcctgatgcc
 721 cgagaagaag gcgtcggaag tgggcagaga gggaaggctg tccgcggcaa ttcgcgcctc
 781 ccagccccgc cttctcttcc agatcttcgg gactggtcat agctccttgg aatcaccaac
 841 aaacatgcct tctccttctc ctgattattt tacatggaat ctcacctgga taatgaaaga
 901 ctccttccct ttcctgtctc atcgcagccg atatggtctg gagtgcagct ttgacttccc
 961 ctgtgagctg gagtattccc ctccactgca tgacctcagg aaccagagct ggtcctggcg
1021 ccgcatcccc tccgaggagg cctccagat ggacttgctg gatgggcctg gggcagagcg
1081 ttctaaggag atgcccagag gctcctttct ccttctcaac acctcagctg actccaagca
1141 caccatcctg agtccgtgga tgaggagcag cagtgagcac tgcacactgg ccgtctcggt
1201 gcacaggcac ctgcagccct ctggaaggta cattgcccag ctgctgcccc acaacgaggc
1261 tgcaagagag atcctcctga tgcccactcc agggaagcat ggttggacag tgctccaggg
1321 aagaatgcga cgtccagaca acccatttcg agtggccctg gaatacatct ccagtggaaa
1381 ccgcagcttg tctgcagtgg acttctttgc cctgaagaac tgcagtgaag gaacatcccc
1441 aggctccaag atggccctgc agagctcctt cacttgttgg aatgggacag tcctccagct
1501 tgggcaggcc tgtgacttcc accaggactg tgcccaggga gaagatgaga gccagatgtg
1561 ccggaaactg cctgtgggtt tttactgcaa ctttgaagat ggcttctgtg gctggaccca
1621 aggcacactg tcaccccaca ctcctcagtg gcaggtcagg accctaaagg atgcccggtt
1681 ccaggaccac caagaccatg ctctattgct cagtaccact gatgtccccg cttctgaaag
1741 tgctacagtg accagtgcta cgtttcctgc accgatcaag agctctccat gtgagctccg
1801 aatgtcctgg ctcattcgtg gagtcttgag gggaaacgtg tccttggtgc tagtggagaa
1861 caaaaccggg aaggagcaag gcaggatggt ctggcatgtc gccgcctatg aaggcttgag
1921 cctgtggcag tggatggtgt tgcctctcct cgatgtgtct gacaggttct ggctgcagat
1981 ggtcgcatgg tggggacaag gatccagagc catcgtggct tttgacaata tctccatcag
2041 cctggactgc tacctcacca ttagcggaca ggacaagatc ctgcagaata cagcacccaa
2101 atcaagaaac ctgtttgaga gaaacccaaa caaggagctg aaaccggggg aaaattcacc
2161 aagacagacc cccatctttg accctacagt tcattggctg ttcaccacat gtgggccag
2221 cgggccccat ggccccaccc aggcacagtg caacaacgcc taccagaact ccaacctgag
2281 cgtggaggtg gggagcgagg gcccccctgaa aggcatccag atctggaagg tgccagccac
2341 cgacacctac agcatctcgg gctacggagc tgctggcggg aaaggcggga agaacaccat
2401 gatgcggtcc cacggcgtgt ctgtgctggg catcttcaac ctggagaagg atgacatgct
2461 gtacatcctg gttgggcagc agggagagga cgcctgcccc agtacaaacc agttaatcca
2521 gaaagtctgc attggagaga acaatgtgat agaagaagaa atccgtgtga acagaagcgt
2581 gcatgagtgg gcaggaggcg gaggaggagg gggtggagcc acctacgtat ttaagatgaa
2641 ggatggagtg ccggtgcccc tgatcattgc agccggaggt ggtggcaggg cctacggggc
2701 caagacagac acgttccacc cagagagact ggagaataac tcctcggttc tagggctaaa
2761 cggcaattcc ggagccgcag gtggtgggga tggctggaat gataacactt ccttgctctg
2821 ggccggaaaa tctttgcagg agggtgccac cggaggacat tcctgccccc aggccatgga
2881 gaagtggggg tgggagacaa gaggggggttt cggaggggt ggaggggggt gctcctcagg
2941 tggaggaggc ggaggatata taggcggcaa tgcagcctca aacaatgacc ccgaaatgga
3001 tgggaagat ggggttttcct tcatcagtcc actgggcatc ctgtacaccc cagctttaaa
3061 agtgatggaa ggccacgggg aagtgaatat taagcattat ctaaactgca gtcactgtga
3121 ggtagacgaa tgtcacatgg accctgaaag ccacaaggtc atctgcttct gtgaccacgg
```

Figure 8-3

```
3181 gacggtgctg gctgaggatg gcgtctcctg cattgtgtca cccaccccgg agccacacct
3241 gccactctcg ctgatcctct ctgtggtgac ctctgccctc gtggccgccc tggtcctggc
3301 tttctccggc atcatgattg tgtaccgccg gaagcaccag gagctgcaag ccatgcagat
3361 ggagctgcag agccctgagt acaagctgag caagctccgc acctcgacca tcatgaccga
3421 ctacaacccc aactactgct ttgctggcaa gacctcctcc atcagtgacc tgaaggaggt
3481 gccgcggaaa aacatcaccc tcattcgggg tctgggccat ggcgcctttg ggaggtgta
3541 tgaaggccag gtgtccggaa tgcccaacga cccaagcccc ctgcaagtgg ctgtgaagac
3601 gctgcctgaa gtgtgctctg aacaggacga actggatttc ctcatggaag ccctgatcat
3661 cagcaaattc aaccaccaga acattgttcg ctgcattggg gtgagcctgc aatccctgcc
3721 ccggttcatc ctgctggagc tcatggcggg ggagacctc aagtccttcc tccgagagac
3781 ccgccctcgc ccgagccagc cctcctccct ggccatgctg gaccttctgc acgtggctcg
3841 ggacattgcc tgtggctgtc agtatttgga ggaaaaccac ttcatccacc gagacattgc
3901 tgccagaaac tgcctcttga cctgtccagg ccctggaaga gtggccaaga ttggagactt
3961 cgggatggcc cgagacatct acaggcgag ctactataga aagggaggct gtgccatgct
4021 gccagttaag tggatgcccc cagaggcctt catggaagga atattcactt ctaaaacaga
4081 cacatggtcc tttggagtgc tgctatggga aatcttttct cttggatata tgccataccc
4141 cagcaaaagc aaccaggaag ttctggagtt tgtcaccagt ggaggccgga tggacccacc
4201 caagaactgc cctgggcctg tataccggat aatgactcag tgctggcaac atcagcctga
4261 agacaggccc aactttgcca tcattttgga gaggattgaa tactgcaccc aggacccgga
4321 tgtaatcaac accgctttgc cgatagaata tggtccactt gtggaagagg aagagaaagt
4381 gcctgtgagg cccaaggacc ctgaggggt tcctcctctc ctggtctctc aacaggcaaa
4441 acgggaggag gagcgcagcc cagctgcccc accacctctg cctaccacct cctctggcaa
4501 ggctgcaaag aaacccacag ctgcagaggt ctctgttcga gtccctagag ggccggccgt
4561 ggaaggggga cacgtgaata tggcattctc tcagtccaac cctccttcgg agttgcacag
4621 ggtccacgga tccagaaata agcccaccag cttgtggaac ccaacgtacg gctcctggtt
4681 tacagagaaa cccaccaaaa agaataatcc tatagcaaag aaggagccac acgagagggg
4741 taacctgggg ctggagggaa gctgtactgt cccacctaac gttgcaactg ggagacttcc
4801 gggggcctca ctgctcctag agccctcttc gctgactgcc aatatgaagg aggtacctct
4861 gttcaggcta cgtcacttcc cttgtgggaa tgtcaattac ggctaccagc aacagggctt
4921 gcccttagaa gccgctactg ccctggagc tggtcattac gaggatacca ttctgaaaag
4981 caagaatagc atgaaccagc ctgggccctg agctcggtcg cacactcact tctcttcctt
5041 gggatcccta agaccgtgga ggagagagag gcaatcaatg gctcctttca caaccagag
5101 accaaatgtc acgttttgtt ttgtgccaac ctattttgaa gtaccaccaa aaaagctgta
5161 ttttgaaaat gctttagaaa ggttttgagc atgggttcat cctattcttt cgaaagaaga
5221 aaatatcata aaaatgagtg ataaatacaa ggccagatgt ggttgcataa ggttttatg
5281 catgtttgtt gta
```

Figure 8-4

Protein Sequence for Human ALK

SEQ ID NO: 2

```
   1 mgaigllwll plllstaavg sgmgtgqrag spaagsplqp replsysrlq rkslavdfvv
  61 pslfrvyard lllppsssel kagrpeargs laldcapllr llgpapgvsw tagspapaea
 121 rtlsrvlkgg svrklrrakq lvlelgeeai legcvgppge aavgllqfnl selfswwirq
 181 gegrlrirlm pekkasevgr egrlsaaira sqprllfqif gtghsslesp tnmpspspdy
 241 ftwnltwimk dsfpflshrs ryglecsfdf pceleysppl hdlrnqswsw rripseeasq
 301 mdlldgpgae rskemprgsf lllntsadsk htilspwmrs ssehctlavs vhrhlqpsgr
 361 yiaqllphne aareillmpt pgkhgwtvlq grigrpdnpf rvaleyissg nrslsavdff
 421 alkncsegts pgskmalqss ftcwngtvlq lgqacdfhqd caqgedesqm crklpvgfyc
 481 nfedgfcgwt qgtlsphtpq wqvrtlkdar fqdhqdhall lsttdvpase satvtsatfp
 541 apiksspcel rmswlirgvl rgnvslvlve nktgkeqgrm vwhvaayegl slwqwmvlpl
 601 ldvsdrfwlq mvawwgqgsr aivafdnisi sldcyltisg edkilqntap ksrnlfernp
 661 nkelkpgens prqtpifdpt vhwlfttcga sgphgptqaq cnnayqnsnl svevgsegpl
 721 kgiqiwkvpa tdtysisgyg aaggkggknt mmrshgvsvl gifnlekddm lyilvgqqge
 781 dacpstnqli qkvcigennv ieeeirvnrs vhewaggggg gggatyvfkm kdgvpvplii
 841 aaggggrayg aktdtfhper lennssvlgl ngnsgaaggg ggwndntsll wagkslqega
 901 tgghscpqam kkwgwetrgg fggggggcss gggggyigg naasnndpem dgedgvsfis
 961 plgilytpal kvmeghgevn ikhylncshc evdechmdpe shkvicfcdh gtvlaedgvs
1021 civsptpeph lplslilsvv tsalvaalvl afsgimivyr rkhqelqamq melqspeykl
1081 sklrtstimt dynpnycfag ktssisdlke vprknitlir glghgafgev yegqvsgmpn
1141 dpsplqvavk tlpevcseqd eldflmeali iskfnhqniv rcigvslqsl prfillelma
1201 ggdlksflre trprpsqpss lamldllhva rdiacgcqyl eenhfihrdi aarnclltcp
1261 gpgrvakigd fgmardiyra syyrkggcam lpvkwmppea fmegiftskt dtwsfgvllw
1321 eifslgympy psksnqevle fvtsggrmdp pkncpgpvyr imtqcwqhqp edrpnfaiil
1381 erieyctqdp dvintalpie ygplveeeek vpvrpkdpeg vppllvsqqa kreeerspaa
1441 ppplpttssg kaakkptaae vsvrvprgpa vegghvnmaf sqsnppselh kvhgsrnkpt
1501 slwnptygsw ftekptkknn piakkephdr gnlglegsct vppnvatgrl pgasllleps
1561 sltanmkevp lfrlrhfpcg nvnygyqqg pleaatapg aghyedtilk sknsmnqpgp
```

SEQ ID NO: 4

```
   1 mgaigllwll plllstaavg sgmgtgqrag spaagpplqp replsysrlq rkslavdfvv
  61 pslfrvyard lllppsssel kagrpeargs laldcapllr llgpapgvsw tagspapaea
 121 rtlsrvlkgg svrklrrakq lvlelgeeai legcvgppge aavgllqfnl selfswwirq
 181 gegrlrirlm pekkasevgr egrlsaaira sqprllfqif gtghsslesp tnmpspspdy
 241 ftwnltwimk dsfpflshrs ryglecsfdf pceleysppl hdlrnqswsw rripseeasq
 301 mdlldgpgae rskemprgsf lllntsadsk htilspwmrs ssehctlavs vhrhlqpsgr
 361 yiaqllphne aareillmpt pgkhgwtvlq grigrpdnpf rvaleyissg nrslsavdff
 421 alkncsegts pgskmalqss ftcwngtvlq lgqacdfhqd caqgedesqm crklpvgfyc
 481 nfedgfcgwt qgtlsphtpq wqvrtlkdar fqdhqdhall lsttdvpase satvtsatfp
 541 apiksspcel rmswlirgvl rgnvslvlve nktgkeqgrm vwhvaayegl slwqwmvlpl
 601 ldvsdrfwlq mvawwgqgsr aivafdnisi sldcyltisg edkilqntap ksrnlfernp
 661 nkelkpgens prqtpifdpt vhwlfttcga sgphgptqaq cnnayqnsnl svevgsegpl
 721 kgiqiwkvpa tdtysisgyg aaggkggknt mmrshgvsvl gifnlekddm lyilvgqqge
 781 dacpstnqli qkvcigennv ieeeirvnrs vhewaggggg gggatyvfkm kdgvpvplii
 841 aaggggrayg aktdtfhper lennssvlgl ngnsgaaggg ggwndntsll wagkslqega
 901 tgghscpqam kkwgwetrgg fggggggcss gggggyigg naasnndpem dgedgvsfis
```

Figure 9-1

```
 961 plgilytpal kvmeghgevn ikhylncshc evdechmdpe shkvicfcdh gtvlaedgvs
1021 civsptpeph lplslilsvv tsalvaalvl afsgimivyr rkhqelqamq melqspeykl
1081 sklrtstimt dynpnycfag ktssisdlke vprknitlir glghgafgev yegqvsgmpn
1141 dpsplqvavk tlpevcseqd eldflmeali iskfnhqniv rcigvslqsl prfillelma
1201 ggdlksflre trprpsqpss lamldllhva rdiacgcqyl eenhfihrdi aarnclltcp
1261 gpgrvakigd fgmardiyra syyrkggcam lpvkwmppea fmegiftskt dtwsfgvllw
1321 eifslgympy psksnqevle fvtsggrmdp pkncpgpvyr imtqcwqhqp edrpnfaiil
1381 erieyctqdp dvintalpie ygplveeeek vpvrpkdpeg vppllvsqqa kreeerspaa
1441 ppplpttssg kaakkptaae isvrvprgpa vegghvnmaf sqsnppselh kvhgsrnkpt
1501 slwnptygsw ftekptkknn piakkephdr gnlglegsct vppnvatgrl pgaslllleps
1561 sltanmkevp lfrlrhfpcg nvnygyqqqg lpleaatapg aghyedtilk sknsmnqpgp
```

Figure 9-2

NPM/ALK Fusion mRNA
SEQ ID NO: 5

```
   1 atggaagatt cgatggacat ggacatgagc cccctgaggc cccagaacta tctttcggt
  61 tgtgaactaa aggccgacaa agattatcac tttaaggtgg ataatgatga aaatgagcac
 121 cagttatctt taagaacggt cagtttaggg gctggtgcaa aggatgagtt gcacattgtt
 181 gaagcagagg caatgaatta cgaaggcagt ccaattaaag taacactggc aactttgaaa
 241 atgtctgtac agccaacggt ttcccttggg ggctttgaaa taacaccacc agtggtctta
 301 aggttgaagt gtggtcagg gccagtgcat attagtggac agcacttagt agtgtaccgc
 361 cggaagcacc aggagctgca agccatgcag atggagctgc agagccctga gtacaagctg
 421 agcaagctcc gcacctcgac catcatgacc gactacaacc ccaactactg ctttgctggc
 481 aagacctcct ccatcagtga cctgaaggag gtgccgcgga aaaacatcac cctcattcgg
 541 ggtctggcc atggcgcctt tggggaggtg tatgaaggcc aggtgtccgg aatgcccaac
 601 gacccaagcc cctgcaagt ggctgtgaag acgctgcctg aagtgtgctc tgaacaggac
 661 gaactggatt tcctcatgga agccctgatc atcagcaaat tcaaccacca gaacattgtt
 721 cgctgcattg gggtgagcct gcaatccctg cccggttca tcctgctgga gctcatggcg
 781 gggggagacc tcaagtcctt cctccgagag acccgcctc gccgagcca gccctcctcc
 841 ctggccatgc tggaccttct gcacgtggct cgggacattg cctgtggctg tcagtatttg
 901 gaggaaaacc acttcatcca ccgagacatt gctgccagaa actgcctctt gacctgtcca
 961 ggccctggaa gagtggccaa gattggagac ttcgggatgg cccgagacat ctacagggcg
1021 agctactata gaaagggagg ctgtgccatg ctgccagtta agtggatgcc cccagaggcc
1081 ttcatggaag gaatattcac ttctaaaaca gacacatggt cctttggagt gctgctatgg
1141 gaaatctttt ctcttggata tatgccatac cccagcaaaa gcaaccagga agttctggag
1201 tttgtcacca gtggaggccg gatggaccca cccaagaact gccctgggcc tgtataccgg
1261 ataatgactc agtgctggca acatcagcct gaagacaggc ccaactttgc catcattttg
1321 gagaggattg aatactgcac ccaggacccg gatgtaatca caccgctttg ccgatagaa
1381 tatggtccac ttgtgaaga ggaagagaaa gtgcctgtga ggcccaagga ccctgagggg
1441 gttcctcctc tcctggtctc tcaacaggca aaacgggagg aggagcgcag cccagctgcc
1501 ccaccacctc tgcctaccac ctcctctggc aaggctgcaa agaaacccac agctgcagag
1561 gtctctgttc gagtccctag agggccggcc gtggaagggg gacacgtgaa tatggcattc
1621 tctcagtcca accctccttc ggagttgcac aaggtccacg gatccagaaa caagcccacc
1681 agcttgtgga acccaacgta cggctcctgg tttacagaga aacccaccaa aagaataat
1741 cctatagcaa agaaggagcc cacgacagg ggtaacctgg ggctggaggg aagctgtact
1801 gtcccaccta acgttgcaac tgggagactt ccgggggcct cactgctcct agagccctct
1861 tcgctgactg ccaatatgaa ggaggtacct ctgttcaggc tacgtcactt cccttgtggg
1921 aatgtcaatt acggctacca gcaacagggc ttgcccttag aagccgctac tgccctgga
1981 gctggtcatt acgaggatac cattctgaaa agcaagaata gcatgaacca gcctgggccc
2041 tga
```

NPM/ALK Fusion Protein
SEQ ID NO: 6

```
   1 medsmdmdms plrpqnylfg celkadkdyh fkvdndeneh qlslrtvslg agakdelhiv
  61 eaeamnyegs pikvtlatlk msvqptvslg gfeitppvvl rlkcgsgpvh isgqhlvvyr
 121 rkhqelqamq melqspeykl sklrtstimt dynpnycfag ktssisdlke vprknitlir
 181 glghgafgev yegqvsgmpn dpsplqvavk tlpevcseqd eldflmeali iskfnhqniv
 241 rcigvslqsl prfillelma ggdlksflre trprpsqpss lamldllhva rdiacgcqyl
 301 eenhfihrdi aarnclltcp gpgrvakigd fgmardiyra syyrkggcam lpvkwmppea
 361 fmegiftskt dtwsfgvllw eifslgympy psksnqevle fvtsggrmdp pkncpgpvyr
 421 imtqcwqhqp edrpnfaiil erieyctqdp dvintalpie ygplveeeek vpvrpkdpeg
 481 vppllvsqqa kreeerspaa ppplpttssg kaakkptaae vsvrvprgpa vegghvnmaf
 541 sqsnppselh kvhgsrnkpt slwnptygsw ftekptkknn piakkephdr gnlglegsct
 601 vppnvatgrl pgaslllleps sltanmkevp lfrlrhfpcg nvnygyqqqg lpleaatapg
 661 aghyedtilk sksnsmnqpgp
```

Figure 10

SEQUENCE LISTING

```
<160> NUMBER OF SEQ ID NOS: 22

<210> SEQ ID NO 1
<211> LENGTH: 6226
<212> TYPE: DNA
<213> ORGANISM: Artificial Sequence
<220> FEATURE:
<223> OTHER INFORMATION: Synthetic Construct

<400> SEQUENCE: 1
aagcgggggc ggcagcggtg gtagcagctg gtacctcccg ccgcctctgt tcggagggtc      60
gcggggcacc gaggtgcttt ccggccgccc tctggtcggc cacccaaagc cgcgggcgct     120
gatgatgggt gaggagggggg cggcaagatt tcgggcgccc ctgccctgaa cgccctcagc    180
tgctgccgcc ggggccgctc cagtgcctgc gaactctgag gagccgaggc gccggtgaga     240
gcaaggacgc tgcaaacttg cgcagcgcgg gggctgggat tcacgcccag aagttcagca     300
ggcagacagt ccgaagcctt cccgcagcgg agagatagct tgagggtgcg caagacggca     360
gcctccgccc tcggttcccg cccagaccgg gcagaagagc ttggaggagc cacaaggaac     420
gcaaaaggcg gccaggacag cgtgcagcag ctgggagccg ccgttctcag ccttaaaagt     480
tgcagagatt ggaggctgcc ccgagagggg acagacccca gctccgactg cggggggcag    540
gagaggacgg tacccaactg ccacctccct tcaaccatag tagttcctct gtaccgagcg     600
cagcgagcta cagacggggg cgcggcactc ggcgcggaga gcgggaggct caaggtccca     660
gccagtgagc ccagtgtgct tgagtgtctc tggactcgcc cctgagcttc caggtctgtt     720
tcatttagac tcctgctcgc ctccgtgcag ttgggggaaa gcaagagact tgcgcgcacg     780
cacagtcctc tggagatcag gtggaaggag ccgctgggta ccaaggactg ttcagagcct     840
cttcccatct cggggagagc gaagggtgag gctgggcccg gagagcagtg taaacggcct     900
cctccggcgg gatgggagcc atcgggctcc tgtggctgct gccgctgctg cttctccacgg    960 cagctgtggg ctccgggatg gggaccggcc agcgcgcggg ctccccagct gcgggtgtcgc   1020 cgctgcagcc ccgggagcca ctcagctact cgcgcctgca gaggaagagt ctggcagttg    1080
acttcgtggt gccctcgctc ttccgtgtct acgcccggga cctactgctg ccaccatcct    1140
```

```
cctcggagct gaaggctggc aggcccgagg cccgcggctc gctagctctg gactgcgccc    1200
cgctgctcag gttgctgggg ccggcgccgg gggtctcctg gaccgccggt tcaccagccc    1260
cggcagaggc ccggacgctg tccagggtgc tgaagggcgg ctccgtgcgc aagctccggc    1320
gtgccaagca gttggtgctg gagctggcg aggaggcgat cttggagggt tgcgtcgggc     1380
cccccgggga ggcggctgtg gggctgctcc agttcaatct cagcgagctg ttcagttggt    1440
ggattcgcca aggcgaaggg cgactgagga tccgcctgat gcccgagaag aaggcgtcgg    1500
aagtgggcag agagggaagg ctgtccgcgg caattcgcgc ctcccagccc cgccttctct    1560
tccagatctt cgggactggt catagctcct tggaatcacc aacaaacatg ccatctcctt    1620
ctcctgatta ttttacatgg aatctcacct ggataatgaa agactccttc cctttcctgt    1680
ctcatcgcag ccgatatggt ctggagtgca gctttgactt cccctgtgag ctggagtatt    1740
cccctccact gcatgacctc aggaaccaga gctggtcctg gcgccgcatc ccctccgagg    1800
aggcctccca gatggacttg ctggatgggc ctggggcaga gcgttctaag gagatgccca    1860
gaggctcctt tctccttctc aacacctcag ctgactccaa gcacaccatc ctgagtccgt    1920
ggatgaggag cagcagtgag cactgcacac tggccgtctc ggtgcacagg cacctgcagc    1980
cctctggaag gtacattgcc cagctgctgc cccacaacga ggctgcaaga gagatcctcc    2040
tgatgcccac tccagggaag catggttgga cagtgctcca gggaagaatc gggcgtccag    2100
acaacccatt tcgagtggcc ctggaataca tctccagtgg aaaccgcagc ttgtctgcag    2160
tggacttctt tgccctgaag aactgcagtg aaggaacatc cccaggctcc aagatggccc    2220
tgcagagctc cttcacttgt tggaatggga cagtcctcca gcttgggcag gcctgtgact    2280
tccaccagga ctgtgcccag ggagaagatg agagccagat gtgccggaaa ctgcctgtgg    2340
gtttttactg caactttgaa gatggcttct gtggctggac ccaaggcaca ctgtcacccc    2400
acactcctca gtggcaggtc aggaccctaa aggatgcccg gttccaggac caccaagacc    2460
atgctctatt gctcagtacc actgatgtcc ccgcttctga aagtgctaca gtgaccagtg    2520
ctacgtttcc tgcaccgatc aagagctctc catgtgagct ccgaatgtcc tggctcattc    2580
gtggagtctt gaggggaaac gtgtccttgg tgctagtgga gaacaaaacc gggaaggagc    2640
aaggcaggat ggtctggcat gtcgccgcct atgaaggctt gagcctgtgg cagtggatgg    2700
tgttgcctct cctcgatgtg tctgacaggt tctggctgca gatggtcgca tggtggggac    2760
aaggatccag agccatcgtg gcttttgaca atatctccat cagcctggac tgctacctca    2820
ccattagcgg agaggacaag atcctgcaga atacagcacc caaatcaaga aacctgtttg    2880
agagaaaccc aaacaaggag ctgaaacccg gggaaaattc accaagacag acccccatct    2940
ttgaccctac agttcattgg ctgttcacca catgtgggc cagcgggccc catgcccca     3000 cccaggcaca gtgcaacaac gcctaccaga actccaacct gagcgtggag gtggggagcg    3060 agggcccct gaaaggcatc cagatctgga aggtgccagc caccgacacc tacagcatct    3120
cgggctacgg agctgctggc gggaaaggcg ggaagaacac catgatgcgg tcccacggcg    3180
tgtctgtgct gggcatcttc aacctggaga aggatgacat gctgtacatc ctggttgggc    3240
agcagggaga ggacgcctgc cccagtacaa accagttaat ccagaaagtc tgcattggag    3300
agaacaatgt gatagaagaa gaaatccgtg tgaacagaag cgtgcatgag tgggcaggag    3360
gcggaggagg aggggtggaa gccacctacg tatttaagat gaaggatgga gtgccggtgc    3420
ccctgatcat tgcagccgga ggtggcggca gggcctacgg ggccaagaca gacacgttcc    3480
acccagagag actggagaat aactcctcgg ttctagggct aaacggcaat tccggagccg    3540
```

```
caggtggtgg aggtggctgg aatgataaca cttccttgct ctgggccgga aaatctttgc   3600
aggagggtgc caccggagga cattcctgcc cccaggccat gaagaagtgg gggtgggaga   3660
caagaggggg tttcggaggg ggtggagggg ggtgctcctc aggtggagga ggcggaggat   3720
atataggcgg caatgcagcc tcaaacaatg accccgaaat ggatgggaa gatgggtt     3780
ccttcatcag tccactgggc atcctgtaca ccccagcttt aaaagtgatg aaggccacg    3840
gggaagtgaa tattaagcat tatctaaact gcagtcactg tgaggtagac gaatgtcaca   3900
tggaccctga aagccacaag gtcatctgct tctgtgacca cgggacggtg ctggctgagg   3960
atggcgtctc ctgcattgtg tcacccaccc cggagccaca cctgccactc tcgctgatcc   4020
tctctgtggt gacctctgcc ctcgtggccg ccctggtcct ggctttctcc ggcatcatga   4080
ttgtgtaccg ccggaagcac caggagctgc aagccatgca gatggagctg cagagccctg   4140
agtacaagct gagcaagctc cgcacctcga ccatcatgac cgactacaac cccaactact   4200
gctttgctgg caagacctcc tccatcagtg acctgaagga ggtgccgcgg aaaaacatca   4260
ccctcattcg gggtctgggc catggcgcct ttggggaggt gtatgaaggc caggtgtccg   4320
gaatgcccaa cgacccaagc cccctgcaag tggctgtgaa gacgctgcct gaagtgtgct   4380
ctgaacagga cgaactggat ttcctcatgg aagccctgat catcagcaaa ttcaaccacc   4440
agaacattgt tcgctgcatt ggggtgagcc tgcaatccct gccccggttc atcctgctgg   4500
agctcatggc gggggagac ctcaagtcct tcctccgaga acccgccct cgcccgagcc     4560
agccctcctc cctggccatg ctggaccttc tgcacgtggc tcgggacatt gcctgtggct   4620
gtcagtattt ggaggaaaac cacttcatcc accgagacat tgctgccaga aactgcctct   4680
tgacctgtcc aggccctgga agagtggcca agattggaga cttcgggatg cccgagaca    4740
tctacagggc gagctactat agaaagggag gctgtgccat gctgccagtt aagtggatgc   4800
ccccagaggc cttcatggaa ggaatattca cttctaaaac agacacatgg tcctttggag   4860
tgctgctatg ggaaatcttt tctcttggat atatgccata ccccagcaaa agcaaccagg   4920
aagttctgga gtttgtcacc agtggaggcc ggatggaccc acccaagaac tgccctgggc   4980
ctgtataccg gataatgact cagtgctggc aacatcagcc tgaagacagg cccaactttg   5040
ccatcatttt ggagaggatt gaatactgca cccaggaccc ggatgtaatc aacaccgctt   5100
tgccgataga atatggtcca cttgtggaag aggaagagaa agtgcctgtg aggcccaagg   5160
accctgaggg ggttcctcct ctcctggtct ctcaacaggc aaaacgggag gaggagcgca   5220
gcccagctgc cccaccacct ctgcctacca cctcctctgg caaggctgca agaaacccca   5280
cagctgcaga ggtctctgtt cgagtcccta gagggccggc cgtggaaggg ggacacgtga   5340
atatggcatt ctctcagtcc aaccctcctt cggagttgca caaggtccac ggatccagaa   5400
acaagcccac cagcttgtgg aacccaacgt acggctcctg gtttacagag aaacccacca   5460
aaaagaataa tcctatagca aagaaggagc cacacgacag gggtaacctg gggctggagg   5520
gaagctgtac tgtcccacct aacgttgcaa ctgggagact tccgggggcc tcactgctcc   5580
tagagccctc ttcgctgact gccaatatga aggaggtacc tctgttcagg ctacgtcact   5640
tcccttgtgg aatgtcaat tacggctacc agcaacaggg cttgcccta gaagccgcta    5700
ctgcccctgg agctggtcat tacgaggata ccattctgaa aagcaagaat agcatgaacc   5760
agcctgggcc ctgagctcgg tcgcacactc acttctcttc cttgggatcc ctaagaccgt   5820
ggaggagaga gaggcaatgg ctccttcaca aaccagagac caaatgtcac gttttgtttt   5880
```

-continued

```
gtgccaacct attttgaagt accaccaaaa aagctgtatt tgaaaatgc tttagaaagg    5940 ttttgagcat gggttcatcc tattctttcg aaagaagaaa atatcataaa aatgagtgat    6000
aaatacaagg cccagatgtg gttgcataag gtttttatgc atgtttgttg tatacttcct    6060
tatgcttctt ttaaattgtg tgtgctctgc ttcaatgtag tcagaattag ctgcttctat    6120
gtttcatagt tggggtcata gatgtttcct tgccttgttg atgtggacat gagccatttg    6180
aggggagagg gaacggaaat aaaggagtta tttgtaatga ctaaaa                  6226
```

<210> SEQ ID NO 2
<211> LENGTH: 1620
<212> TYPE: PRT
<213> ORGANISM: Artificial Sequence
<220> FEATURE:
<223> OTHER INFORMATION: Synthetic Construct

<400> SEQUENCE: 2

```
Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Ser Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300
```

-continued

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
            325                 330                 335

Trp Met Arg Ser Ser Ser Glu His Cys Thr Leu Ala Val Ser Val His
                340                 345                 350

Arg His Leu Gln Pro Ser Gly Arg Tyr Ile Ala Gln Leu Leu Pro His
            355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
            435                 440                 445

Leu Gln Leu Gly Gln Ala Cys Asp Phe His Gln Asp Cys Ala Gln Gly
450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
            515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile

-continued

```
                725                 730                 735
Ser Gly Tyr Gly Ala Gly Gly Lys Gly Gly Lys Asn Thr Met Met
                740                 745                 750
Arg Ser His Gly Val Ser Val Leu Gly Ile Phe Asn Leu Glu Lys Asp
                755                 760                 765
Asp Met Leu Tyr Ile Leu Val Gly Gln Gln Gly Glu Asp Ala Cys Pro
    770                 775                 780
Ser Thr Asn Gln Leu Ile Gln Lys Val Cys Ile Gly Glu Asn Asn Val
785                 790                 795                 800
Ile Glu Glu Glu Ile Arg Val Asn Arg Ser Val His Glu Trp Ala Gly
                805                 810                 815
Gly Gly Gly Gly Gly Gly Ala Thr Tyr Val Phe Lys Met Lys Asp
                820                 825                 830
Gly Val Pro Val Pro Leu Ile Ile Ala Ala Gly Gly Gly Gly Arg Ala
                835                 840                 845
Tyr Gly Ala Lys Thr Asp Thr Phe His Pro Glu Arg Leu Glu Asn Asn
    850                 855                 860
Ser Ser Val Leu Gly Leu Asn Gly Asn Ser Gly Ala Ala Gly Gly Gly
865                 870                 875                 880
Gly Gly Trp Asn Asp Asn Thr Ser Leu Leu Trp Ala Gly Lys Ser Leu
                885                 890                 895
Gln Glu Gly Ala Thr Gly Gly His Ser Cys Pro Gln Ala Met Lys Lys
                900                 905                 910
Trp Gly Trp Glu Thr Arg Gly Gly Phe Gly Gly Gly Gly Gly Cys
                915                 920                 925
Ser Ser Gly Gly Gly Gly Gly Tyr Ile Gly Gly Asn Ala Ala Ser
    930                 935                 940
Asn Asn Asp Pro Glu Met Asp Gly Glu Asp Gly Val Ser Phe Ile Ser
945                 950                 955                 960
Pro Leu Gly Ile Leu Tyr Thr Pro Ala Leu Lys Val Met Glu Gly His
                965                 970                 975
Gly Glu Val Asn Ile Lys His Tyr Leu Asn Cys Ser His Cys Glu Val
                980                 985                 990
Asp Glu Cys His Met Asp Pro Glu Ser His Lys Val Ile Cys Phe Cys
            995                1000                1005
Asp His Gly Thr Val Leu Ala Glu Asp Gly Val Ser Cys Ile Val
    1010                1015                1020
Ser Pro Thr Pro Glu Pro His Leu Pro Leu Ser Leu Ile Leu Ser
    1025                1030                1035
Val Val Thr Ser Ala Leu Val Ala Ala Leu Val Leu Ala Phe Ser
    1040                1045                1050
Gly Ile Met Ile Val Tyr Arg Arg Lys His Gln Glu Leu Gln Ala
    1055                1060                1065
Met Gln Met Glu Leu Gln Ser Pro Glu Tyr Lys Leu Ser Lys Leu
    1070                1075                1080
Arg Thr Ser Thr Ile Met Thr Asp Tyr Asn Pro Asn Tyr Cys Phe
    1085                1090                1095
Ala Gly Lys Thr Ser Ser Ile Ser Asp Leu Lys Glu Val Pro Arg
    1100                1105                1110
Lys Asn Ile Thr Leu Ile Arg Gly Leu Gly His Gly Ala Phe Gly
    1115                1120                1125
Glu Val Tyr Glu Gly Gln Val Ser Gly Met Pro Asn Asp Pro Ser
    1130                1135                1140
```

```
Pro Leu Gln Val Ala Val Lys Thr Leu Pro Glu Val Cys Ser Glu
    1145                1150                1155

Gln Asp Glu Leu Asp Phe Leu Met Glu Ala Leu Ile Ile Ser Lys
    1160                1165                1170

Phe Asn His Gln Asn Ile Val Arg Cys Ile Gly Val Ser Leu Gln
    1175                1180                1185

Ser Leu Pro Arg Phe Ile Leu Leu Glu Leu Met Ala Gly Gly Asp
    1190                1195                1200

Leu Lys Ser Phe Leu Arg Glu Thr Arg Pro Arg Pro Ser Gln Pro
    1205                1210                1215

Ser Ser Leu Ala Met Leu Asp Leu Leu His Val Ala Arg Asp Ile
    1220                1225                1230

Ala Cys Gly Cys Gln Tyr Leu Glu Glu Asn His Phe Ile His Arg
    1235                1240                1245

Asp Ile Ala Ala Arg Asn Cys Leu Leu Thr Cys Pro Gly Pro Gly
    1250                1255                1260

Arg Val Ala Lys Ile Gly Asp Phe Gly Met Ala Arg Asp Ile Tyr
    1265                1270                1275

Arg Ala Ser Tyr Tyr Arg Lys Gly Gly Cys Ala Met Leu Pro Val
    1280                1285                1290

Lys Trp Met Pro Pro Glu Ala Phe Met Glu Gly Ile Phe Thr Ser
    1295                1300                1305

Lys Thr Asp Thr Trp Ser Phe Gly Val Leu Leu Trp Glu Ile Phe
    1310                1315                1320

Ser Leu Gly Tyr Met Pro Tyr Pro Ser Lys Ser Asn Gln Glu Val
    1325                1330                1335

Leu Glu Phe Val Thr Ser Gly Gly Arg Met Asp Pro Pro Lys Asn
    1340                1345                1350

Cys Pro Gly Pro Val Tyr Arg Ile Met Thr Gln Cys Trp Gln His
    1355                1360                1365

Gln Pro Glu Asp Arg Pro Asn Phe Ala Ile Ile Leu Glu Arg Ile
    1370                1375                1380

Glu Tyr Cys Thr Gln Asp Pro Asp Val Ile Asn Thr Ala Leu Pro
    1385                1390                1395

Ile Glu Tyr Gly Pro Leu Val Glu Glu Glu Glu Lys Val Pro Val
    1400                1405                1410

Arg Pro Lys Asp Pro Glu Gly Val Pro Pro Leu Leu Val Ser Gln
    1415                1420                1425

Gln Ala Lys Arg Glu Glu Glu Arg Ser Pro Ala Ala Pro Pro Pro
    1430                1435                1440

Leu Pro Thr Thr Ser Ser Gly Lys Ala Ala Lys Lys Pro Thr Ala
    1445                1450                1455

Ala Glu Val Ser Val Arg Val Pro Arg Gly Pro Ala Val Glu Gly
    1460                1465                1470

Gly His Val Asn Met Ala Phe Ser Gln Ser Asn Pro Pro Ser Glu
    1475                1480                1485

Leu His Lys Val His Gly Ser Arg Asn Lys Pro Thr Ser Leu Trp
    1490                1495                1500

Asn Pro Thr Tyr Gly Ser Trp Phe Thr Glu Lys Pro Thr Lys Lys
    1505                1510                1515

Asn Asn Pro Ile Ala Lys Lys Glu Pro His Asp Arg Gly Asn Leu
    1520                1525                1530
```

```
Gly Leu Glu Gly Ser Cys Thr Val Pro Pro Asn Val Ala Thr Gly
    1535                1540                1545

Arg Leu Pro Gly Ala Ser Leu Leu Leu Glu Pro Ser Ser Leu Thr
    1550                1555                1560

Ala Asn Met Lys Glu Val Pro Leu Phe Arg Leu Arg His Phe Pro
    1565                1570                1575

Cys Gly Asn Val Asn Tyr Gly Tyr Gln Gln Gln Gly Leu Pro Leu
    1580                1585                1590

Glu Ala Ala Thr Ala Pro Gly Ala Gly His Tyr Glu Asp Thr Ile
    1595                1600                1605

Leu Lys Ser Lys Asn Ser Met Asn Gln Pro Gly Pro
    1610                1615                1620

<210> SEQ ID NO 3
<211> LENGTH: 5293
<212> TYPE: DNA
<213> ORGANISM: Artificial Sequence
<220> FEATURE:
<223> OTHER INFORMATION: Synthetic Construct

<400> SEQUENCE: 3
agagacttgc gcgcacgcac agtcctctgg agatcaggtg aaggagccg  ctgggtacca      60
aggactgttc agagcctctt cccatctcgg ggagagcgaa gggtgaggct gggcccggag     120
agcagtgtaa acggcctcct ccggcgggat gggagccatc gggctcctgt ggctgctgcc     180
gctgctgctt ccacggcag  ctgtgggctc cgggatgggg accggccagc gcgcgggctc     240
cccagctgcg gggccgccgc tgcagccccg ggagccactc agctactcgc gcctgcagag     300
gaagagtctg gcagttgact tcgtggtgcc ctcgctcttc cgtgtctacg cccgggacct     360
actgctgcca ccatcctcct cggagctgaa ggctggcagg cccgaggccc gcggctcgct     420
agctctggac tgcgccccgc tgctcaggtt gctggggccg gcgccggggg tctcctggac     480
cgccggttca ccagccccgg cagaggcccg acgctgtcc  aggtgctga  agggcggctc     540
cgtgcgcaag ctccggcgtg ccaagcagtt ggtgctggag ctgggcgagg aggcgatctt     600
ggagggttgc gtcgggcccc ccggggaggc ggctgtgggg ctgctccagt tcaatctcag     660
cgagctgttc agttggtgga ttcgccaagg cgaagggcga ctgaggatcc gcctgatgcc     720
cgagaagaag cgctcggaag tgggcagaga gggaaggctg tccgcggcaa ttcgcgcctc     780
ccagccccgc cttctcttcc agatcttcgg gactggtcat agctccttgg aatcaccaac     840
aaacatgcct tctccttctc ctgattattt tacatggaat ctcacctgga taatgaaaga     900
ctccttccct ttcctgtctc atcgcagccg atatggtctg gagtgcagct ttgacttccc     960
ctgtgagctg gagtattccc ctccactgca tgacctcagg aaccagagct ggtcctggcg    1020
ccgcatcccc tccgaggagg cctcccagat ggacttgctg gatgggcctg ggcagagcg    1080
ttctaaggag atgcccagag gctccttttct ccttctcaac acctcagctg actccaagca    1140
caccatcctg agtccgtgga tgaggagcag cagtgagcac tgcacactgg ccgtctcggt    1200
gcacaggcac ctgcagccct ctggaaggta cattgcccag ctgctgcccc acaacgaggc    1260
tgcaagagat atcctcctga tgcccactcc agggaagcat ggttggacag tgctccaggg    1320
aagaatcggg cgtccagaca acccatttcg agtggccctg aatacatct  ccagtggaaa    1380
ccgcagcttg tctgcagtgg acttctttgc cctgaagaac tgcagtgaag gaacatcccc    1440
aggctccaag atgccctgc  agagctcctt cacttgttgg aatgggacag tcctccagct    1500
tgggcaggcc tgtgacttcc accaggactg tgcccaggga gaagatgaga gccagatgtg    1560
```

```
ccggaaactg cctgtgggtt tttactgcaa ctttgaagat ggcttctgtg gctggaccca    1620
aggcacactg tcaccccaca ctcctcagtg gcaggtcagg accctaaagg atgcccggtt    1680
ccaggaccac caagaccatg ctctattgct cagtaccact gatgtccccg cttctgaaag    1740
tgctacagtg accagtgcta cgtttcctgc accgatcaag agctctccat gtgagctccg    1800
aatgtcctgg ctcattcgtg gagtcttgag gggaaacgtg tccttggtgc tagtggagaa    1860
caaaaccggg aaggagcaag gcaggatggt ctggcatgtc ccgcctatg aaggcttgag     1920 cctgtggcag tggatggtgt tgcctctcct cgatgtgtct gacaggttct ggctgcagat    1980
ggtcgcatgt gggacaag gatccagagc catcgtggct tttgacaata tctccatcag      2040
cctggactgc tacctcacca ttagcggaga ggacaagatc ctgcagaata cagcacccaa    2100
atcaagaaac ctgtttgaga gaaacccaaa caaggagctg aaacccgggg aaaattcacc    2160
aagacagacc cccatctttg accctacagt tcattggctg ttcaccacat gtggggccag    2220
cgggccccat ggccccaccc aggcacagtg caacaacgcc taccagaact caacctgag    2280 cgtggaggtg gggagcgagg gccccctgaa aggcatccag atctggaagg tgccagccac    2340
cgacacctac agcatctcgg gctacggagc tgctggcggg aaaggcggga agaacaccat    2400
gatgcggtcc cacggcgtgt ctgtgctggg catcttcaac ctggagaagg atgacatgct    2460
gtacatcctg gttgggcagc agggagagga cgcctgcccc agtacaaacc agttaatcca    2520
gaaagtctgc attggagaga caatgtgat agaagaagaa atccgtgtga acagaagcgt     2580
gcatgagtgg gcaggaggcg gaggaggagg gggtggagcc acctacgtat ttaagatgaa    2640
ggatggagtg ccggtgcccc tgatcattgc agccggaggt ggtggcaggg cctacggggc    2700
caagacagac acgttccacc cagagagact ggagaataac tcctcggttc tagggctaaa    2760
cggcaattcc ggagccgcag gtggtggagg tggctggaat gataacactt ccttgctctg    2820
ggccggaaaa tctttgcagg agggtgccac cggaggacat tcctgccccc aggccatgaa    2880
gaagtggggg tgggagacaa gaggggggttt cggagggggt ggagggggggt gctcctcagg  2940 tggaggaggc ggaggatata taggcggcaa tgcagcctca aacaatgacc ccgaaatgga   3000
tggggaagat ggggtttcct tcatcagtcc actgggcatc ctgtacaccc cagctttaaa    3060
agtgatggaa ggccacgggg aagtgaatat taagcattat ctaaactgca gtcactgtga    3120
ggtagacgaa tgtcacatgg accctgaaag ccacaaggtc atctgcttct gtgaccacgg    3180
gacggtgctg gctgaggatg gcgtctcctg cattgtgtca cccaccccgg agccacacct    3240
gccactctcg ctgatcctct ctgtggtgac ctctgccctc gtggccgccc tggtcctggc    3300
tttctccggc atcatgattg tgtaccgccg gaagcaccag gagctgcaag ccatgcagat    3360
ggagctgcag agccctgagt acaagctgag caagctccgc acctcgacca tcatgaccga    3420
ctacaacccc aactactgct ttgctggcaa gacctcctcc atcagtgacc tgaaggaggt    3480
gccgcgcaaa aacatcaccc tcattcgggg tctgggccat ggcgcctttg gggaggtgta    3540
tgaaggccag gtgtccggaa tgcccaacga cccaagcccc ctgcaagtgg ctgtgaagac    3600
gctgcctgaa gtgtgctctg aacaggacga actggattc ctcatggaag ccctgatcat     3660
cagcaaattc aaccaccaga acattgttcg ctgcattggg gtgagcctgc aatccctgcc    3720
ccggttcatc ctgctggagc tcatggcggg gggagacctc aagtccttcc tccgagagac    3780
ccgcccctcg ccgagccagc cctcctcccc ggccatgctg accttctgc acgtggctcg     3840 ggacattgcc tgtggctgtc agtatttgga ggaaaaccac ttcatccacc gagacattgc    3900
```

```
tgccagaaac tgcctcttga cctgtccagg ccctggaaga gtggccaaga ttggagactt    3960
cgggatggcc cgagacatct acagggcgag ctactataga aagggaggct gtgccatgct    4020
gccagttaag tggatgcccc cagaggcctt catggaagga atattcactt ctaaaacaga    4080
cacatggtcc tttggagtgc tgctatggga aatcttttct cttggatata tgccataccc    4140
cagcaaaagc aaccaggaag ttctggagtt tgtcaccagt ggaggccgga tggacccacc    4200
caagaactgc cctgggcctg tataccggat aatgactcag tgctggcaac atcagcctga    4260
agacaggccc aactttgcca tcattttgga gaggattgaa tactgcaccc aggacccgga    4320
tgtaatcaac accgctttgc cgatagaata tggtccactt gtggaagagg aagagaaagt    4380
gcctgtgagg cccaaggacc ctgagggggt tcctcctctc ctggtctctc aacaggcaaa    4440
acgggaggag gagcgcagcc cagctgcccc accacctctg cctaccacct cctctggcaa    4500
ggctgcaaag aaacccacag ctgcagaggt ctctgttcga gtccctagag ggccggccgt    4560
ggaaggggga cacgtgaata tggcattctc tcagtccaac cctccttcgg agttgcacag    4620
ggtccacgga tccagaaata agcccaccag cttgtggaac ccaacgtacg gctcctggtt    4680
tacagagaaa cccaccaaaa agaataatcc tatagcaaag aaggagccac acgagagggg    4740
taacctgggg ctggagggaa gctgtactgt cccacctaac gttgcaactg ggagacttcc    4800
gggggcctca ctgctcctag agccctcttc gctgactgcc aatatgaagg aggtacctct    4860
gttcaggcta cgtcacttcc cttgtgggaa tgtcaattac ggctaccagc aacagggctt    4920
gcccttagaa gccgctactg cccctggagc tggtcattac gaggatacca ttctgaaaag    4980
caagaatagc atgaaccagc ctgggccctg agctcggtcg cactcactcact tctcttcctt    5040 gggatcccta agaccgtgga ggagagagag gcaatcaatg gctccttttca caaccagag    5100 accaaatgtc acgttttgtt ttgtgccaac ctatttgaa gtaccaccaa aaaagctgta    5160
ttttgaaaat gctttagaaa ggttttgagc atgggttcat cctattcttt cgaaagaaga    5220
aaatatcata aaaatgagtg ataaatacaa ggccagatgt ggttgcataa ggttttatg    5280 catgtttgtt gta                                                      5293
```

<210> SEQ ID NO 4
<211> LENGTH: 1620
<212> TYPE: PRT
<213> ORGANISM: Artificial Sequence
<220> FEATURE:
<223> OTHER INFORMATION: Synthetic Construct

<400> SEQUENCE: 4

```
Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110
```

-continued

```
Gly Ser Pro Ala Pro Ala Glu Ala Arg Thr Leu Ser Arg Val Leu Lys
            115                 120                 125
Gly Gly Ser Val Arg Lys Leu Arg Arg Ala Lys Gln Leu Val Leu Glu
130                 135                 140
Leu Gly Glu Glu Ala Ile Leu Glu Gly Cys Val Gly Pro Pro Gly Glu
145                 150                 155                 160
Ala Ala Val Gly Leu Leu Gln Phe Asn Leu Ser Glu Leu Phe Ser Trp
                165                 170                 175
Trp Ile Arg Gln Gly Glu Gly Arg Leu Arg Ile Arg Leu Met Pro Glu
            180                 185                 190
Lys Lys Ala Ser Glu Val Gly Arg Glu Gly Arg Leu Ser Ala Ala Ile
        195                 200                 205
Arg Ala Ser Gln Pro Arg Leu Leu Phe Gln Ile Phe Gly Thr Gly His
    210                 215                 220
Ser Ser Leu Glu Ser Pro Thr Asn Met Pro Ser Pro Ser Pro Asp Tyr
225                 230                 235                 240
Phe Thr Trp Asn Leu Thr Trp Ile Met Lys Asp Ser Phe Pro Phe Leu
                245                 250                 255
Ser His Arg Ser Arg Tyr Gly Leu Glu Cys Ser Phe Asp Phe Pro Cys
            260                 265                 270
Glu Leu Glu Tyr Ser Pro Pro Leu His Asp Leu Arg Asn Gln Ser Trp
        275                 280                 285
Ser Trp Arg Arg Ile Pro Ser Glu Glu Ala Ser Gln Met Asp Leu Leu
    290                 295                 300
Asp Gly Pro Gly Ala Glu Arg Ser Lys Glu Met Pro Arg Gly Ser Phe
305                 310                 315                 320
Leu Leu Leu Asn Thr Ser Ala Asp Ser Lys His Thr Ile Leu Ser Pro
                325                 330                 335
Trp Met Arg Ser Ser Ser Glu His Cys Thr Leu Ala Val Ser Val His
            340                 345                 350
Arg His Leu Gln Pro Ser Gly Arg Tyr Ile Ala Gln Leu Leu Pro His
        355                 360                 365
Asn Glu Ala Ala Arg Glu Ile Leu Leu Met Pro Thr Pro Gly Lys His
    370                 375                 380
Gly Trp Thr Val Leu Gln Gly Arg Ile Gly Arg Pro Asp Asn Pro Phe
385                 390                 395                 400
Arg Val Ala Leu Glu Tyr Ile Ser Ser Gly Asn Arg Ser Leu Ser Ala
                405                 410                 415
Val Asp Phe Phe Ala Leu Lys Asn Cys Ser Glu Gly Thr Ser Pro Gly
            420                 425                 430
Ser Lys Met Ala Leu Gln Ser Ser Phe Thr Cys Trp Asn Gly Thr Val
        435                 440                 445
Leu Gln Leu Gly Gln Ala Cys Asp Phe His Gln Asp Cys Ala Gln Gly
    450                 455                 460
Glu Asp Glu Ser Gln Met Cys Arg Lys Leu Pro Val Gly Phe Tyr Cys
465                 470                 475                 480
Asn Phe Glu Asp Gly Phe Cys Gly Trp Thr Gln Gly Thr Leu Ser Pro
                485                 490                 495
His Thr Pro Gln Trp Gln Val Arg Thr Leu Lys Asp Ala Arg Phe Gln
            500                 505                 510
Asp His Gln Asp His Ala Leu Leu Leu Ser Thr Thr Asp Val Pro Ala
        515                 520                 525
Ser Glu Ser Ala Thr Val Thr Ser Ala Thr Phe Pro Ala Pro Ile Lys
```

```
              530                 535                 540
Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                    565                 570                 575

Gln Gly Arg Met Val Trp His Val Ala Ala Tyr Glu Gly Leu Ser Leu
                580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
        610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                    645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
        690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                    725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
        770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                    805                 810                 815

Gly Gly Gly Gly Gly Gly Ala Thr Tyr Val Phe Lys Met Lys Asp
                820                 825                 830

Gly Val Pro Val Pro Leu Ile Ile Ala Ala Gly Gly Gly Gly Arg Ala
            835                 840                 845

Tyr Gly Ala Lys Thr Asp Thr Phe His Pro Glu Arg Leu Glu Asn Asn
        850                 855                 860

Ser Ser Val Leu Gly Leu Asn Gly Asn Ser Ala Ala Gly Gly Gly Gly
865                 870                 875                 880

Gly Gly Trp Asn Asp Asn Thr Ser Leu Leu Trp Ala Gly Lys Ser Leu
                    885                 890                 895

Gln Glu Gly Ala Thr Gly Gly His Ser Cys Pro Gln Ala Met Lys Lys
                900                 905                 910

Trp Gly Trp Glu Thr Arg Gly Gly Phe Gly Gly Gly Gly Gly Gly Cys
            915                 920                 925

Ser Ser Gly Gly Gly Gly Gly Tyr Ile Gly Gly Asn Ala Ala Ser
        930                 935                 940

Asn Asn Asp Pro Glu Met Asp Gly Glu Asp Gly Val Ser Phe Ile Ser
945                 950                 955                 960
```

-continued

```
Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
            980                 985                 990

Asp Glu Cys His Met Asp Pro Glu Ser His Lys Val Ile Cys Phe Cys
            995                 1000                1005

Asp His Gly Thr Val Leu Ala Glu Asp Gly Val Ser Cys Ile Val
        1010                1015                1020

Ser Pro Thr Pro Glu Pro His Leu Pro Leu Ser Leu Ile Leu Ser
        1025                1030                1035

Val Val Thr Ser Ala Leu Val Ala Ala Leu Val Leu Ala Phe Ser
        1040                1045                1050

Gly Ile Met Ile Val Tyr Arg Arg Lys His Gln Glu Leu Gln Ala
        1055                1060                1065

Met Gln Met Glu Leu Gln Ser Pro Glu Tyr Lys Leu Ser Lys Leu
        1070                1075                1080

Arg Thr Ser Thr Ile Met Thr Asp Tyr Asn Pro Asn Tyr Cys Phe
        1085                1090                1095

Ala Gly Lys Thr Ser Ser Ile Ser Asp Leu Lys Glu Val Pro Arg
        1100                1105                1110

Lys Asn Ile Thr Leu Ile Arg Gly Leu Gly His Gly Ala Phe Gly
        1115                1120                1125

Glu Val Tyr Glu Gly Gln Val Ser Gly Met Pro Asn Asp Pro Ser
        1130                1135                1140

Pro Leu Gln Val Ala Val Lys Thr Leu Pro Glu Val Cys Ser Glu
        1145                1150                1155

Gln Asp Glu Leu Asp Phe Leu Met Glu Ala Leu Ile Ile Ser Lys
        1160                1165                1170

Phe Asn His Gln Asn Ile Val Arg Cys Ile Gly Val Ser Leu Gln
        1175                1180                1185

Ser Leu Pro Arg Phe Ile Leu Leu Glu Leu Met Ala Gly Gly Asp
        1190                1195                1200

Leu Lys Ser Phe Leu Arg Glu Thr Arg Pro Arg Pro Ser Gln Pro
        1205                1210                1215

Ser Ser Leu Ala Met Leu Asp Leu Leu His Val Ala Arg Asp Ile
        1220                1225                1230

Ala Cys Gly Cys Gln Tyr Leu Glu Glu Asn His Phe Ile His Arg
        1235                1240                1245

Asp Ile Ala Ala Arg Asn Cys Leu Leu Thr Cys Pro Gly Pro Gly
        1250                1255                1260

Arg Val Ala Lys Ile Gly Asp Phe Gly Met Ala Arg Asp Ile Tyr
        1265                1270                1275

Arg Ala Ser Tyr Tyr Arg Lys Gly Gly Cys Ala Met Leu Pro Val
        1280                1285                1290

Lys Trp Met Pro Pro Glu Ala Phe Met Glu Gly Ile Phe Thr Ser
        1295                1300                1305

Lys Thr Asp Thr Trp Ser Phe Gly Val Leu Leu Trp Glu Ile Phe
        1310                1315                1320

Ser Leu Gly Tyr Met Pro Tyr Pro Ser Lys Ser Asn Gln Glu Val
        1325                1330                1335

Leu Glu Phe Val Thr Ser Gly Gly Arg Met Asp Pro Pro Lys Asn
        1340                1345                1350
```

| | | | | | | | | | | |
|---|---|---|---|---|---|---|---|---|---|---|
| Cys | Pro<br>1355 | Gly | Pro | Val | Tyr<br>1360 | Arg | Ile | Met | Thr<br>1365 | Gln | Cys | Trp | Gln | His |

Cys Pro Gly Pro Val Tyr Arg Ile Met Thr Gln Cys Trp Gln His
    1355            1360                1365

Gln Pro Glu Asp Arg Pro Asn Phe Ala Ile Ile Leu Glu Arg Ile
    1370            1375                1380

Glu Tyr Cys Thr Gln Asp Pro Asp Val Ile Asn Thr Ala Leu Pro
    1385            1390                1395

Ile Glu Tyr Gly Pro Leu Val Glu Glu Glu Lys Val Pro Val
    1400            1405                1410

Arg Pro Lys Asp Pro Glu Gly Val Pro Pro Leu Leu Val Ser Gln
    1415            1420                1425

Gln Ala Lys Arg Glu Glu Arg Ser Pro Ala Ala Pro Pro Pro
    1430            1435                1440

Leu Pro Thr Thr Ser Ser Gly Lys Ala Ala Lys Lys Pro Thr Ala
    1445            1450                1455

Ala Glu Val Ser Val Arg Val Pro Arg Gly Pro Ala Val Glu Gly
    1460            1465                1470

Gly His Val Asn Met Ala Phe Ser Gln Ser Asn Pro Pro Ser Glu
    1475            1480                1485

Leu His Arg Val His Gly Ser Arg Asn Lys Pro Thr Ser Leu Trp
    1490            1495                1500

Asn Pro Thr Tyr Gly Ser Trp Phe Thr Glu Lys Pro Thr Lys Lys
    1505            1510                1515

Asn Asn Pro Ile Ala Lys Lys Glu Pro His Glu Arg Gly Asn Leu
    1520            1525                1530

Gly Leu Glu Gly Ser Cys Thr Val Pro Pro Asn Val Ala Thr Gly
    1535            1540                1545

Arg Leu Pro Gly Ala Ser Leu Leu Leu Glu Pro Ser Ser Leu Thr
    1550            1555                1560

Ala Asn Met Lys Glu Val Pro Leu Phe Arg Leu Arg His Phe Pro
    1565            1570                1575

Cys Gly Asn Val Asn Tyr Gly Tyr Gln Gln Gln Gly Leu Pro Leu
    1580            1585                1590

Glu Ala Ala Thr Ala Pro Gly Ala Gly His Tyr Glu Asp Thr Ile
    1595            1600                1605

Leu Lys Ser Lys Asn Ser Met Asn Gln Pro Gly Pro
    1610            1615                1620

<210> SEQ ID NO 5
<211> LENGTH: 2043
<212> TYPE: DNA
<213> ORGANISM: Artificial Sequence
<220> FEATURE:
<223> OTHER INFORMATION: Synthetic Construct

<400> SEQUENCE: 5
atggaagatt cgatggacat ggacatgagc cccctgaggc cccagaacta tcttttcggt     60
tgtgaactaa aggccgacaa agattatcac tttaaggtgg ataatgatga aaatgagcac    120
cagttatctt taagaacggt cagtttaggg gctggtgcaa aggatgagtt gcacattgtt    180
gaagcagagg caatgaatta cgaaggcagt ccaattaaag taacactggc aactttgaaa    240
atgtctgtac agccaacggt ttcccttggg ggctttgaaa taacaccacc agtggtctta    300
aggttgaagt gtggttcagg gccagtgcat attagtggac agcacttagt agtgtaccgc    360
cggaagcacc aggagctgca agccatgcag atggagctgc agagccctga gtacaagctg    420
agcaagctcc gcacctcgac catcatgacc gactacaacc ccaactactg ctttgctggc    480

```
aagacctcct ccatcagtga cctgaaggag gtgccgcgga aaaacatcac cctcattcgg    540
ggtctgggcc atggcgcctt tggggaggtg tatgaaggcc aggtgtccgg aatgcccaac    600
gacccaagcc ccctgcaagt ggctgtgaag acgctgcctg aagtgtgctc tgaacaggac    660
gaactggatt tcctcatgga agccctgatc atcagcaaat tcaaccacca gaacattgtt    720
cgctgcattg gggtgagcct gcaatccctg ccccggttca tcctgctgga gctcatggcg    780
ggggagacc tcaagtcctt cctccgagag acccgccctc gcccgagcca gccctcctcc     840
ctggccatgc tggaccttct gcacgtggct cgggacattg cctgtggctg tcagtatttg    900
gaggaaaacc acttcatcca ccgagacatt gctgccagaa actgcctctt gacctgtcca    960
ggccctggaa gagtggccaa gattggagac ttcgggatgg cccgagacat ctacagggcg   1020
agctactata gaaagggagg ctgtgccatg ctgccagtta gtggatgcc cccagaggcc    1080
ttcatggaag gaatattcac ttctaaaaca gacacatggt cctttggagt gctgctatgg   1140
gaaatctttt ctcttggata tatgccatac cccagcaaaa gcaaccagga agttctggag   1200
tttgtcacca gtggaggccg gatggaccca cccaagaact gccctgggcc tgtataccgg   1260
ataatgactc agtgctggca acatcagcct gaagacaggc ccaactttgc catcattttg   1320
gagaggattg aatactgcac ccaggacccg gatgtaatca caccgctttt gccgatagaa   1380
tatggtccac ttgtggaaga ggaagagaaa gtgcctgtga ggcccaagga ccctgagggg   1440
gttcctcctc tcctggtctc tcaacaggca aaacgggagg aggagcgcag cccagctgcc   1500
ccaccacctc tgcctaccac ctcctctggc aaggctgcaa agaaacccac agctgcagag   1560
gtctctgttc gagtccctag agggccggcc gtggaagggg gacacgtgaa tatggcattc   1620
tctcagtcca accctccttc ggagttgcac aaggtccacg gatccagaaa caagcccacc   1680
agcttgtgga acccaacgta cggctcctgg tttacagaga aacccaccaa aaagaataat   1740
cctatagcaa agaaggagcc acacgacagg ggtaacctgg ggctggaggg aagctgtact   1800
gtcccaccta acgttgcaac tgggagactt ccgggggcct cactgctcct agagccctct   1860
tcgctgactg ccaatatgaa ggaggtacct ctgttcaggc tacgtcactt cccttgtggg   1920
aatgtcaatt acggctacca gcaacagggc ttgcccttag aagccgctac tgcccctgga   1980
gctggtcatt acgaggatac cattctgaaa agcaagaata gcatgaacca gcctgggccc   2040
tga                                                                  2043
```

<210> SEQ ID NO 6
<211> LENGTH: 680
<212> TYPE: PRT
<213> ORGANISM: Artificial Sequence
<220> FEATURE:
<223> OTHER INFORMATION: Synthetic Construct

<400> SEQUENCE: 6

```
Met Glu Asp Ser Met Asp Met Asp Met Ser Pro Leu Arg Pro Gln Asn
1               5                  10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80
```

-continued

```
Met Ser Val Gln Pro Thr Val Ser Leu Gly Gly Phe Glu Ile Thr Pro
                85                  90                  95
Pro Val Val Leu Arg Leu Lys Cys Gly Ser Gly Pro Val His Ile Ser
            100                 105                 110
Gly Gln His Leu Val Val Tyr Arg Arg Lys His Gln Glu Leu Gln Ala
        115                 120                 125
Met Gln Met Glu Leu Gln Ser Pro Glu Tyr Lys Leu Ser Lys Leu Arg
    130                 135                 140
Thr Ser Thr Ile Met Thr Asp Tyr Asn Pro Asn Tyr Cys Phe Ala Gly
145                 150                 155                 160
Lys Thr Ser Ser Ile Ser Asp Leu Lys Glu Val Pro Arg Lys Asn Ile
                165                 170                 175
Thr Leu Ile Arg Gly Leu Gly His Gly Ala Phe Gly Glu Val Tyr Glu
            180                 185                 190
Gly Gln Val Ser Gly Met Pro Asn Asp Pro Ser Pro Leu Gln Val Ala
        195                 200                 205
Val Lys Thr Leu Pro Glu Val Cys Ser Glu Gln Asp Glu Leu Asp Phe
    210                 215                 220
Leu Met Glu Ala Leu Ile Ile Ser Lys Phe Asn His Gln Asn Ile Val
225                 230                 235                 240
Arg Cys Ile Gly Val Ser Leu Gln Ser Leu Pro Arg Phe Ile Leu Leu
                245                 250                 255
Glu Leu Met Ala Gly Gly Asp Leu Lys Ser Phe Leu Arg Glu Thr Arg
            260                 265                 270
Pro Arg Pro Ser Gln Pro Ser Ser Leu Ala Met Leu Asp Leu Leu His
        275                 280                 285
Val Ala Arg Asp Ile Ala Cys Gly Cys Gln Tyr Leu Glu Glu Asn His
    290                 295                 300
Phe Ile His Arg Asp Ile Ala Ala Arg Asn Cys Leu Leu Thr Cys Pro
305                 310                 315                 320
Gly Pro Gly Arg Val Ala Lys Ile Gly Asp Phe Gly Met Ala Arg Asp
                325                 330                 335
Ile Tyr Arg Ala Ser Tyr Tyr Arg Lys Gly Gly Cys Ala Met Leu Pro
            340                 345                 350
Val Lys Trp Met Pro Pro Glu Ala Phe Met Glu Gly Ile Phe Thr Ser
        355                 360                 365
Lys Thr Asp Thr Trp Ser Phe Gly Val Leu Leu Trp Glu Ile Phe Ser
    370                 375                 380
Leu Gly Tyr Met Pro Tyr Pro Ser Lys Ser Asn Gln Glu Val Leu Glu
385                 390                 395                 400
Phe Val Thr Ser Gly Gly Arg Met Asp Pro Pro Lys Asn Cys Pro Gly
                405                 410                 415
Pro Val Tyr Arg Ile Met Thr Gln Cys Trp Gln His Gln Pro Glu Asp
            420                 425                 430
Arg Pro Asn Phe Ala Ile Ile Leu Glu Arg Ile Glu Tyr Cys Thr Gln
        435                 440                 445
Asp Pro Asp Val Ile Asn Thr Ala Leu Pro Ile Glu Tyr Gly Pro Leu
    450                 455                 460
Val Glu Glu Glu Glu Lys Val Pro Val Arg Pro Lys Asp Pro Glu Gly
465                 470                 475                 480
Val Pro Pro Leu Leu Val Ser Gln Gln Ala Lys Arg Glu Glu Glu Arg
                485                 490                 495
```

-continued

```
Ser Pro Ala Ala Pro Pro Leu Pro Thr Thr Ser Ser Gly Lys Ala
            500                 505                 510

Ala Lys Lys Pro Thr Ala Ala Glu Val Ser Val Arg Val Pro Arg Gly
        515                 520                 525

Pro Ala Val Glu Gly Gly His Val Asn Met Ala Phe Ser Gln Ser Asn
    530                 535                 540

Pro Pro Ser Glu Leu His Lys Val His Gly Ser Arg Asn Lys Pro Thr
545                 550                 555                 560

Ser Leu Trp Asn Pro Thr Tyr Gly Ser Trp Phe Thr Glu Lys Pro Thr
                565                 570                 575

Lys Lys Asn Asn Pro Ile Ala Lys Lys Glu Pro His Asp Arg Gly Asn
            580                 585                 590

Leu Gly Leu Glu Gly Ser Cys Thr Val Pro Pro Asn Val Ala Thr Gly
        595                 600                 605

Arg Leu Pro Gly Ala Ser Leu Leu Glu Pro Ser Ser Leu Thr Ala
    610                 615                 620

Asn Met Lys Glu Val Pro Leu Phe Arg Leu Arg His Phe Pro Cys Gly
625                 630                 635                 640

Asn Val Asn Tyr Gly Tyr Gln Gln Gln Gly Leu Pro Leu Glu Ala Ala
                645                 650                 655

Thr Ala Pro Gly Ala Gly His Tyr Glu Asp Thr Ile Leu Lys Ser Lys
            660                 665                 670

Asn Ser Met Asn Gln Pro Gly Pro
675                 680
```

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
agcgatgcag atggaattgc agag                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
caataggcag cgccgtgttg atta                                          24

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
ggttcatcct gatggagctc atg                                           23

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct

```
<400> SEQUENCE: 10 cgggggggaga cctcaagtcc ttcctcc                                              27

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
gttcatcctg atggagctca tgg                                                   23

<210> SEQ ID NO 12
<211> LENGTH: 27
<212> TYPE: DNA
<213> ORGANISM: Artificial Sequence
<220> FEATURE:
<223> OTHER INFORMATION: Synthetic Construct

<400> SEQUENCE: 12 gggggggagac ctcaagtcct tcctccg                                              27

<210> SEQ ID NO 13
<211> LENGTH: 23
<212> TYPE: DNA
<213> ORGANISM: Artificial Sequence
<220> FEATURE:
<223> OTHER INFORMATION: Synthetic Construct

<400> SEQUENCE: 13
ttcatcctga tggagctcat ggc                                                   23

<210> SEQ ID NO 14
<211> LENGTH: 27
<212> TYPE: DNA
<213> ORGANISM: Artificial Sequence
<220> FEATURE:
<223> OTHER INFORMATION: Synthetic Construct

<400> SEQUENCE: 14
gggggagacc tcaagtcctt cctccga                                               27

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
cggttcatcc tgatggagct cat                                                   23

<210> SEQ ID NO 16
<211> LENGTH: 27
<212> TYPE: DNA
<213> ORGANISM: Artificial Sequence
<220> FEATURE:
<223> OTHER INFORMATION: Synthetic Construct

<400> SEQUENCE: 16
gcggggggag acctcaagtc cttcctc                                               27

<210> SEQ ID NO 17
```

```
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
ccggttcatc ctgatggagc tca                                              23

<210> SEQ ID NO 18
<211> LENGTH: 27
<212> TYPE: DNA
<213> ORGANISM: Artificial Sequence
<220> FEATURE:
<223> OTHER INFORMATION: Synthetic Construct

<400> SEQUENCE: 18 ggcggggga gacctcaagt ccttcct                                           27

<210> SEQ ID NO 19
<211> LENGTH: 23
<212> TYPE: DNA
<213> ORGANISM: Artificial Sequence
<220> FEATURE:
<223> OTHER INFORMATION: Synthetic Construct

<400> SEQUENCE: 19
ggttcatcct gatggagctc atg                                              23

<210> SEQ ID NO 20
<211> LENGTH: 27
<212> TYPE: DNA
<213> ORGANISM: Artificial Sequence
<220> FEATURE:
<223> OTHER INFORMATION: Synthetic Construct

<400> SEQUENCE: 20 gggggagac ctcaagtcct tcctccg                                           27

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
cggttcatcc tgatggagct cat                                              23

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct

<400> SEQUENCE: 22
cggggggaga cctcaagtcc ttcctcc                                          27
```

METHODS FOR INHIBITING CELL PROLIFERATION IN ALK-DRIVEN CANCERS

CROSS-REFERENCE TO RELATED APPLICATIONS

This application claims benefit from U.S. Provisional Application No. 61/810,554, filed Apr. 10, 2013.

BACKGROUND OF THE INVENTION

The present invention relates to methods, kits, and pharmaceutical compositions for inhibiting the proliferation of cells.

Anaplastic lymphoma kinase (ALK), a receptor tyrosine kinase in the insulin receptor superfamily, was first identified as a chromosomal rearrangement (NPM-ALK fusion gene) in anaplastic large cell lymphoma (ALCL) (Morris et al., Science 263:1281 (1994)). Alternate EML4-ALK gene translocations have been detected in a subset of non-small cell lung cancers (NSCLC), translocations with over a dozen other fusion partners have been observed, and single point mutations in ALK have been identified in a subset of neuroblastomas (Soda et al., Nature 448:561 (2007); Mossé et al., Nature 455:930 (2008); Janoueix-Lerosey et al., Nature 455:967 (2008); George et al., Nature 455:975 (2008); Webb et al., Expert Rev. Anticancer Ther. 9:331 (2009); and Chen et al., Nature 455:930 (2008)). Whereas expression of ALK is limited in normal adult human tissues, genetic studies indicate that aberrant expression of ALK or ALK fusions is a key driver in various tumor types, which highlights ALK as an important target in treating human tumors. The high sequence homology of ALK with other members of the insulin receptor superfamily presents a significant challenge in the design of ALK-selective inhibitors.

Other challenges to developing a successful therapy based on inhibiting a kinase like ALK include the existence or development of compensatory biological mechanisms, such as alternative signaling pathways that bypass or supercede ALK, ALK gene amplification or overexpression, increased drug efflux, or the development of mutations which impair binding of an inhibitor to ALK. If such mutations occur, it would be important to learn of their existence, be able to identify them in patients, identify effective inhibitors for such mutants, and treat a patient who has such a mutation with an inhibitor to target that mutant.

New diagnostic methods and therapies are needed for the detection and treatment of ALK-driven cancers, especially for those in which ALK mutations confer resistance to inhibitors of "wild-type" ALK kinases.

SUMMARY OF THE INVENTION

The invention involves the discovery of new mutations in ALK, including mutations which are of potentially profound medical significance because they confer resistance to one or more of CH5424802, ASP3026 and crizotinib (also known as PF1066, and herein as "compound 2", recently approved for the treatment of NSCLC). The invention further involves the discovery that compounds of formula (I), such as compound 1, disclosed in detail below, potently inhibit ALK as well as ALK mutants that are resistant to one or more of crizotinib, CH5424802 and ASP3026.

The invention thus provides a method for treating patients who have an ALK-driven cancer which is refractory or resistant to one or more of crizotinib, CH5424802 and ASP3026; who are intolerant to one or more of crizotinib, CH5424802 and ASP3026; or whose cancer is characterized by cells containing at least one of the ALK mutations disclosed herein, in each case, by administering to the patient a treatment-effective amount of a compound of formula (I) or a pharmaceutically acceptable salt thereof. The invention also features a method for characterizing ALK-driven cancers to determine whether the cancer cells contain an ALK gene bearing a given mutation and for identifying cells expressing ALK mutants.

The discoveries underlying this invention also represent the first identification of mutations in the ALK kinase domain present in ALK fusions, which are of increasing medical interest for their role in a variety of devastating cancers.

More specifically, the invention features inter alia a method of characterizing an ALK-driven cancer in a subject by identifying the presence of a mutation in anaplastic lymphoma kinase (ALK) in a sample obtained from the subject, where the mutation encodes an amino acid substitution at a position corresponding to one of the following amino acid positions in SEQ ID NO: 2: (i) threonine at amino acid position 1151; (ii) leucine at amino acid position 1152; (iii) cysteine at amino acid position 1156; (iv) isoleucine at amino acid position 1171; (v) phenylalanine at amino acid position 1174; (vi) valine at amino acid position 1180; (vii) arginine at amino acid position 1181; (viii) leucine at amino acid position 1196; (ix) leucine at amino acid position 1198; (x) glycine at amino acid position 1202; (xi) serine at amino acid position 1206; (xii) glutamic acid at amino acid position 1210; (xiii) glutamic acid at amino acid position 1241; (xiv) isoleucine at amino acid position 1268; and (xv) glycine at amino acid position 1269.

For example, in certain cases, the mutation encodes serine, threonine, or histidine in place of isoleucine at amino acid position 1171; serine in place of phenylalanine at amino acid position 1174; or glutamine in place of leucine at amino acid position 1196.

In certain embodiments, the mutation encodes lysine in place of threonine at amino acid position 1151; valine in place of leucine at amino acid position 1152; tyrosine in place of cysteine at amino acid position 1156; leucine or methionine in place of valine at amino acid position 1180; glycine in place of arginine at amino acid position 1181; methionine in place of leucine at amino acid position 1198; serine in place of glycine at amino acid position 1202; arginine, isoleucine, glycine, or alanine in place of serine at amino acid position 1206; lysine in place of glutamic acid at amino acid position 1210; lysine in place of glutamic acid at amino acid position 1241; valine in place of isoleucine at amino acid position 1268; or cysteine, serine, or alanine in place of glycine at amino acid position 1269.

In particular embodiments, the ALK is full-length ALK or an ALK-fusion product. In another embodiment, the one or more mutations are identified in an ALK protein or an ALK-fusion protein.

The invention also features a method of characterizing an ALK-driven cancer expressing an ALK-fusion protein in a subject including identifying the presence of a mutation in the ALK-fusion protein in a sample from the subject, where the mutation is selected from mutations corresponding to the amino acid positions in SEQ ID NO: 2 for: (i) a substitution for isoleucine with asparagine at amino acid position 1171; (ii) a substitution for phenylalanine with isoleucine, leucine, cysteine, or valine at amino acid position 1174; (iii) a substitution for phenylalanine with isoleucine, cysteine, or valine at amino acid position 1245; and (iv) a substitution for tyrosine with serine at amino acid position 1278. In one particular embodiment, the ALK-fusion protein is EML4-ALK.

The invention further features a method of characterizing an ALK-driven cancer expressing EML4-ALK fusion protein in a subject including identifying the presence of a mutation in the EML4-ALK fusion protein in a sample from the subject, where the mutation corresponds to a substitution for leucine with methionine at amino acid position 1196 of SEQ ID NO: 2.

In one embodiment of any of the methods described herein, the presence of the mutation in the sample indicates that the subject has or is at increased risk for developing an ALK-driven cancer. In other embodiments, the presence of the mutation in the sample indicates that the subject has or is at increased risk for developing an ALK-driven cancer refractory to treatment with a tyrosine kinase inhibitor. In particular embodiments, the presence of the mutation in the sample indicates that the subject has or is at increased risk for developing an ALK-driven cancer refractory to treatment with to one or more of crizotinib, CH5424802 and ASP3026. In yet other embodiments, where the ALK protein or ALK-fusion protein includes a contiguous sequence of between 30 and 1620 amino acids that is at least 95% identical to a corresponding sequence in SEQ ID NO: 2 or SEQ ID NO: 4.

In another embodiment of any of the methods described herein, the one or more mutations are identified by immunoblotting or by an ELISA assay. In certain embodiments, the one or more mutations are identified in a nucleic acid encoding the ALK. In other embodiments, the nucleic acid includes a contiguous sequence of between 60 and 6226 nucleotides that is at least 95% identical to a corresponding sequence in SEQ ID NO: 1 or SEQ ID NO: 3. In yet other embodiments, the nucleic acid is isolated prior to the identification of the one or more mutations in ALK. In particular embodiments, the nucleic acid is an mRNA. In further embodiments, the one or more mutations are identified by PCR, RT-PCR, quantitative real time PCR, allele-specific quantitative real time PCR, in situ hybridization, or single-strand conformational polymorphism.

In further embodiments of any of the methods described herein, the ALK-driven cancer is selected from anaplastic large cell lymphoma, non-small cell lung cancer, and neuroblastoma.

The invention also features a method for treating an ALK-driven cancer in a subject including the steps of: a) providing a subject having an ALK-driven cancer characterized by the presence of a mutation in anaplastic lymphoma kinase (ALK), where the mutation is selected from mutations corresponding to the amino acid positions in SEQ ID NO: 2 for: (i) a substitution for isoleucine to threonine at amino acid position 1171; (ii) a substitution for phenylalanine to cysteine at amino acid position 1174; (iii) a substitution for leucine to methionine at amino acid position 1196; (iv) a substitution for serine with arginine at amino acid position 1206; (v) a substitution for glutamic acid to lysine at amino acid position 1210; (vi) a substitution for phenylalanine to cysteine at amino acid position 1245; (vii) a substitution for glycine to serine at amino acid position 1269; and (viii) a substitution for valine to leucine at amino acid position 1180; and b) administering to the subject a therapeutically effective amount of compound of formula (I), or a pharmaceutically acceptable salt thereof. The compound of formula (I), or a pharmaceutically acceptable salt thereof, includes any compound of formula (I) as described herein. The mutation in ALK that can be treated includes any ALK mutant described herein. In one embodiment, the ALK is full-length ALK. In another embodiment, the ALK is an ALK-fusion product.

The invention further features a method for treating an ALK-driven cancer expressing an ALK-fusion protein in a subject including the steps of a) providing a subject having an ALK-driven cancer characterized by the presence of a mutation in the ALK-fusion protein, where the mutation is selected from mutations corresponding to the amino acid positions in SEQ ID NO: 2 for: (i) a substitution for phenylalanine with valine at amino acid position 1174; and (ii) a substitution for tyrosine with serine at amino acid position 1278; and b) administering to the subject a therapeutically effective amount of compound of formula (I), or a pharmaceutically acceptable salt thereof. The compound of formula (I), or a pharmaceutically acceptable salt thereof, includes any compound of formula (I) as described herein. In one embodiment, the ALK-fusion protein is EML4-ALK.

In particular embodiments of any of the methods described herein, such as the method of treating an ALK-driven cancer, the ALK protein or ALK-fusion protein includes a contiguous sequence of between 30 and 1620 amino acids that is at least 95% identical to a corresponding sequence in SEQ ID NO: 2 or SEQ ID NO: 4. In other embodiments, the ALK-driven cancer is selected from anaplastic large cell lymphoma, non-small cell lung cancer, and neuroblastoma. In further embodiments, the method further includes administering to the subject a first agent selected from one or more of crizotinib, CH5424802 and ASP3026, or a pharmaceutically acceptable salt thereof, within 6 days of administering the compound of formula (I), where each of the compound of formula (I) and the first agent are administered in an amount that together is sufficient to treat the ALK-driven cancer. The compound of formula (I), or a pharmaceutically acceptable salt thereof, includes any compound of formula (I) as described herein.

The invention also features a method of inhibiting the proliferation of a cell expressing an ALK mutant, where the ALK mutant is characterized by the presence of a mutation in anaplastic lymphoma kinase (ALK) selected from mutations corresponding to the amino acid positions in SEQ ID NO: 2 for: (i) a substitution for threonine to lysine at amino acid position 1151; (ii) a substitution for leucine to valine at amino acid position 1152; (iii) a substitution for cysteine to tyrosine at amino acid position 1156; (iv) a substitution for isoleucine with serine at amino acid position 1171; and (v) a substitution for glycine to cysteine, serine, or alanine at amino acid position 1269, the method including contacting the cell with a compound of formula (I), or a pharmaceutically acceptable salt thereof, in an amount sufficient to inhibit the proliferation. The compound of formula (I), or a pharmaceutically acceptable salt thereof, includes any compound of formula (I) as described herein. The ALK mutant characterized by the presence of a mutation in anaplastic lymphoma kinase (ALK) can include any ALK mutant described herein.

The invention further features a method of inhibiting the proliferation of a cell expressing a mutant ALK-fusion protein, where the mutant ALK-fusion protein is characterized by the presence of a mutation in the ALK-fusion protein selected from mutations corresponding to the amino acid positions in SEQ ID NO: 2 for: (i) a substitution for phenylalanine with valine at amino acid position 1174; and (ii) a substitution for tyrosine with serine at amino acid position 1278, the method including contacting the cell with a compound of formula (I), or a pharmaceutically acceptable salt thereof, in an amount sufficient to inhibit the proliferation. The compound of formula (I), or a pharmaceutically acceptable salt thereof, includes any compound of formula (I) as described herein. The mutant ALK-fusion protein that can be characterized by the presence of a mutation in the ALK-fusion protein can be any ALK mutant or ALK-fusion protein described herein. In one particular embodiment, the ALK-fusion protein is EML4-ALK.

In particular embodiments of any of the methods described herein, the cells are cancer cells. In certain embodiments, the cancer is a neuroblastoma, a glioblastoma, a soft tissue tumor, an ALK expressing lymphoma, an ALK expressing lung, breast, colon, or prostate carcinoma.

The invention also features method of treating an ALK-driven cancer refractory to one or more of crizotinib, CH5424802 and ASP3026 in a subject, the method including administering to the subject an ALK inhibitor of an ALK mutant described herein. The method can include the step of identifying an ALK mutation in the ALK-driven cancer.

The invention also features method of treating an ALK-driven cancer refractory to one or more of crizotinib, CH5424802 and ASP3026 in a subject, the method including administering to the subject a compound of formula I, or a pharmaceutically acceptable salt thereof, in an amount sufficient to treat the cancer. The compound of formula (I), or a pharmaceutically acceptable salt thereof, includes any compound of formula (I) as described herein.

The invention features a method of treating an ALK-driven cancer in a subject intolerant to one or more of crizotinib, CH5424802 and ASP3026, the method including administering to the subject a compound of formula I, or a pharmaceutically acceptable salt thereof, in an amount sufficient to treat the cancer.

The invention further features a method of treating an ALK-driven cancer refractory to an inhibitor of wild-type ALK in a subject, the method including administering to the subject a compound of formula I, or a pharmaceutically acceptable salt thereof, in an amount sufficient to treat the cancer.

In a related aspect the invention features a method for treating an ALK-driven cancer in a subject including the steps of (a) providing a subject having an ALK-driven cancer characterized by the presence of a mutation in anaplastic lymphoma kinase (ALK), and (b) administering to the subject a therapeutically effective amount of compound of compound 1, or a pharmaceutically acceptable salt thereof. In particular embodiments the ALK is full-length ALK. In still other embodiments, the ALK is an ALK-fusion product. The mutation can be selected from mutations corresponding to the amino acid positions in SEQ ID NO: 2 for: (i) a substitution for threonine at amino acid position 1151; (ii) a substitution for leucine at amino acid position 1152; (iii) a substitution for cysteine at amino acid position 1156; (iv) a substitution for isoleucine at amino acid position 1171; (v) a substitution for phenylalanine at amino acid position 1174; (vi) a substitution for valine at amino acid position 1180; (vii) a substitution for arginine at amino acid position 1181; (viii) a substitution for leucine at amino acid position 1196; (ix) a substitution for leucine at amino acid position 1198; (x) a substitution for glycine at amino acid position 1202; (xi) a substitution for aspartic acid at amino acid position 1203; (xii) a substitution for serine at amino acid position 1206; (xiii) a substitution for glutamic acid at amino acid position 1210; (xiv) a substitution for glutamic acid at amino acid position 1241; (xv) a substitution for phenylalanine at amino acid position 1245; (xvi) a substitution for isoleucine at amino acid position 1268; (xvii) a substitution for glycine at amino acid position 1269; and (xviii) insertion of an amino acid following amino acid position 1151. In particular embodiments, the mutation is selected from mutations corresponding to the amino acid positions in SEQ ID NO: 2 for: (i) a substitution for leucine to arginine at amino acid position 1152; (ii) a substitution for cysteine to tyrosine at amino acid position 1156; (iii) a substitution for isoleucine to serine at amino acid position 1171; (iv) a substitution for isoleucine to asparagine at amino acid position 1171; (v) a substitution for isoleucine to threonine at amino acid position 1171; (vi) a substitution for phenylalanine to leucine at amino acid position 1174; (vii) a substitution for phenylalanine to cysteine at amino acid position 1174; (viii) a substitution for valine to leucine at amino acid position 1180; (ix) a substitution for leucine to methionine at amino acid position 1196; (x) a substitution for glycine to arginine at amino acid position 1202; (xi) a substitution for aspartic acid to asparagine at amino acid position 1203; (xii) a substitution for serine to tyrosine at amino acid position 1206; (xiii) a substitution for serine with arginine at amino acid position 1206; (xiv) a substitution for glutamic acid to lysine at amino acid position 1210; (xv) a substitution for phenylalanine to cysteine at amino acid position 1245; (xvi) a substitution for glycine to alanine at amino acid position 1269; (xvii) a substitution for glycine to serine at amino acid position 1269; and (xviii) insertion of threonine following position 1151 (T1151T insertion).

The invention also features a method for treating an ALK-driven cancer in a subject including the steps of: a) providing a subject having an ALK-driven cancer characterized by the presence of a mutation in anaplastic lymphoma kinase (ALK), wherein the mutation is selected from mutations corresponding to the amino acid positions in SEQ ID NO: 2 for: ((i) a substitution for leucine to arginine at amino acid position 1152; (ii) a substitution for cysteine to tyrosine at amino acid position 1156; (iii) a substitution for isoleucine to serine at amino acid position 1171; (iv) a substitution for isoleucine to asparagine at amino acid position 1171; (v) a substitution for isoleucine to threonine at amino acid position 1171; (vi) a substitution for phenylalanine to leucine at amino acid position 1174; (vii) a substitution for phenylalanine to cysteine at amino acid position 1174; (viii) a substitution for valine to leucine at amino acid position 1180; (ix) a substitution for leucine to methionine at amino acid position 1196; (x) a substitution for aspartic acid to asparagine at amino acid position 1203; (xi) a substitution for serine with arginine at amino acid position 1206; (xii) a substitution for glutamic acid to lysine at amino acid position 1210; (xiii) a substitution for phenylalanine to cysteine at amino acid position 1245; (xiv) a substitution for glycine to alanine at amino acid position 1269; and (xv) a substitution for glycine to serine at amino acid position 1269; and b) administering to the subject a therapeutically effective amount of compound of formula I, or a pharmaceutically acceptable salt thereof. In particular embodiments the ALK is full-length ALK. In still other embodiments, the ALK is an ALK-fusion product.

The invention features an isolated probe including 8 to 50 nucleotides that hybridizes a contiguous sequence of nucleotides within a nucleic acid encoding an ALK or ALK-fusion protein that contains the sequence of one or more codons corresponding to the following codons: nucleotides 4362 to 4364 of SEQ ID NO: 1 (e.g., AAA or AAG); nucleotides 3599-3601 of SEQ ID NO: 3 (e.g., AAA or AAG); nucleotides 4365 to 4367 of SEQ ID NO: 1 (e.g., GTT, GTC, GTA, or GTG); nucleotides 3602 to 3604 of SEQ ID NO: 3 (e.g., GTT, GTC, GTA, or GTG); nucleotides 4377 to 4379 of SEQ ID NO: 1 (e.g., TAT or TAC); nucleotides 3614 to 3616 of SEQ ID NO: 3 (e.g., TAT or TAC); nucleotides 4422 to 4424 of SEQ ID NO: 1 (e.g., TCT, TCC, TCA, TCG, AGT, AGC, ACT, ACC, ACA, ACG, CAT, or CAC); nucleotides 3659 to 3661 of SEQ ID NO: 3 (e.g., TCT, TCC, TCA, TCG, AGT, AGC, ACT, ACC, ACA, ACG, CAT, or CAC); nucleotides 4431 to 4433 of SEQ ID NO: 1 (e.g., TCT, TCC, TCA, TCG, AGT, or AGC); nucleotides 3668 to 3670 of SEQ ID NO: 3 (e.g., TCT, TCC, TCA, TCG, AGT, or AGC); nucleotides 4449 to 4451 of SEQ ID NO: 1 (e.g., ATG); nucleotides 3686 to 3688 of SEQ ID NO: 3 (e.g., ATG); nucleotides 4452 to 4454 of SEQ ID NO: 1 (e.g., GGT, GGC, GGA, or GGG); nucleotides 3689 to 3691 of SEQ ID NO: 3 (e.g., GGT, GGC, GGA, or GGG); nucleotides 4497 to 4499 of SEQ ID NO: 1 (e.g., CAA or CAG); nucleotides 3734-3736 of SEQ ID NO: 3 (e.g., CAA or CAG); nucleotides 4503 to 4505 of SEQ ID NO: 1 (e.g., ATG); nucleotides 3740 to 3742 of SEQ ID NO: 3 (e.g., ATG); nucleotides 4515 to 4517 of SEQ ID NO: 1 (e.g, TCT, TCC, TCA, TCG, AGT, or AGC); nucleotides 3752 to 3754 of SEQ ID NO: 3 (e.g, TCT, TCC, TCA, TCG, AGT, or AGC); nucleotides 4527 to 4529 of SEQ ID NO: 1 (e.g., GGT, GGC, GGA, GGG, ATT, ATC, ATA, AGA, AGG, GCT, GCC, GCA, or GCG); nucleotides 3764 to 3766 of SEQ ID NO: 3 (e.g., GGT, GGC, GGA, GGG, ATT, ATC, ATA, AGA, AGG, GCT, GCC, GCA, or GCG); nucleotides 4539 to 4541 of SEQ ID NO: 1 (e.g., AAA or AAG); nucleotides 3776 to 3778 of SEQ ID NO: 3 (e.g., AAA or AAG); nucleotides 4632-4634 of SEQ ID NO: 1 (e.g., AAA or AAG); nucleotides 3869 to 3871 of SEQ ID NO: 3 (e.g., AAA or AAG); nucleotides 4713 to 4715 of SEQ ID NO: 1 (e.g., GTT, GTC, GTA, or GTG); nucleotides 3950 to 3952 of SEQ ID NO: 3 (e.g., GTT, GTC, GTA, or GTG); nucleotides 4716 to 4718 of SEQ ID NO: 1 (e.g, TGT, TGC, TCT, TCC, TCA, TCG, AGT, or AGC); and nucleotides 3953-3955 of SEQ ID NO: 3 (e.g, TGT, TGC, TCT, TCC, TCA, TCG, AGT, or AGC); or a complementary sequence thereof.

In particular embodiments, the probe further includes one or more ligands or labels. In one embodiment, the ligand or label is covalently attached to the 5' or 3' terminus of the probe. In another embodiment, ligand is biotin or digoxigenin. In yet another embodiment, the label is detectable by fluorescence, radioactivity, UV/visible light absorption, X-ray diffraction or absorption, magnetism, or enzymatic activity.

In certain embodiments, the label is a fluorophore (e.g., (5-dimethylamino)-1naphthalenesulfonyl; N-oxyl-4,4-dimethyloxazolidine; N-oxyl-2,2,5,5-tetramethylpyrrolidone, N-oxyl-2,2,6,6-tetramethylpiperidine, dinitrophenyl, acridines, coumarins, fluoresein, Cy3, or Cy5). In one embodiment, the fluorophore is covalently attached to one terminus of the probe and a quencher is covalently attached to the other terminus of the probe.

In some embodiments, the probe includes a sequence selected from the group of: ggttcatcctgatggagctcatg (SEQ ID NO: 9); gttcatcctgatggagctcatgg (SEQ ID NO: 11); ttcatcctgatggagctcatggc (SEQ ID NO: 13); cggttcatcctgatggagctcat (SEQ ID NO: 15); ccggttcatcctgatggagctca (SEQ ID NO: 17); ggttcatcctgatggagctcatg (SEQ ID NO: 19); and cggtcatcctgatggagctcat (SEQ ID NO: 21).

The invention also features a kit including: i) one or more probes described herein; and ii) instructions for the use of the probe in the identification of a mutation in a nucleic acid encoding an ALK protein or an ALK-fusion protein.

The invention features a composition including: i) a first isolated probe including 8 to 50 nucleotides, including a sequence that hybridizes a contiguous sequence of nucleotides within a nucleic acid encoding an ALK or ALK-fusion protein that contains the sequence of one or more codons corresponding to the following codons: nucleotides 4362 to 4364 of SEQ ID NO: 1 (e.g., AAA or AAG); nucleotides 3599-3601 of SEQ ID NO: 3 (e.g., AAA or AAG); nucleotides 4365 to 4367 of SEQ ID NO: 1 (e.g., GTT, GTC, GTA, or GTG); nucleotides 3602 to 3604 of SEQ ID NO: 3 (e.g., GTT, GTC, GTA, or GTG); nucleotides 4377 to 4379 of SEQ ID NO: 1 (e.g., TAT or TAC); nucleotides 3614 to 3616 of SEQ ID NO: 3 (e.g., TAT or TAC); nucleotides 4422 to 4424 of SEQ ID NO: 1 (e.g., TCT, TCC, TCA, TCG, AGT, AGC, ACT, ACC, ACA, ACG, CAT, or CAC); nucleotides 3659 to 3661 of SEQ ID NO: 3 (e.g., TCT, TCC, TCA, TCG, AGT, AGC, ACT, ACC, ACA, ACG, CAT, or CAC); nucleotides 4431 to 4433 of SEQ ID NO: 1 (e.g., TCT, TCC, TCA, TCG, AGT, or AGC); nucleotides 3668 to 3670 of SEQ ID NO: 3 (e.g., TCT, TCC, TCA, TCG, AGT, or AGC); nucleotides 4449 to 4451 of SEQ ID NO: 1 (e.g., ATG); nucleotides 3686 to 3688 of SEQ ID NO: 3 (e.g., ATG); nucleotides 4452 to 4454 of SEQ ID NO: 1 (e.g., GGT, GGC, GGA, or GGG); nucleotides 3689 to 3691 of SEQ ID NO: 3 (e.g., GGT, GGC, GGA, or GGG); nucleotides 4497 to 4499 of SEQ ID NO: 1 (e.g., CAA or CAG); nucleotides 3734-3736 of SEQ ID NO: 3 (e.g., CAA or CAG); nucleotides 4503 to 4505 of SEQ ID NO: 1 (e.g., ATG); nucleotides 3740 to 3742 of SEQ ID NO: 3 (e.g., ATG); nucleotides 4515 to 4517 of SEQ ID NO: 1 (e.g., TCT, TCC, TCA, TCG, AGT, or AGC); nucleotides 3752 to 3754 of SEQ ID NO: 3 (e.g., TCT, TCC, TCA, TCG, AGT, or AGC); nucleotides 4527 to 4529 of SEQ ID NO: 1 (e.g., GGT, GGC, GGA, GGG, ATT, ATC, ATA, AGA, AGG, GCT, GCC, GCA, or GCG); nucleotides 3764 to 3766 of SEQ ID NO: 3 (e.g., GGT, GGC, GGA, GGG, ATT, ATC, ATA, AGA, AGG, GCT, GCC, GCA, or GCG); nucleotides 4539 to 4541 of SEQ ID NO: 1 (e.g., AAA or AAG); nucleotides 3776 to 3778 of SEQ ID NO: 3 (e.g., AAA or AAG); nucleotides 4632-4634 of SEQ ID NO: 1 (e.g., AAA or AAG); nucleotides 3869 to 3871 of SEQ ID NO: 3 (e.g., AAA or AAG); nucleotides 4713 to 4715 of SEQ ID NO: 1 (e.g., GTT, GTC, GTA, or GTG); nucleotides 3950 to 3952 of SEQ ID NO: 3 (e.g., GTT, GTC, GTA, or GTG); nucleotides 4716 to 4718 of SEQ ID NO: 1 (e.g., TGT, TGC, TCT, TCC, TCA, TCG, AGT, or AGC); and nucleotides 3953-3955 of SEQ ID NO: 3 (e.g., TGT, TGC, TCT, TCC, TCA, TCG, AGT, or AGC), or a complementary sequence thereof; and further including a first fluorophore; and ii) a second isolated probe including 8 to 50 nucleotides, including a sequence that is at least 95% identical to a corresponding contiguous nucleic acid sequence in SEQ ID NO: 1 or SEQ ID NO: 3, or a complementary sequence thereof, where the second probe hybridizes to a different contiguous nucleic acid sequence within the nucleic acid encoding an ALK or ALK-fusion protein than the first isolated probe, and where the second probe includes a second fluorophore.

In some embodiments, the first fluorophore includes an acceptor fluorophore and the second fluorophore includes a donor fluorophore. In a further embodiment, (1) the acceptor fluorophore is attached to a 3' end of the first probe and the donor fluorophore is attached to the 5' end of the second probe, or (2) the acceptor fluorophore is attached to the 5' end of the first probe and the donor fluorophore is attached to the 3' end of the second probe.

In other embodiments, the first probe and the second probe are selected from the following pairs: ggttcatcctgatggagctcatg (SEQ ID NO: 9)/cgggggagacctcaagtccttcctcc (SEQ ID NO: 10); gttcatcctgatggagctcatgg (SEQ ID NO: 11)/gggggagacctcaagtccttcctccg (SEQ ID NO: 12); ttcatcctgatggagctcatggc (SEQ ID NO: 13)/gggggagacctcaagtcct-tcctccga (SEQ ID NO: 14); cggttcatcctgatggagctcat (SEQ ID NO: 15)/gcgggggagacctcaagtccttcctc (SEQ ID NO: 16); ccggttcatcctgatggagctca (SEQ ID NO: 17)/ggcgggggagac-ctcaagtccttcct (SEQ ID NO: 18); ggttcatcctgatggagctcatg (SEQ ID NO: 19)/gggggagacctcaagtccttcctccg (SEQ ID NO: 20); and cggttcatcctgatggagctcat (SEQ ID NO: 21)/cgggggagacctcaagtccttcctcc (SEQ ID NO: 22).

The invention also features a kit including: i) a first isolated probe including 8 to 50 nucleotides, including a sequence that hybridizes a contiguous sequence of nucleotides within a nucleic acid encoding an ALK or ALK-fusion protein that contains the sequence of one or more codons corresponding to the following codons: nucleotides 4362 to 4364 of SEQ ID NO: 1 (e.g., AAA or AAG); nucleotides 3599-3601 of SEQ ID NO: 3 (e.g., AAA or AAG); nucleotides 4365 to 4367 of SEQ ID NO: 1 (e.g., GTT, GTC, GTA, or GTG); nucleotides 3602 to 3604 of SEQ ID NO: 3 (e.g., GTT, GTC, GTA, or GTG); nucleotides 4377 to 4379 of SEQ ID NO: 1 (e.g., TAT or TAC); nucleotides 3614 to 3616 of SEQ ID NO: 3 (e.g., TAT or TAC); nucleotides 4422 to 4424 of SEQ ID NO: 1 (e.g., TCT, TCC, TCA, TCG, AGT, AGC, ACT, ACC, ACA, ACG, CAT, or CAC); nucleotides 3659 to 3661 of SEQ ID NO: 3 (e.g., TCT, TCC, TCA, TCG, AGT, AGC, ACT, ACC, ACA, ACG, CAT, or CAC); nucleotides 4431 to 4433 of SEQ ID NO: 1 (e.g., TCT, TCC, TCA, TCG, AGT, or AGC); nucleotides 3668 to 3670 of SEQ ID NO: 3 (e.g., TCT, TCC, TCA, TCG, AGT, or AGC); nucleotides 4449 to 4451 of SEQ ID NO: 1 (e.g., ATG); nucleotides 3686 to 3688 of SEQ ID NO: 3 (e.g., ATG); nucleotides 4452 to 4454 of SEQ ID NO: 1 (e.g., GGT, GGC, GGA, or GGG); nucleotides 3689 to 3691 of SEQ ID NO: 3 (e.g., GGT, GGC, GGA, or GGG); nucleotides 4497 to 4499 of SEQ ID NO: 1 (e.g., CAA or CAG); nucleotides 3734-3736 of SEQ ID NO: 3 (e.g., CAA or CAG); nucleotides 4503 to 4505 of SEQ ID NO: 1 (e.g., ATG); nucleotides 3740 to 3742 of SEQ ID NO: 3 (e.g., ATG); nucleotides 4515 to 4517 of SEQ ID NO: 1 (e.g., TCT, TCC, TCA, TCG, AGT, or AGC); nucleotides 3752 to 3754 of SEQ ID NO: 3 (e.g., TCT, TCC, TCA, TCG, AGT, or AGC); nucleotides 4527 to 4529 of SEQ ID NO: 1 (e.g., GGT, GGC, GGA, GGG, ATT, ATC, ATA, AGA, AGG, GCT, GCC, GCA, or GCG); nucleotides 3764 to 3766 of SEQ ID NO: 3 (e.g., GGT, GGC, GGA, GGG, ATT, ATC, ATA, AGA, AGG, GCT, GCC, GCA, or GCG); nucleotides 4539 to 4541 of SEQ ID NO: 1 (e.g., AAA or AAG); nucleotides 3776 to 3778 of SEQ ID NO: 3 (e.g., AAA or AAG); nucleotides 4632-4634 of SEQ ID NO: 1 (e.g., AAA or AAG); nucleotides 3869 to 3871 of SEQ ID NO: 3 (e.g., AAA or AAG); nucleotides 4713 to 4715 of SEQ ID NO: 1 (e.g., GTT, GTC, GTA, or GTG); nucleotides 3950 to 3952 of SEQ ID NO: 3 (e.g., GTT, GTC, GTA, or GTG); nucleotides 4716 to 4718 of SEQ ID NO: 1 (e.g., TGT, TGC, TCT, TCC, TCA, TCG, AGT, or AGC); and nucleotides 3953-3955 of SEQ ID NO: 3 (e.g., TGT, TGC, TCT, TCC, TCA, TCG, AGT, or AGC), or a complementary sequence thereof; and further including a first fluorophore; ii) a second isolated probe including 8 to 50 nucleotides, including a sequence that is at least 95% identical to a corresponding contiguous nucleic acid sequence in SEQ ID NO: 1 or SEQ ID NO: 3, where the second probe hybridizes to a different contiguous nucleic acid sequence within the nucleic acid encoding an ALK or ALK-fusion protein than the first isolated probe, and where the second probe includes a second fluorophore; and iii) instructions for the use of the probe in the identification of a mutation in a nucleic acid encoding an ALK protein or an ALK-fusion protein.

In some embodiments, the first fluorophore includes an acceptor fluorophore and the second fluorophore includes a donor fluorophore. In a further embodiment, (1) the acceptor fluorophore is attached to a 3' end of the first probe and the donor fluorophore is attached to the 5' end of the second probe, or (2) the acceptor fluorophore is attached to the 5' end of the first probe and the donor fluorophore is attached to the 3' end of the second probe.

In other embodiments, the first probe and the second probe are selected from the following pairs: ggttcatcctgatg-gagctcatg (SEQ ID NO: 9)/cgggggagacctcaagtccttcctcc (SEQ ID NO: 10); gttcatcctgatggagctcatgg (SEQ ID NO: 11)/gggggagacctcaagtccttcctccg (SEQ ID NO: 10); ttcatc-ctgatggagctcatggc (SEQ ID NO: 13)/gggggagacctcaagtcct-tcctccga (SEQ ID NO: 14); cggttcatcctgatggagctcat (SEQ ID NO: 15)/gcgggggagacctcaagtccttcctc (SEQ ID NO: 16); ccggttcatcctgatggagctca (SEQ ID NO: 17)/ggcgggggagac-ctcaagtccttcct (SEQ ID NO: 18); ggttcatcctgatggagctcatg (SEQ ID NO: 19)/gggggagacctcaagtccttcctccg (SEQ ID NO: 20); and cggttcatcctgatggagctcat (SEQ ID NO: 21)/cgggggagacctcaagtccttcctcc (SEQ ID NO: 22).

In any of the above methods for inhibiting cell proliferation or treating a subject with an ALK-driven cancer, the compound of formula (I) is described by the formula:

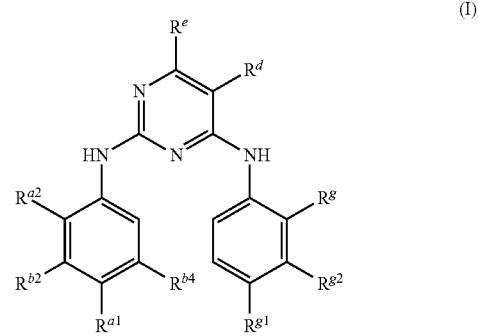

In formula (I), $R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two, or three heteroatoms, independently selected from N, S and O, wherein the 5- or 6-membered ring is substituted by $R^h$; $R^h$ is H, $C_{1-4}$ alkyl, or halo; $R^{a2}$ is H, $C_{1-6}$ alkoxy, $C_{3-6}$ alkenyloxy, or $C_{3-6}$ cycloalkyloxy; $R^g$ is —P(O)($R^{3A}$)($R^{3B}$), —S(O)N($R^{3C}$)($R^{3D}$), —S(O)$_2R^{3E}$, —OC(O)N($R^{3F}$)($R^{3G}$), —C(O)N($R^{3F}$)($R^{3G}$), —NR$^{3H}$C(O)OR$^{3I}$, a 5 or 6 member heterocyclic ring comprising 1, 2, 3 or 4 N atoms, or combined with $R^{g2}$ forms a 5- to 7-member heterocyclic ring; each of $R^{3A}$, $R^{3B}$, $R^{3C}$, $R^{3D}$, $R^{3E}$, $R^{3F}$, $R^{3G}$, $R^{3H}$, and $R^{3I}$ is, independently, selected from H, alkyl, alkenyl, alkynyl, cycloalkyl, cycloalkenyl, cycloalkynyl, and heteroalkyl, or $R^{3A}$ and $R^{3B}$, or $R^{3C}$ and $R^{3D}$, or $R^{3F}$ and $R^{3G}$, together with the atoms to which they are attached, combine to form a 5- or 6-membered heterocyclic ring which is unsubstituted or substituted; $R^{g2}$ is H, halo (e.g., F, Br, Cl, I), halo, CN, alkyl, alkenyl, alkynyl, cycloalkyl, cycloalkenyl, cycloalky-nyl, heteroalkyl, (e.g., $C_{1-6}$ alkyl, $C_{3-6}$ cycloalkyl, $C_{1-6}$ alkoxyl, $C_{3-6}$ cycloalkoxyl, $CF_3$) or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted; $R^{g1}$ is H, F, or a 5 or 6 member heterocyclic ring comprising 1 or 2 N atoms, the heterocyclic ring being unsubstituted or substituted; $R^{b2}$ is H, F, or is a 5 or 6 member heterocyclic ring containing 1, 2 or 3 N or O atoms, the heterocyclic ring being unsubstituted or substituted; $R^{b4}$ is H, halo (e.g., F, Br, Cl, I), halo, CN, alkyl, alkenyl, alkynyl, cycloalkyl, cycloalkenyl, cycloalkynyl, heteroalkyl, (e.g., $C_{1-6}$ alkyl, $C_{3-6}$ cycloalkyl, $C_{1-6}$ alkoxyl, $C_{3-6}$ cycloalkoxyl, $CF_3$), $C_{1-6}$ alkoxy, $C_{3-6}$ alkenyloxy, or $C_{3-6}$ cycloalkyloxy, —OC(O)N($R^{5A}$)($R^{5B}$), —$NR^{5C}$C(O)$OR^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted; each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted; $R^{a1}$ combines with $R^{b4}$ to form a 6 member heterocyclic ring, or is H, halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

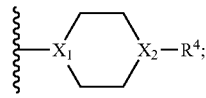

each Y is, independently, a bond, —O—, —S— or —$NR^1$—; each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl; each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl.

In formula (I), for any of $R^{a2}$, $R^d$, $R^h$, $R^1$, $R^2$, $R^4$, $R^{3A}$, $R^{3B}$, $R^{3C}$, $R^{3D}$, $R^{3E}$, $R^{3F}$, $R^{3G}$, $R^{3H}$, and $R^{3I}$ selected from $C_{1-6}$ alkoxy, $C_{3-6}$ alkenyloxy, $C_{3-6}$ cycloalkyloxy, alkyl, alkenyl, alkynyl, cycloalkyl, cycloalkenyl, cycloalkynyl, aryl, heteroalkyl, heterocyclic, and heteroaryl, the substituent is substituted or unsubstituted.

In particular embodiments, the compound of formula (I) is further described by formula (IIa) or formula (IIb):

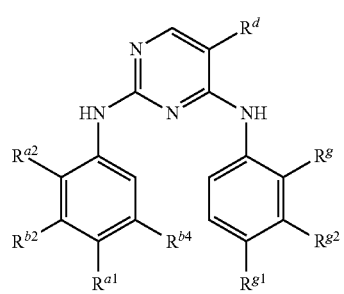

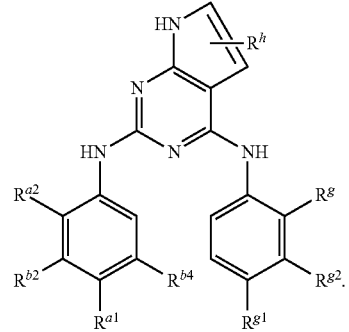

In formulas (IIa) and (IIb), $R^{a1}$; $R^{a2}$; $R^{b2}$; $R^{b4}$; $R^g$; $R^{g1}$; $R^{g2}$; $R^d$; and $R^h$ are as defined above.

In certain embodiments of the compounds of formula (I), (IIa), or (IIb), $R^{g1}$, $R^{g2}$, $R^{b2}$ and $R^{b4}$ are H or F.

In an embodiment of the compounds of formula (IIa), $R^d$ is Cl, F or $CF_3$.

In certain embodiments of the compounds of formula (I), (IIa), or (IIb), $R^{a1}$ is methoxy.

In one embodiment of the compounds of formula (I), (IIa), or (IIb), $R^g$ is —P(O)($R^{3A}$)($R^{3B}$) or —S(O)$_2R^{3E}$.

In another embodiment of the compounds of formula (I), (IIa), or (IIb), $R^{a1}$ is a 5 or 6 member heterocyclic ring comprising 1 or 2 N or O atoms which is unsubstituted or substituted with an alkyl group.

In some embodiments, the compound of formula (I) can further be described by formula (III):

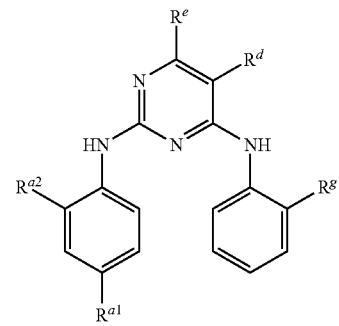

In formula (III), $R^{a2}$ is alkoxy; $R^g$ is —P(O)($R^{3A}$)($R^{3B}$); —S(O)N($R^{3C}$)($R^{3D}$); or —S(O)$_2R^{3E}$; each of $R^{3A}$, $R^{3B}$, $R^{3C}$, $R^{3D}$, and $R^{3E}$ is, independently, selected from H and $C_{1-7}$ alkyl, or $R^{3A}$ and $R^{3B}$, or $R^{3C}$ and $R^{3D}$, together with the atoms to which they are attached, combine to form a 5- or 6-membered heterocyclic ring which is unsubstituted or substituted; $R^d$ is H, $C_{1-4}$ alkyl, or halo; and $R^e$ is H; or $R^d$ and $R^e$, together with the pyrimidine ring atoms to which they are attached, form a 5- or 6-membered ring containing one or two heteroatoms, independently selected from N, S and O, wherein the 5- or 6-membered ring is substituted by $R^h$; $R^h$ is H, $C_{1-4}$ alkyl, or halo; $R^{a1}$ is halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

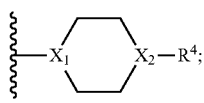

each Y is, independently, a bond, —O—, —S— or —NR¹—; each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl; each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl.

In particular embodiments, the compound of formula (III) is further described by formula (IVa) or formula (IVb):

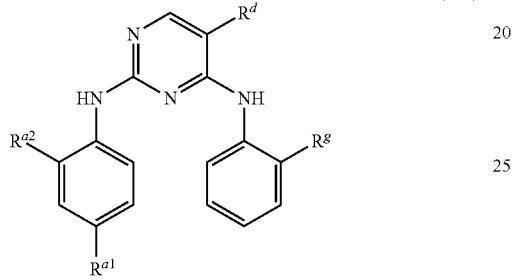
(IVa)

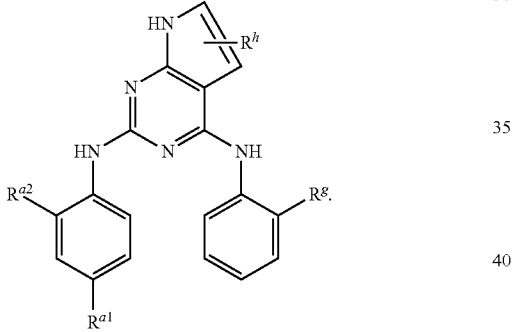
(IVb)

In formulas (IVa) and (IVb), $R^{a2}$; $R^g$; $R^d$; $R^h$; and $R^{a1}$ are as defined above for formula (III).

In certain embodiments of the compounds of any of formulas (III), (IVa) and (IVb), $R^{a2}$ is a methoxy, ethoxy, or propoxy group.

In some embodiments of the compounds of formula (III) and (IVa), $R^d$ is selected from Cl, F, CF$_3$, and cyclopropyl;

In still other embodiments, the compound of formula (III) is further described by any of formulas (Va)-(Vd):

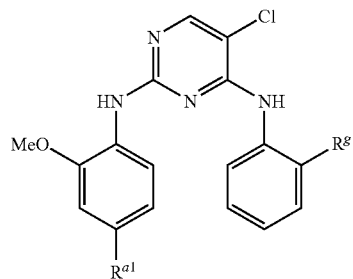
(Va)

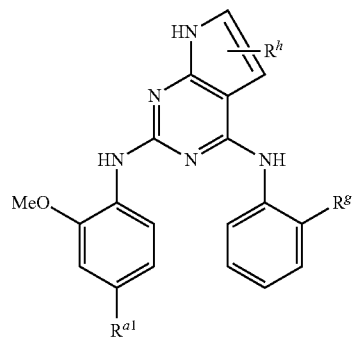
(Vb)

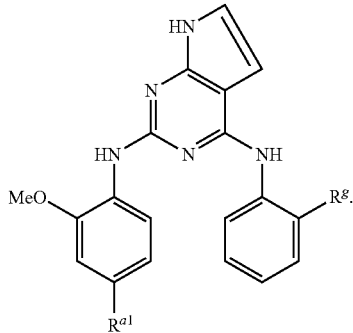
(Vc)

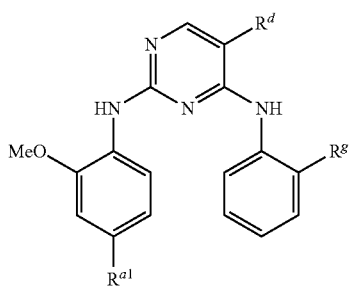
(Vd)

In formulas (Va)-(Vd), $R^g$; $R^d$; $R^h$; and $R^{a1}$ are as defined above for formula (III).

In particular embodiments of the compounds of any of the above formulas, $R^g$ is —P(O)(CH$_3$)$_2$ or —S(O)$_2$(CH(CH$_3$)$_2$).

In particular embodiments of the compounds of any of the above formulas, $R^{a1}$ is:

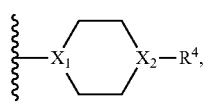

wherein $X_1$, $X_2$, and $R^4$ are as defined above for formula (III). For example, $R^{a1}$ can be selected from any of the following groups:

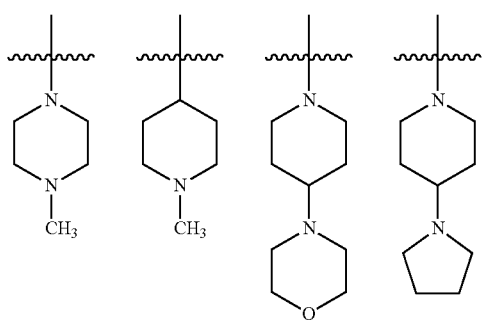
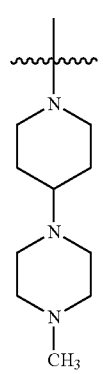
In particular embodiments, the compound of formula (I) is further described by one of formulas (VIa)-(VIf):
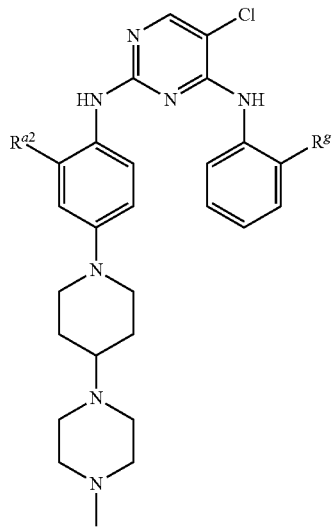
(VIa)
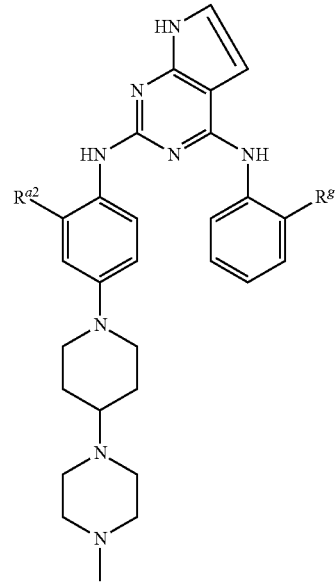
(VIb)
(VIc)
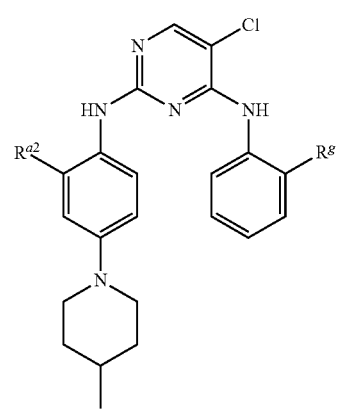
(VId)
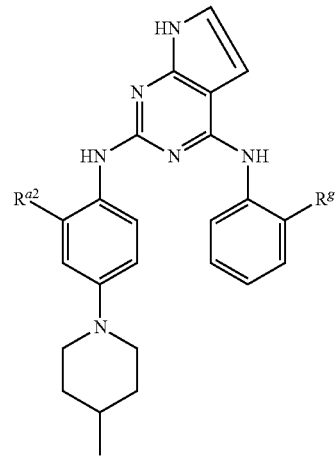

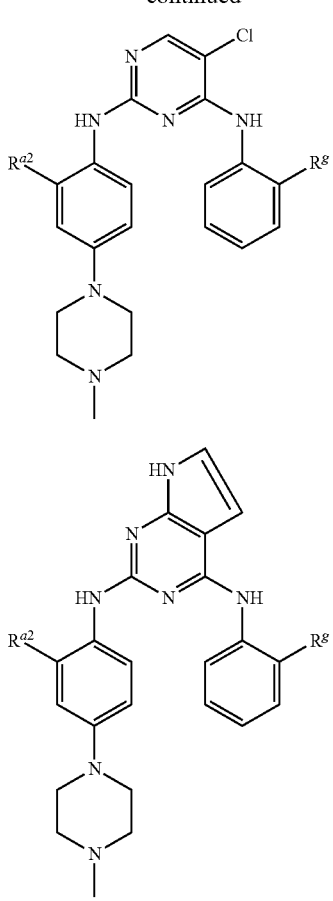

In formulas (VIa)-(VIf), $R^{a2}$ is a methoxy, ethoxy, or propoxy group; and $R^g$ is —P(O)(CH$_3$)$_2$ or —S(O)$_2$(CH(CH$_3$)$_2$).

In any of the above formulas, the compound can be either in its free base form, or a pharmaceutically acceptable salt.

The compounds of formula (I) include those described in PCT Publication Nos. WO2009/143389, WO 2006/021454, WO 2006/021457, and WO2009/126515, each of which is incorporated herein by reference.

The response criteria for the methods of the invention can be graded according to the response evaluation criteria in solid tumors (RECIST) guidelines (see Eur. J. Cancer 45:228 (2009)) that define when cancer patients improve ("respond"), stay the same ("stabilize"), or worsen ("progression") during treatments. A complete response is characterized by: (i) disappearance of all target lesions; and (ii) any pathological lymph nodes (whether target or non-target) must have reduction in short axis to <10 mm. A partial response is characterized by: (i) at least a 30% decrease in the sum of diameters of target lesions, taking as reference the baseline sum diameters. A progressive disease is characterized by (i) at least a 5%, 10%, or 20% increase in the sum of diameters of target lesions, taking as reference the smallest sum on study (this includes the baseline sum if that is the smallest on study); or (ii) the appearance of one or more new lesions.

By "acceptor fluorophore" is meant a compound which absorbs energy from a donor fluorophore (e.g., in the range of about 400 to 900 nm, such as in the range of about 500 to 800 nm). Acceptor fluorophores generally absorb energy at a wavelength that is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an extinction spectrum which overlaps with the emission of the donor fluorophore, such that energy emitted by the donor can excite the acceptor. Ideally, an acceptor fluorophore is capable of being attached to a nucleic acid molecule, such as an isolated probe or primer of the invention. Exemplary acceptor fluorophores include, but are not limited to, rhodamine and its derivatives (such as N, N, N', N'-tetramethyl-6-carboxyrhodamine (TAMRA) and 6-carboxy-X-rhodamine (ROX)), fluorescein derivatives (such as 5-carboxyfluorescein (FAM) and 2',7'-dimethoxy-4',5'-dichloro-6-carboxyfluorescein (JOE)), green fluorescent protein (GFP), BODIPY (4,4-difluoro-4-bora-3a,4a-diaza-s-indacene), LightCycler Red (LC-Red) 640, LC-Red 705, and cyanine dyes (such as Cy5 and Cy5.5). In particular examples, an acceptor fluorophore is capable of being attached to a nucleotide, such as the base, sugar, or phosphate ($\alpha$, $\beta$, or $\gamma$) of the nucleotide. For example, an acceptor fluorophore can be attached to a nucleotide that is part of a probe disclosed herein, such as the 3'- or 5'-end of the probe. In a particular example, an acceptor fluorophore is a dark quencher, such as Dabcyl, QSY7 (Molecular Probes), QSY33 (Molecular Probes), BLACK HOLE QUENCHER™ (Glen Research), ECLIPSE™ Dark Quencher (Epoch Biosciences), IOWA BLACK™ (Integrated DNA Technologies). A quencher can reduce or quench the emission of a donor fluorophore.

In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

The term "administration" or "administering" refers to a method of giving a dosage of a pharmaceutical composition to a mammal, where the method is, e.g., oral, intravenous, intraperitoneal, intraarterial, or intramuscular. The preferred method of administration can vary depending on various factors, e.g., the components of the pharmaceutical composition, site of the potential or actual disease and severity of disease. While compounds of formula I will generally be administered perorally, other routes of administration can be useful in carrying out the methods of the invention.

By "ALK-driven cancer" is meant a cancer characterized by cells which inappropriately overexpress an ALK gene, which contain an ALK fusion gene, or which contain an ALK gene (or ALK fusion gene) bearing a mutation in an ALK gene that alters the biological activity of the ALK nucleic acid or its encoded polypeptide. In certain cases of particular interest, the ALK driven cancer is a cancer characterized by cells which have an ALK fusion gene containing at least one of the mutations disclosed herein. ALK-driven cancers can arise in any tissue, including brain, blood, connective tissue, liver, mouth, muscle, spleen, stomach, testis, and trachea. ALK-driven cancers can include cancers of the breast, non small cell lung cancer (NSCLS), neural tumors such as glioblastomas and neuroblastomas; adenocarcinomas; inflammatory myofibroblastic tumors; esophageal carcinomas, soft tissue cancers such as rhabdomyosarcomas, among others); various forms of lymphoma such as a non-Hodgkin's lymphoma (NHL) known as anaplastic large-cell lymphoma (ALCL), various forms of leukemia; and including cancers which are ALK mediated.

As used herein, the term "ALK fusion product" refers to ALK fusion proteins and/or ALK fusion genes, as described herein.

As used herein, the terms "ALK fusion protein" and "ALK fusion gene" denote a protein or nucleotide sequence that comprises a portion of the amino acid of ALK or a fragment of the nucleotide sequence of ALK, where the portions may have one or more deletions, substitutions, or additions relative to human ALK, and the portion is fused to a fusion partner. ALK fusion genes of particular interest in the practice of this invention encode an ALK fusion protein that comprises all or nearly all of the ALK intracellular portion, which encompasses the kinase domain of ALK, as discussed below. Such ALK fusion proteins retain phosphorylation activity. Exemplary fragments of ALK include the kinase domain, which includes Tyr1278, Tyr1282, and Tyr1283 of SEQ ID NOs: 2 or 4; the intracytoplasmic portion, which includes amino acids 1058 to 1620 of full length ALK (SEQ ID NOs: 2 or 4); portions of the intracytoplasmic portion, such as amino acids 1065 to 1620 of SEQ ID NOs: 2 or 4 or amino acids 1075 to 1620 of SEQ ID NOs: 2 or 4; exon 20 of ALK (SEQ ID NOs: 1 or 3); or exon 20 to exon 29 of SEQ ID NOs: 1 or 3.

As used herein, the term "ALK mutant" or "mutant" comprises one or more deletions, substitutions, or additions in the amino acid or nucleotide sequences of ALK, or fragments thereof. ALK mutants include ALK fusion proteins and ALK fusion genes. The ALK mutant can also include one or more deletions, substitutions, or additions, or a fragment thereof, as long as the mutant retains kinase phosphorylation activity. In particular ALK mutations, phosphorylation activity can be increased (e.g., by at least 5%, 10%, 15%, 20%, 30%, 40%, 50%, 60%, 70%, 80%, 90%, or even 100%), as compared to wild type ALK. ALK mutants comprise an amino acid sequence corresponding to the amino acids 1058 to 1620 of SEQ ID NOs: 2 or 4, or a fragment thereof, where said amino acid sequence has at least 85-90%, 91-93%, 94-96%, 97%, 98%, or 99% identity to the amino acid sequence of SEQ ID NOs: 2 or 4. The position of mutations in ALK and ALK-fusion products are described relative to the position of an amino acid in human ALK (SEQ ID NO: 2 or SEQ ID NO: 4). ALK mutants of the invention include the one or more of the following: a substitution for threonine at amino acid position 1151 (e.g., a threonine to lysine substitution); a substitution for leucine at amino acid position 1152 (e.g., a leucine to valine substitution); a substitution for cysteine at amino acid position 1156 (e.g., a cysteine to tyrosine substitution); a substitution for isoleucine with serine, threonine, or histidine at amino acid position 1171; a substitution for phenylalanine with serine at amino acid position 1174; a substitution for valine at amino acid position 1180 (e.g., a valine to leucine or methionine substitution); a substitution for arginine at amino acid position 1181 (e.g., an arginine to glycine substitution); a substitution for leucine with glutamine at amino acid position 1196; a substitution for leucine at amino acid position 1198 (e.g., a leucine to methionine substitution); a substitution for glycine at amino acid position 1202 (e.g., a glycine to serine substitution); a substitution for serine at amino acid position 1206 (e.g., a serine to glycine, arginine, or isoleucine substitution); a substitution for glutamic acid at amino acid position 1210 (e.g., a glutamic acid to lysine substitution); a substitution for glutamic acid at amino acid position 1241 (e.g., a glutamic acid to lysine substitution); a substitution for isoleucine at amino acid position 1268 (e.g., an isoleucine to valine substitution); and a substitution for glycine at amino acid position 1269 (e.g., a glycine to cysteine, serine, or alanine substitution) of SEQ ID NO: 2 or SEQ ID NO: 4. At the nucleic acid level the ALK mutants can comprise an amino acid sequence corresponding to the nucleotides 4083 to 5795 of SEQ ID NO: 1 or nucleotides 3320 to 5032 of SEQ ID NO: 3, or a fragment thereof, where the nucleic acid sequence has at least 85-90%, 91-93%, 94-96%, 97%, 98%, or 99% identity to the corresponding nucleic acid sequence in SEQ ID NO: 1 or SEQ ID NO: 3. For example a nucleic acid encoding a mutant ALK protein or ALK-fusion protein may contain one or more codons for the amino acid corresponding to the amino acid at position 1151 (e.g., nucleotides 4362 to 4364 of SEQ ID NO: 1 or nucleotides 3599-3601 of SEQ ID NO: 3), the amino acid at position 1152 (e.g., nucleotides 4365 to 4367 of SEQ ID NO: 1 or nucleotides 3602 to 3604 of SEQ ID NO: 3), the amino acid at position 1156 (e.g., nucleotides 4377 to 4379 of SEQ ID NO: 1 or nucleotides 3614 to 3616 of SEQ ID NO: 3), the amino acid at position 1171 (e.g., nucleotides 4422 to 4424 of SEQ ID NO: 1 or nucleotides 3659 to 3661 of SEQ ID NO: 3), the amino acid at position 1198 (e.g., nucleotides 4503 to 4505 of SEQ ID NO: 1 or nucleotides 3740 to 3742 of SEQ ID NO: 3), the amino acid at position 1202 (e.g., nucleotides 4515 to 4517 of SEQ ID NO: 1 or nucleotides 3752 to 3754 of SEQ ID NO: 3), the amino acid at position 1206 (e.g., nucleotides 4527 to 4529 of SEQ ID NO: 1 or nucleotides 3764 to 3766 of SEQ ID NO: 3), the amino acid at position 1210 (e.g., nucleotides 4539 to 4541 of SEQ ID NO: 1 or nucleotides 3776 to 3778 of SEQ ID NO: 3), the amino acid at position 1268 (e.g., nucleotides 4713 to 4715 of SEQ ID NO: 1 or nucleotides 3950 to 3952 of SEQ ID NO: 3), and the amino acid at position 1269 (e.g., nucleotides 4716 to 4718 of SEQ ID NO: 1 or nucleotides 3953-3955 of SEQ ID NO: 3) of SEQ ID NO: 2 or SEQ ID NO: 4. Non-limiting examples of nucleic acids encoding mutant ALK proteins and ALK-fusion proteins contain a nucleotide sequence corresponding to one or more of the following sequences: AAA or AAG at nucleotides 4362 to 4364 of SEQ ID NO: 1; AAA or AAG at nucleotides 3599-3601 of SEQ ID NO: 3; GTT, GTC, GTA, or GTG at nucleotides 4365 to 4367 of SEQ ID NO: 1; GTT, GTC, GTA, or GTG at nucleotides 3602 to 3604 of SEQ ID NO: 3; TAT or TAC at nucleotides 4377 to 4379 of SEQ ID NO: 1; TAT or TAC at nucleotides 3614 to 3616 of SEQ ID NO: 3; TCT, TCC, TCA, TCG, ACT, ACC, ACA, ACG, CAT, or CAC at nucleotides 4422 to 4424 of SEQ ID NO: 1; TCT, TCC, TCA, TCG, ACT, ACC, ACA, ACG, CAT, or CAC at nucleotides 3659 to 3661 of SEQ ID NO: 3; ATG at nucleotides 4503 to 4505 of SEQ ID NO: 1; ATG at nucleotides 3740 to 3742 of SEQ ID NO: 3; TCT, TCC, TCA, or TCG at nucleotides 4515 to 4517 of SEQ ID NO: 1; TCT, TCC, TCA, or TCG at nucleotides 3752 to 3754 of SEQ ID NO: 3; GGT, GGC, GGA, GGG, ATT, ATC, ATA, AGA, or AGG at nucleotides 4527 to 4529 of SEQ ID NO: 1; GGT, GGC, GGA, GGG, ATT, ATC, ATA, AGA, or AGG at nucleotides 3764 to 3766 of SEQ ID NO: 3; AAA or AAG at nucleotides 4539 to 4541 of SEQ ID NO: 1; AAA or AAG at nucleotides 3776 to 3778 of SEQ ID NO: 3; GTT, GTC, GTA, or GTG at nucleotides 4713 to 4715 of SEQ ID NO: 1; GTT, GTC, GTA, or GTG at nucleotides 3950 to 3952 of SEQ ID NO: 3; TGT, TGC, TCT, TCC, TCA, or TCG at nucleotides 4716 to 4718 of SEQ ID NO: 1; and TGT, TGC, TCT, TCC, TCA, or TCG at nucleotides 3953-3955 of SEQ ID NO: 3.

As used herein, the term "compound 1" refers to the following compound and pharmaceutically acceptable salts thereof.

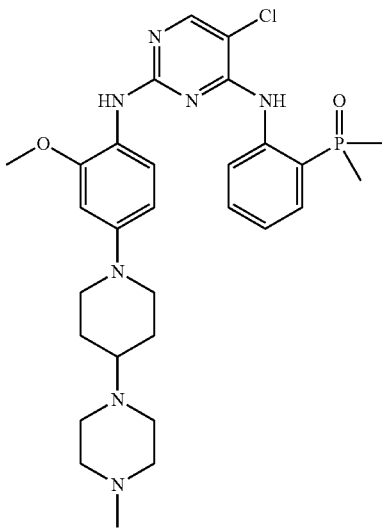

As used herein, the term "crizotinib" refers to (R)-3-[1-(2,6-dichloro-3-fluoro-phenyl)-ethoxy]-5-(1-piperidin-4-yl-1H-pyrazol-4-yl)-pyridin-2-ylamine], and pharmaceutically acceptable salts thereof (also referred to herein as "PF1066").

As used herein, the term "CH5424802" refers to a compound of the formula:

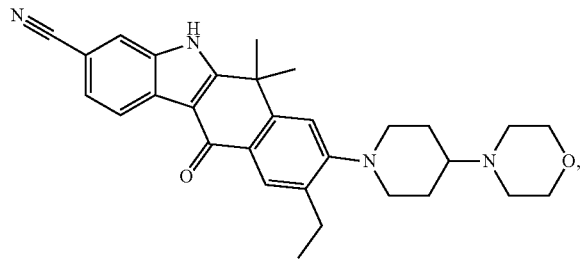 [SMILES: CCc1cc2c(cc1N1CCC(N3CCOCC3)CC1)C(C)(C)c1[nH]c3cc(C#N)ccc3c1C2=O]

and pharmaceutically acceptable salts thereof.

As used herein, the term "ASP3026" refers to a compound of the formula:

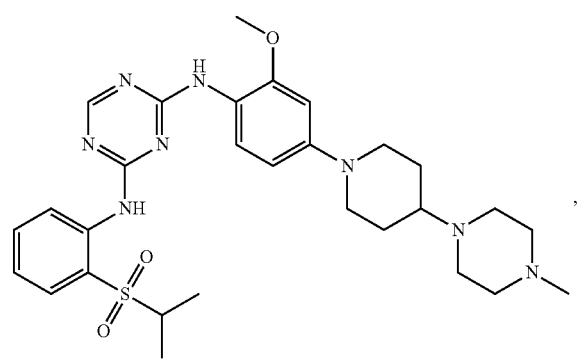 [SMILES: COc1cc(N2CCC(N3CCN(C)CC3)CC2)ccc1Nc1ncnc(Nc2ccccc2S(=O)(=O)C(C)C)n1]

and pharmaceutically acceptable salts thereof.

By the term "donor fluorophore" is meant fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3 M^{-1}$ $cm^{-1}$. A variety of compounds can be employed as donor fluorescent components, for example, in conjunction with the probes and primers of the invention, including fluorescein (and derivatives thereof), rhodamine (and derivatives thereof), GFP, pycoerythrin, BODIPY, DAPI (4'6-diamidino-2-phenylindole), Indo-1, coumarin, dansyl, and cyanine dyes. In particular examples, a donor fluorophore is a chemiluminescent molecule, such as aequorin.

As used herein, the term "fluorophore" refers to a chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescence molecules (such as aequorin) eliminates the need for an external source of electromagnetic radiation, such as a laser. Examples of particular fluorophores that can be used in the probes described herein are provided in U.S. Pat. No. 5,866,366 (herein incorporated by reference). Other suitable fluorophores are known in the art, for example, those available from Molecular Probes (Eugene, Oreg.). In particular examples, the fluorophore is used as a donor fluorophore or an acceptor fluorophore. Ideally, fluorophores have the ability to be attached to a nucleic acid probe without sufficiently interfering with the ability of the probe to interact with the target nucleic acid molecule, are stable against photobleaching, and have high quantum efficiency.

By "fluorescence reasonance energy transfer" or "FRET" is meant a process in which an excited fluorophore (the donor) transfers its excited state energy to a lower-energy light absorbing molecule (the acceptor). This energy transfer is non-radiative, and due primarily to a dipole-dipole interaction between the donor and acceptor fluorophores. This energy can be passed over a distance, for example a limited distance such as 10-100 Å. FRET efficiency drops off according to $1/(1+(R/R_0)^6)$, where $R_0$ is the distance at which the FRET efficiency is 50%.

By "FRET pairs" is meant a set of fluorophores that can engage in fluorescence resonance energy transfer (FRET). Examples of FRET pairs that can be used as listed below. However, one skilled in the art will recognize that numerous other combinations of fluorophores can be used. In particular examples, the probes disclosed herein include a FRET pair, wherein one probe of the pair includes a donor fluorophore and the other probe of the pair includes an acceptor fluorophore that can be excited by the wavelength of light emitted from the donor fluorophore. For example, an anchor probe can include a donor fluorphore and a mutation-specific probe can include the appropriate acceptor fluorophore (or vice versa). FAM is most efficiently excited by light with a wavelength of 488 nm, emits light with a spectrum of 500 to 650 nm, and has an emission maximum of 525 nm. FAM is a suitable donor fluorophore for use with JOE, TAMRA, and ROX (all of which have their excitation maxima at 514 nm, and will not be significantly stimulated by the light that stimulates FAM), as well as Cy5, Cy5.5, and LC-Red 640. The fluorophore 3-(ε-carboxy-pentyl)-3'-ethyl-5,5'-dimethyloxacarbocyanine (CYA) is maximally excited at 488 nm and can therefore serve as a donor fluorophore for rhodamine derivatives (e.g., R6G, TAMRA, and ROX), which can be used as acceptor fluorophores (see Hung et al., Anal. Biochem. 243:15 (1996)). However, CYA and FAM are not examples of a good FRET pair, because both are excited maximally at the same wavelength (488 nm). Particular examples of FRET pairs are (donor/acceptor): fluorescein/rhodamine; phycoerythrin/Cy7; fluorescein/Cy5; fluorescein/Cy5.5; fluorescein/LC-Red 640; fluorescein/LC-Red 705; and fluorescein/JA286. Suitable donor-acceptor FRET pairs are described in Grant et al. Biosens. Bioelectron. 16:231 (2001). Such FRET pairs can be used in the probes of the invention.

As used herein, the term "fusion partner" means an amino acid or a nucleotide sequence of a protein or gene other than ALK. Exemplary fusion partners include 5-aminoimidazole-4-carboxamide ribonucleotide formyltransferase/IMP cyclohydrolase (ATIC), ALK lymphoma oligomerization partner on chromosome 17 (ALOK), clathrin light chain (CLTC), cysteinyl-tRNA synthetase (CARS), echinoderm microtubule-associated protein-like 4(EML4), kinesin-1 heavy chain KIF5B), moesin (MSN), myosin (MYH), nucleophosmin (NPM), Ran-binding protein (RanBP2), TRK-fused gene (TFG), and tropomyosin (TPM).

As used herein, the term "inhibiting the proliferation of ALK-expressing cells" or cells that express an ALK mutant described herein refers to measurably slowing, stopping, or reversing the growth rate of the ALK-expressing cells in vitro or in vivo. Desirably, a slowing of the growth rate is by at least 10%, 20%, 30%, 50%, or even 70%, as determined using a suitable assay for determination of cell growth rates (e.g., a cell growth assay described herein).

By the term "primer" is meant a short nucleic acid molecule, such as a DNA oligonucleotide, for example sequences of at least 8 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of an ALK or an ALK-fusion nucleic acid), wherein the sequence of the primer is specific for the target nucleic acid molecule, for example, so that the primer will hybridize to the target nucleic acid molecule under high stringency hybridization conditions. The specificity of the primer increases with length. Thus, for example, a primer that includes 30 consecutive nucleotides will anneal to a target sequence with a higher specificity than a corresponding primer of only 8 or 15 nucleotides. Thus, to obtain greater specificity, probes and primers can be selected that include at least 8, 15, 25, 30, 35, 40, 45, 50 or more consecutive nucleotides. In particular examples, a primer is at least 8 or 15 nucleotides in length, such as at least 15 contiguous nucleotides complementary to a target nucleic acid molecule. Particular lengths of primers that can be used to practice the methods of the present disclosure (for example, to amplify a region in an ALK or an ALK-fusion nucleic acid) include primers having at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid to be amplified, such as a primer of 8-60 nucleotides, 8-50 nucleotides, or 15-30 nucleotides. Primer pairs can be used for amplification of nucleic acid sequence, for example, by PCR, real-time PCR, reverse transcription PCR, or other nucleic-acid amplification methods known in the art. An "upstream" or "forward" primer is a primer 5' to a reference point in a nucleic acid sequence. A "downstream" or "reverse" primer is a primer 3' to a reference point in a nucleic acid sequence. In general, at least one forward and one reverse primer are included in an amplification reaction. PCR primer pairs can be derived from a known sequence (such as the SEQ ID NO: 1 or SEQ ID NO: 3), for example, using computer programs intended for that purpose such as Primer (Version 0.5, ©1991, Whitehead Institute for Biomedical Research, Cambridge, Mass.) or PRIMER EXPRESS Software® (Applied Biosystems, AB, Foster City, Calif.). Methods for preparing and suing primers are described in, for example, Sambrook et al., (1989) *Molecular Cloning: A Laboratory Manual*, Cold Spring Harbor, N.Y.; Ausubel et al., (1987), *Current Protocols in Molecular Biology*, Greene Publ. Assoc. & Wiley-Intersciences. In one example, a primer includes a label.

The term "probe" as used herein refers to an isolated nucleic acid molecule that may include a detectable label or ligand, such as a primer that includes a label. Typical labels include without limitation radioactive isotopes, ligands, chemiluminescent agents, fluorophores, and enzymes. Methods for labeling and guidance in the choice of labels appropriate for various purposes are discussed, e.g., in Sambrook et al., *Molecular Cloning: A Laboratory Manual*, Cold Spring Harbor Laboratory Press (1989), and Ausubel et al., *Current Protocols in Molecular Biology*, Greene Publishing Associates and Wiley-Intersciences (1987). In a particular example, a probe includes at least on fluorophore, such as an acceptor fluorophore or donor fluorophore. For example, a fluorophore can be covalently attached at the 5'- or 3'-end of the probe. In specific examples, a fluorophore is attached to the base of the 5'-end of the probe, the base at its 3'-end, or the phosphate group at its 5'-end. Probes are generally at least 8 nucleotides in length, such as at least 12 nucleotides, at least 15 nucleotides, at least 18 nucleotides, at least 19 nucleotides, at least 20 nucleotides, or at least 25 nucleotides, such as 8-50 nucleotides, 12-50 nucleotides, 12-40 nucleotides, or 12-30 nucleotides.

As used herein, the term "refractory" refers to a cancer which is progressive in response to a given particular therapy. The cancer can be refractory either from the initial administration of the therapy; or become refractory over time in response to the therapy.

As used herein, the term "intolerant to" a drug refers to a patient who must discontinue or suspend treatment with a drug because of unacceptable side effects. The patient can be intolerant either from the initial administration of the therapy; or become intolerant over time in response to the therapy.

The term "sequence identity" is meant the shared identity between two or more nucleic acid sequence, or two or more amino acid sequences, expressed in the terms of the identity between the sequences. Sequence identity can be measured in terms of percentage identity; the higher the percentage, the more identical the sequences are. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith and Watermann, Adv. Appl. Math. 2:482 (1981); Needleman and Wunsch, J. Mol. Biol. 48:443 (1970); Pearson and Lipman, Proc. Natl. Acad. Sci. U.S.A. 85:2444 (1988); Corpet et al., Nuc. Acid Res. 16:10881 (1988); Huang et al., Computer Appls. in the Biosciences 8:155 (1992); and Pearson et al., Meth. Mol. Biol. 24:307 (1994). Altschul et al. (J. Mol. Biol. 215:403 (1990)) presents a detailed consideration of sequence alignment methods and homology calculations. The NCBI Basic Local Alignment Search Tool (BLAST) (Altschul et al., J. Mol. Biol. 215:403 (1990)) is available from several sources, including the National Center for Biological Information (NCBI) website, for use in connection with the sequence analysis programs blastp, blastn, blastx, tblastn, and tblastx. Additional information can be found at the NCBI website. BLASTN is used to compare nucleic acid sequences, while BLASTP is used to compare amino acid sequences. To compare two nucleic acid sequences, the option can be set as follows: −i is set to a file containing the first nucleic acid sequence to be compared; −j is set to a file containing the second nucleic acid sequence to be compared; −p is set to blastn; −o is set to any desired file name; −q is set to −1; −r is set to 2; and all other options are left at their default setting. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 30, 35, 40, 45, 50, 60, 70, 80, 90, 100, 150, 200, 250, 300, 350, or 400 consecutive nucleotides or amino acid residues from a sequence set forth in an identified sequence), followed by multiplying the resulting value by 100. One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to an ALK or ALK-fusion gene sequence typically hybridize to a probe based on either an entire ALK or ALK-fusion gene or selected portions of the gene (e.g., the kinase domain or a segment of the gene that contains the mutated codons described herein), under conditions described above.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "alkyl" refers to linear, branched, cyclic, and polycyclic non aromatic hydrocarbon groups, which may be substituted or unsubstituted. Unless otherwise specified, "alkyl" groups contain one to eight, and preferably one to six carbon atoms. Lower alkyl refers to alkyl groups containing 1 to 6 carbon atoms. Examples of alkyl include, without limitation, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and n-heptyl, among others. Exemplary substituted alkyl groups include, without limitation, haloalkyl groups (e.g., fluoromethyl, difluoromethyl, trifluoromethyl, 2-fluoroethyl, 3-fluoropropyl), hydroxymethyl, 2-hydroxyethyl, 3-hydroxypropyl), benzyl, substituted benzyl, and phenethyl, among others.

The term "alkoxy" refers to a subset of alkyl in which an alkyl group as defined above with the indicated number of carbons attached through an oxygen bridge, —O-alkyl, wherein the alkyl group contains 1 to 8 carbons atoms and is substituted or unsubstituted.

Exemplary alkoxy groups include, without limitation, methoxy, ethoxy, n-propoxy, i-propoxy, t-butoxy, n-butoxy, s-pentoxy, —OCF$_3$, and —O-cyclopropyl.

The term "haloalkyl" refers to a subset of alkyl in which an alkyl group as defined above having one or more hydrogen atoms of the alkyl substituted with a halogen atom. Exemplary haloalkyl groups include, without limitation, trifluoromethyl, trichloromethyl, pentafluoroethyl and the like.

The term "alkenyl" refers to a branched or unbranched hydrocarbon group containing one or more double bonds and having from 2 to 8 carbon atoms. An alkenyl may optionally include monocyclic or polycyclic rings, in which each ring desirably has from three to six members. The alkenyl group may be substituted or unsubstituted. Alkenyl groups include, without limitation, vinyl, allyl, 2-cyclopropyl-1-ethenyl, 1-propenyl, 1-butenyl, 2-butenyl, 3-butenyl, 2-methyl-1-propenyl, and 2-methyl-2-propenyl.

The term "alkynyl" refers to a branched or unbranched hydrocarbon group containing one or more triple bonds and having from 2 to 8 carbon atoms. The alkynyl group may be substituted or unsubstituted. Alkynyls include, without limitation, ethynyl, 1-propynyl, 2-propynyl, 1-butynyl, 2-butynyl, and 3-butynyl.

The term "cycloalkyl" refers to cyclic or polycyclic hydrocarbon groups of from 3 to 13 carbon atoms, any of which is saturated. Cycloalkyl groups may be substituted or unsubstituted. Exemplary cycloalkyl groups include, without limitation, cyclopropyl, norbornyl, [2.2.2]bicyclooctane, and [4.4.0]bicyclodecane, and the like, which, as in the case of other alkyl moieties, may optionally be substituted.

The term "cycloalkenyl" refers to cyclic or polycyclic hydrocarbon groups of from 3 to 13 carbon atoms, preferably from 5 to 8 carbon atoms, containing one or more double bonds. Cycloalkenyl groups may be substituted or unsubstituted. Exemplary cycloalkenyl groups include, without limitation, cyclopentenyl, cyclohexenyl, and cyclooctenyl.

The term "cycloalkynyl" refers to cyclic or polycyclic hydrocarbon groups of from 5 to 13 carbon atoms containing one or more triple bonds. Cycloalkynyl groups may be substituted or unsubstituted.

The term "heteroalkyl" is meant a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Examples of heteroalkyls include, without limitation, polyethers, such as methoxymethyl and ethoxyethyl.

As used herein, "heterocyclic ring" and "heterocyclyl" refer to non-aromatic ring systems having five to fourteen ring atoms in which one or more ring carbons, preferably one to four, are each replaced by a heteroatom such as N, O, S, or P. Heterocyclic rings may be substituted or unsubstituted and may include one, two, or three fused or unfused ring systems. Desirably, the heterocyclic ring is a 5- to 7-membered monocyclic or 7- to 14-membered bicyclic heterocyclic ring consisting of 2 to 6 carbon atoms and 1, 2, 3, or 4 heteroatoms independently selected from N, O, and S and including any bicyclic group in which any of the above-defined heterocyclic rings is fused to a benzene ring. Exemplary heterocyclic rings include, without limitation, 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. A heterocyclyl group can include two or more of the ring systems listed above. Heterocyclic rings include those in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring.

The term "aryl" used alone or as part of a larger moiety as in "aralkyl", "aralkoxy", or "aryloxyalkyl", refers to aromatic monocyclic or polycyclic ring groups having six to fourteen ring atoms, such as phenyl, 1-naphthyl, 2-naphthyl, 1-anthracyl, and 2-anthracyl. An "aryl" ring may be substituted or unsubstituted. The term "aryl" includes fused polycyclic aromatic ring systems in which an aromatic ring is fused to one or more rings. Non-limiting examples of aryl groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro, 1-naphthyl, 2-naphthyl, 1-anthracyl, and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and include both monocyclic and polycyclic ring systems. Examples of typical heteroaryl rings include 5-membered monocyclic rings, such as thienyl, pyrrolyl, imidazolyl, pyrazolyl, furyl, isothiazolyl, furazanyl, isoxazolyl, and thiazolyl; 6-membered monocyclic rings, such as pyridyl, pyrazinyl, pyrimidinyl, pyridazinyl, and triazinyl; and polycyclic heterocyclic rings, such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl (see e.g. Katritzky, Handbook of Heterocyclic Chemistry). Exemplary heteroaryl rings include, without limitation, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, and benzoisoxazolyl. Heteroaryl groups further include a group in which a heteroaromatic ring is fused to one or more aromatic or nonaromatic rings where the radical or point of attachment is on the heteroaromatic ring, such as tetrahydroquinoline, tetrahydroisoquinoline, and pyrido[3,4-d]pyrimidinyl, imidazo[1,2-a]pyrimidyl, imidazo[1,2-a]pyrazinyl, imidazo[1,2-a]pyridinyl, imidazo[1,2-c]pyrimidyl, pyrazolo[1,5-a][1,3,5]triazinyl, pyrazolo[1,5-c]pyrimidyl, imidazo[1,2-b]pyridazinyl, imidazo[1,5-a]pyrimidyl, pyrazolo[1,5-b][1,2,4]triazine, quinolyl, isoquinolyl, quinoxalyl, imidazotriazinyl, pyrrolo[2,3-d]pyrimidyl, triazolopyrimidyl, and pyridopyrazinyl.

An aryl group or heteroaryl group may contain one or more substituents. Exemplary substituents for aryl or heteroaryl group include halogen (F, Cl, Br or I), alkyl, alkenyl, alkynyl, heteroalkyl, —$NO_2$, —CN, —$R^A$, —$OR^B$, —$S(O)_rR^B$, (wherein r is 0, 1 or 2), —$SO_2NR^AR^B$, —$NR^AR^B$, —O—$NR^AR^B$, —$NR^A$—$NR^AR^B$, —(CO)$YR^B$, —O(CO)$YR^B$, —$NR^A$(CO)$YR^B$, —S(CO)$YR^B$, —$NR^AC(=S)YR^B$, —OC(=S)$YR^B$, —C(=S)$YR^B$, —YC(=$NR^A$)$YR^B$, —YC(=N—$OR^A$)$YR^B$, —YC(=N—$NR^AR^B$)$YR^B$, —$COCOR^B$, —$COMCOR^B$ (where M is a $C_{1-6}$ alkyl group), —YP(O)($YR^C$)($YR^C$), —P(O)($R^C$)$_2$, —Si($R^C$)$_3$, —$NR^ASO_2R^B$, and —$NR^ASO_2NR^AR^B$, wherein each occurrence of Y is, independently, —O—, —S—, —$NR^A$—, or a chemical bond (i.e., —(CO)$YR^B$ thus encompasses —C(=O)$R^B$, —C(=O)$OR^B$, and —C(=O)$NR^AR^B$).

$R^C$ is selected from alkyl, alkenyl, alkynyl, cycloalkyl, cycloalkenyl, cycloalkynyl, aryl, heteroaryl, and heterocyclyl. At each occurrence, each of $R^A$ and $R^B$ is, independently, selected from hydrogen, alkyl, alkenyl, alkynyl, cycloalkyl, cycloalkenyl, cycloalkynyl, aryl, heteroaryl, and heterocyclyl.

Each of $R^A$, $R^B$ and $R^C$ optionally bears one or more substituents selected from amino, alkylamino, dialkylamino, aminocarbonyl, halogen, alkyl, aryl, heteroalkyl, heteroaryl, carbocycle, heterocycle, alkylaminocarbonyl, dialkylaminocarbonyl, alkylaminocarbonyloxy, dialkylaminocarbonyloxy, nitro, cyano, carboxy, alkoxycarbonyl, alkylcarbonyl, alkoxy, haloalkoxy groups, hydroxy, protected hydroxyl groups (e.g., —O—X, where X is acyl, phenyl, substituted phenyl, benzyl, substituted benzyl, phenethyl, or substituted phenethyl), -M-heteroaryl, -M-heterocycle, -M-aryl, -M-$OR^B$, -M-$SR^B$, -M-$NR^AR^B$, -M-OC(O)$NR^AR^B$, -M-C(=$NR^B$)$NR^AR^B$, -M-C(=$NR^A$)$OR^B$, -M-P(=O)($R^C$)$_2$, Si($R^C$)$_3$, -M-$NR^AC(O)R^B$, -M-$NR^AC(O)OR^B$, -M-C(O)$R^B$, -M-C(=S)$R^B$, -M-C(=S)$NR^AR^B$, -M-C(O)$NR^AR^B$, -M-C(O)$NR^B$-M-$NR^AR^B$, -M-$NR^BC(NR^A)NR^AR^B$, -M-$NR^AC(S)NR^AR^B$, -M-S(O)$_2R^A$, -M-C(O) $R^A$, -M-OC(O) $R^A$, -MC(O)$SR^B$, -M-S(O)$_2NR^AR^B$, —C(O)-M-C(O)$R^B$, -M$CO_2R^B$, -MC(=O)$NR^AR^B$, -M-C(=NH)$NR^AR^B$, and -M-OC(=NH)$NR^AR^B$, wherein M is a $C_{1-6}$ alkyl group. Non-limiting illustrations of a substituted $R^A$, $R^B$ or $R^C$ group include haloalkyl and trihaloalkyl, alkoxyalkyl, halophenyl, chloromethyl, trichloromethyl, trifluoromethyl, methoxyethyl, alkoxyphenyl, halophenyl, —$CH_2$-aryl, —$CH_2$-heterocycle, —$CH_2C(O)NH_2$, —C(O)$CH_2N(CH_3)_2$, —$CH_2CH_2OH$, —$CH_2OC(O)NH_2$, —$CH_2CH_2NH_2$, —$CH_2CH_2CH_2NEt_2$, —$CH_2OCH_3$, —C(O)$NH_2$, —CH$_2$CH$_2$-heterocycle, —C(=S)CH$_3$, —C(=S)NH$_2$, —C(=NH)NH$_2$, —C(=NH)OEt, —C(O)NH-cyclopropyl, —C(O)NHCH$_2$CH$_2$-heterocycle, —C(O)NHCH$_2$CH$_2$OCH$_3$, —C(O)CH$_2$CH$_2$NHCH$_3$, —CH$_2$CH$_2$F, —C(O)CH$_2$-heterocycle, —CH$_2$C(O)NHCH$_3$, —CH$_2$CH$_2$P(=O)(CH$_3$)$_2$, and —Si(CH$_3$)$_3$.

An alkyl, alkenyl, alkynyl, alkoxy, haloalkyl, heteroalkyl, cycloalkyl, cycloalkenyl, cycloalkynyl, or heterocyclic group may contain one or more substituents selected from those listed above for aryl and heteroaryl groups, in addition to =O, =S, =NH, =NNR$^A$R$^B$, =NNHC(O)R$^B$, =NNHCO$_2$R$^B$, or =NNHSO$_2$R$^B$, wherein R$^A$ and R$^B$ are as defined above.

Other features and advantages of the invention will be apparent from the following detailed description, the drawings, and the claims.

BRIEF DESCRIPTION OF THE DRAWINGS

FIG. 2A shows data for exposure to crizotinib at 500, 720, 1000, or 1440 nM. FIG. 2B shows data for exposure to compound 1 at 100, 200, 500, or 1000 nM.

FIG. 4A shows a representative proliferation curve for crizotinib. FIG. 4B shows a representative proliferation curve for compound 1.

FIG. 5A is a graph showing ALK phosphorylation (% p-ALK) and plasma levels for a dosage of crizotinib at 200 mg/kg. FIG. 5B is a graph showing ALK phosphorylation (% p-ALK) and plasma levels for a dosage of compound 1 at 50 mg/kg.

FIG. 8 shows the mRNA sequence for human ALK (SEQ ID NOs: 1 and 3). The codons in bold and underlined represent the codons that are mutated in the mutant ALK nucleic acids described herein.

FIG. 9 shows the protein sequence for human ALK (SEQ ID NOs: 2 and 4). The amino acids in bold and underlined represent the amino acids that are mutated in the mutant ALK proteins described herein.

FIG. 10 shows the protein and mRNA sequence of the NPM/ALK fusion (SEQ ID NOs: 5 and 6).

DETAILED DESCRIPTION

Figure 1:
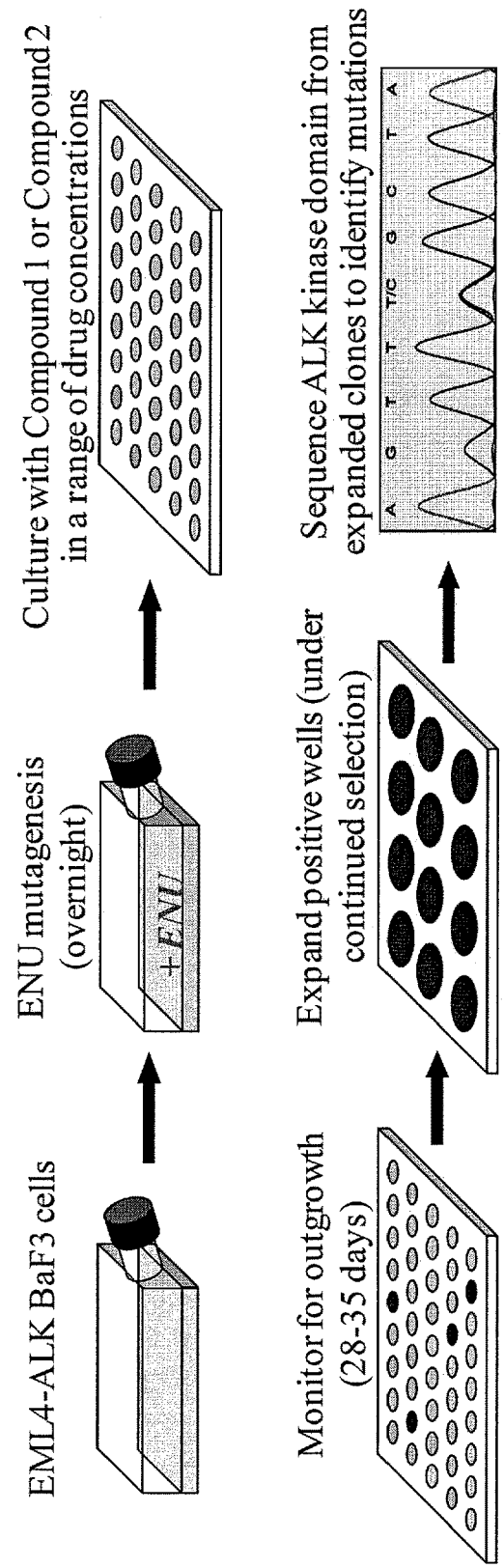
FIG. 1 is a schematic diagram of an exemplary protocol for accelerated in vitro mutagenesis.

Culturing EML4-ALK-expressing cells in the presence of certain ALK-inhibitors (e.g. to one or more of crizotinib, CH5424802 and ASP3026) led to the selection and identification of cells expressing ALK mutations. The nucleotide sequences were analyzed and a set of seven mutations were identified that conferred varying degrees of resistance to one or more of crizotinib, CH5424802 and ASP3026.

We have observed that the ALK mutants that are resistant to one or more of crizotinib, CH5424802 and ASP3026 can still be inhibited potently by compounds of formula (I), such as compound 1.

The invention features a method for treating patients who have an ALK-driven cancer, which is, or has become, refractory to one or more of crizotinib, CH5424802 and ASP3026, or which bears an ALK mutation identified herein, by administering a compound of formula (I) to the patient. The invention also features a method for characterizing ALK-driven cancers to determine whether they express an ALK mutant.

ALK Mutants

ALK mutants include one or more deletions, substitutions, or additions in the amino acid or nucleotide sequences of ALK, or fragments thereof, and can include ALK fusion proteins and ALK fusion genes. Thus, an ALK mutant includes ALK fusion proteins and ALK genes with one or more deletions, substitutions, or additions, or a fragment thereof.

An ALK mutant also includes amino acid and nucleotide sequences of ALK with one or more deletions, substitutions, or additions, such as point mutations. Where the mutant is a protein or polypeptide, preferable substitutions are conservative substitutions, which are substitutions between amino acids similar in properties such as structural, electric, polar, or hydrophobic properties. For example, the substitution can be conducted between basic amino acids (e.g., Lys, Arg, and His), or between acidic amino acids (e.g., Asp and Glu), or between amino acids having non-charged polar side chains (e.g., Gly, Asn, Gln, Ser, Thr, Tyr, and Cys), or between amino acids having hydrophobic side chains (e.g., Ala, Val, Leu, Ile, Pro, Phe, and Met), or between amino acids having branched side chains (e.g., Thr, Val, Leu, and Ile), or between amino acids having aromatic side chains (e.g., Tyr, Trp, Phe, and His). ALK mutants of particular interest are those identified by culturing EML4-ALK-expressing cells in the presence of the ALK-inhibitor PF 1066.

Where the mutant is a nucleic acid, the DNA encoding an ALK mutant protein may comprise a nucleotide sequence capable of hybridizing to a complement sequence of the nucleotide sequence encoding an ALK mutant as defined above, under stringent conditions. As used herein, the stringent conditions include low, medium or high stringent conditions. An example of the stringent conditions includes hybridization at approximately 42-55° C. in approximately 2-6×SSC, followed by wash at approximately 50-65° C. in approximately 0.1-1×SSC containing approximately 0.1-0.2% SDS, where 1×SSC is a solution containing 0.15 M NaCl and 0.015 M Na citrate, pH 7.0. Wash can be performed once or more. In general, stringent conditions may be set at a temperature approximately 5° C. lower than a melting temperature (Tm) of a specific nucleotide sequence at defined ionic strength and pH.

Many ALK fusion proteins and ALK fusion genes include the entire intracytoplasmic portion or most of the intracytoplasmic portions of ALK. The amino acid and nucleotide sequences of ALK and DNAs encoding them are available from known databases such as NCBI GenBank (USA), EMBL (Europe), etc. For example, GenBank accession numbers are ALK [Homo sapiens] (AB209477, U62540, NG_009445.1, and GeneID: 238). Exemplary ALK fusion proteins and fusion genes having the entire intracytoplasmic portion include TRK-fused gene/anaplastic lymphoma kinase (Ki-1) fusion protein long form [Homo sapiens] (AAF27292.1), TRK-fused gene-anaplastic lymphoma kinase fusion protein [Homo sapiens] (AAF42734.1), fusion protein EML4-ALK variant 5 splicing isoform a [Homo sapiens] (BAG75148.1), fusion protein KIF5B-ALK [Homo sapiens] (BAH57337.1), fusion protein EML4-ALK variant 5 splicing isoform b [Homo sapiens] (BAG75149.1), fusion protein EML4-ALK variant 4 [Homo sapiens] (BAG75147.1), fusion protein EML4-ALK variant 2 [Homo sapiens] (BAF73612.1), fusion protein EML4-ALK variant 1 [Homo sapiens] (BAF73611.1), fusion protein EML4-ALK variant 7 [Homo sapiens] (BAH57336.1), fusion protein EML4-ALK variant 6 [Homo sapiens] (BAH57335.1), fusion protein EML4-ALK variant 3 splicing isoform b [Homo sapiens] (BAG55004.1), fusion protein EML4-ALK variant 3 splicing isoform a [Homo sapiens] (BAG55003.1), nucleophosmin-anaplastic lymphoma kinase fusion protein [Homo sapiens] (AAA58698.1), tropomyosin 4-anaplastic lymphoma kinase fusion protein minor isoform [Homo sapiens] (AAK51964.1), tropomyosin 4-anaplastic lymphoma kinase fusion protein major isoform [Homo sapiens] (AAK51963.1), EML4/ALK fusion protein variant 3 [Homo sapiens] (ABX59674.1), moesin/anaplastic lymphoma kinase fusion protein [Homo sapiens] (AAK71522.1), TPM4-ALK fusion oncoprotein type 1 [Homo sapiens] (AAG17015.1), TRK-fused gene/anaplastic large cell lymphoma kinase extra long form [Homo sapiens] (AAM17922.1), EML4/ALK fusion protein variant 3 (EML4/ALK fusion) mRNA [Homo sapiens] (EU236948.1), TRK-fused gene (TFG), transcript variant 1, mRNA [Homo sapiens] (NM_006070.4 GI:56090655), TRK-fused gene (TFG), transcript variant 2, mRNA [Homo sapiens] (NM_001007565.1), TRK-fused gene-anaplastic lymphoma kinase fusion protein (TFG/ALK) mRNA, complete cds [Homo sapiens] (AF125093.1), and TRK-fused gene/anaplastic lymphoma kinase (Ki-1) fusion protein long form (TFG/ALK fusion) mRNA, complete cds [Homo sapiens] (AF143407.1). Exemplary ALK fusion proteins having a portion of the entire intracytoplasmic portion include moesin/anaplastic lymphoma kinase fusion protein and fusion gene (AAK71522.1 and AF295356.1), which contain the final 557 amino acids of ALK; and MYH-9-ALK (see Lamant et al., Genes Chromosomes Cancer. 37:427-432, 2003), which contains the final 556 residues of ALK.

Other exemplary ALK fusion proteins are ALO17-ALK, ATIC-ALK (e.g., inv(2(p23;q35)), CARS-ALK, CLTC-ALK (e.g., t(2;17)(p23;q21)), EML4-ALK (e.g., inv(2)(p21; p23)), KIF5B-ALK, MSN-ALK (e.g., t(2;X)(p23;q11-12)), MYH9-ALK, NPM-ALK (e.g., t(2;5)(p23;q35)), RanBP2-ALK, SEC31L1-ALK, forms of TFG-ALK (including TFG-ALK (e.g., t(2;3)(p23;q21)), $TFG_L$-ALK (e.g., t(2;3)(p23; q21)), and $TFG_{XL}$-ALK), TPM3-ALK (e.g., t(1;2)(q25; p23)), and TPM4-ALK (e.g., t(2;19)(p23;p13.1)). ALK fusion proteins also include variants of any fusion. Exemplary variants of an EML4-ALK fusion protein include that arise from variable exon regions of EML4 fused to exon 20 of ALK, such as variant 1 with fused exon 13 of EML4 to exon 20 of ALK (see, e.g., Koivunen et al., Clin. Cancer Res. 14:4275 (2008)); variant 2 with fused exon 20 of EML-4 (see, e.g., Horn et al., J. Clin. Oncol. 27:4232 (2009)); variant 3 with fused exon 6 of EML-4 (see, e.g, Koivunen et al., supra, and Choi et al., Cancer Res. 68:4971 (2008)); variant 4 with fused exon 14 of EML-4 (see, e.g., Horn et al., supra); variant 5 with fused exon 18 of EML-4 (see, e.g., Wong et al., Cancer 115:1723 (2009)); variant 6 with fused exon 13 of EML-4; variant 7 with fused exon of 14; and other variants that include additional nucleotides from the adjacent intron or that exclude nucleotides from the recited exon (e.g., variant 3a with fused exon 6 of EML-4 and variant 3b with fused exon 6 and an addition 33 base pairs from intron 6 of EML-4).

Characterization of ALK-Driven Cancers

ALK mutant expression or overexpression is determined in a diagnostic or prognostic assay by evaluating levels of ALK mutants in biological sample, or secreted by the cell (e.g., via an immunohistochemistry assay using anti-ALK antibodies or anti-p-ALK antibodies; FACS analysis, etc.). Alternatively, or additionally, one can measure levels of ALK mutant-encoding nucleic acid or mRNA in the cell, e.g., via fluorescent in situ hybridization using a nucleic acid based probe corresponding to an ALK mutant-encoding nucleic acid or the complement thereof; (FISH; see WO98/45479, published October, 1998), Southern blotting, Northern blotting, or polymerase chain reaction (PCR) techniques, such as real time quantitative PCR (RT-PCR). One can also study ALK mutant expression by measuring shed antigen in a biological sample, such as serum, e.g., using antibody-based assays (see also, e.g., U.S. Pat. No. 4,933,294, issued Jun. 12, 1990; WO91/05264, published Apr. 18, 1991; U.S. Pat. No. 5,401,638, issued Mar. 28, 1995; and Sias et al., J. Immunol. Methods 132:73 (1990)). Aside from the above assays, various in vivo assays are available to the skilled practitioner. For example, one can expose cells within the body of the mammal to an antibody which is optionally labeled with a detectable label, e.g., a radioactive isotope, and binding of the antibody to cells in the mammal can be evaluated, e.g., by external scanning for radioactivity or by analyzing a biopsy taken from a mammal previously exposed to the antibody.

Examples of biological properties that can be measured in isolated cells include mRNA expression, protein expression, and DNA quantification. Additionally, the DNA of cells isolated by the methods of the invention can be sequenced, or certain sequence characteristics (e.g., polymorphisms and chromosomal abnormalities) can be identified using standard techniques, e.g., FISH or PCR. The chemical components of cells, and other analytes, may also be assayed after isolation. Cells may also be assayed without lysis, e.g., using extracellular or intracellular stains or by other observation, e.g., morphology or growth characteristics in various media.

While any hybridization technique can be used to detect the gene rearrangements, one preferred technique is fluorescent in situ hybridization (FISH). FISH is a cytogenetic technique which can be used to detect and localize the presence or absence of specific DNA or RNA sequences on chromosomes. FISH incorporates the use of fluorescently labeled nucleic acid probes which bind only to those parts of the chromosome with which they show a high degree of sequence similarity. Fluorescence microscopy can be used to find out where the fluorescent probe bound to the chromosome. The basic steps of FISH are outlined below. Exemplary FISH probes include Vysis LSI ALK Dual Color, Break Apart Rearrangement Probe (Abbott, Downers Grove, Ill.), which hybridizes to band 2p23 on either side of the ALK gene breakpoint; and Split Signal ALK FISH DNA Probe (Dako), which hybridizes to a 289 kb segment telomeric to the ALK breakpoint and to a 557 kb segment centromeric to the ALK breakpoint.

For FISH, a probe is constructed that is long enough to hybridize specifically to its target (and not to similar sequences in the genome), but not too large to impede the hybridization process. Probes are generally labeled with fluorophores, with targets for antibodies, with biotin, or any combination thereof. This can be done in various ways, for example using random priming, nick translation, and PCR using tagged nucleotides.

Generally, a sample or aliquot of a population of cells is used for FISH analysis. For example, in one method of preparation, cells are trypsinized to disperse into single cells, cytospun onto glass slides, and then fixed with paraformaldehyde before storing in 70% ethanol. For preparation of the chromosomes for FISH, the chromosomes are firmly attached to a substrate, usually glass. After preparation, the probe is applied to the chromosome RNA and starts to hybridize. In several wash steps all unhybridized or partially hybridized probes are washed away. If signal amplification is necessary to exceed the detection threshold of the microscope (which depends on many factors such as probe labeling efficiency, the kind of probe, and the fluorescent dye), fluorescent tagged antibodies or strepavidin are bound to the tag molecules, thus amplifying the fluorescence.

An epifluorescence microscope is used for observation of the hybridized sequences. The white light of the source lamp is filtered so that only the relevant wavelengths for excitation of the fluorescent molecules arrive onto the sample. Emission of the fluorochromes happens, in general, at larger wavelengths, which allows one to distinguish between excitation and emission light by mean of another optical filter. With a more sophisticated filter set, it is possible to distinguish between several excitation and emission bands, and thus between several fluorochromes, which allows observation of many different probes on the same strand.

Depending on the probes used, FISH can have resolution ranging from huge chromosomes or tiny (~100 kilobase) sequences. The probes can be quantified simply by counting dots or comparing color.

Methods for the identification of a mutation in an ALK or an ALK-fusion product are provided that include contacting a target ALK or ALK-fusion nucleic acid (e.g., mRNA or amplified product) with a first and second probes (as described herein), under conditions that permit hybridization between the target nucleic acid molecule and the first and second probes. The resulting hybridization complex is heated to increase the temperature and permit melting of the hybridization complex. The resulting melting curve is detected, for example, by detecting a fluorescent signal from a donor or acceptor fluorophore on the probes, wherein a melting point temperature shift compared to a melting curve expected for the wild-type target sequence indicates the presence of a mutation in the target ALK or ALK-fusion nucleic acid. Is some examples, the test melting curve is compared to a melting curve for a control, such as a wild type or mutant ALK or mutant ALK-fusion nucleic acid. The methods described herein may used to determine a treatment protocol.

An additional method that may be used to identify a nucleic acid encoding a mutant ALK or mutant ALK-fusion protein (described herein) is allele-specific quantitative real time-PCR (see, for e.g., Diagnostic Innovations DxS BCR-ABL T3151 Mutation Test Kit, and Singer et al., Methods in Molec. Biol. 181:145 (2001)). This technique utilizes Taq DNA polymerase, which is extremely effective at distinguishing between a match and a mismatch at the 3'-end of the primer (when the 3'-base is mismatched, no efficient amplification occurs). Using this technique, the 3'-end of the primer may be designed to specifically hybridize to a nucleic acid sequence that corresponds to a codon that encodes a mutant amino acid in an ALK or an ALK-fusion protein (as described herein). In this way, the specific mutated sequences can be selectively amplified in a patient sample. This technique further utilizes a Scorpion probe molecule, which is a bifunctional molecule containing a PCR primer, a fluorophore, and a quencher. The fluorophore in the probe interacts with a quencher, which reduces fluorescence. During a PCR reaction, when the Scorpion probe binds to the amplicon, the fluorophore and quencher in the Scorpion probe become separated, which leads to an increase in fluorescence from the reaction tube. Any of the primers described herein may be used in allele-specific quantitative real time PCR.

A biological sample can be analyzed to detect a mutation in an ALK gene, or expression levels of an ALK gene, by methods that are known in the art. For example, methods such as direct nucleic acid sequencing, altered hybridization, aberrant electrophoretic gel migration, binding or cleavage mediated by mismatch binding proteins, single-strand conformational polymorphism (SSCP) analysis, or restriction fragment length polymorphism (RFLP) analysis of PCR products derived from a patient sample can be used to detect a mutation in an ALK gene; ELISA can be used to measure levels of ALK polypeptide; and PCR can be used to measure the level of an ALK nucleic acid molecule.

Any of these techniques may be used to facilitate detection of a mutation in a candidate gene, and each is well known in the art; examples of particular techniques are described, without limitation, in Orita et al. (Proc. Natl. Acad. Sci. USA 86:2766 (1989)) and Sheffield et al. (Proc. Natl. Acad. Sci. USA 86:232 (1989)). Furthermore, expression of the candidate gene in a biological sample (e.g., a biopsy) may be monitored by standard Northern blot analysis or may be aided by PCR (see, e.g., Ausubel et al., Current Protocols in Molecular Biology, John Wiley & Sons, New York, N.Y. (1995); PCR Technology: Principles and Applications for DNA Amplification, H.A. Ehrlich, Ed., Stockton Press, NY; Yap et al., Nucl. Acids. Res. 19:4294 (1991)).

Primers for use in PCR, reverse-transcription PCR, or quantitative real time PCR may be designed to amplify a sequence within an ALK gene, an ALK fusion gene, or an mRNA encoding an ALK protein or an ALK fusion protein, that contains one or more (e.g., 1, 2, 3, 4, or 5) specific mutation(s) associated with an increased risk of developing a proliferative order or associated with increased resistance to treatment with a tyrosine kinase inhibitor (e.g., to one or more of crizotinib, CH5424802 and ASP3026). For example, primers (e.g., 8 to 30 nucleotides) may be designed to amplify a specific contiguous sequence within a nucleic acid (e.g., mRNA) encoding human full-length ALK (human ALK mRNA, Genbank Accession No: U62540 and Genbank Accession No. U66559 (SEQ ID NOS: 1 and 3, respectively) or human ALK-fusion proteins (e.g., ALO17-ALK, ATIC-ALK, CARS-ALK, CLTC-ALK, EML4-ALK, KIF5B-ALK, MSN-ALK (e.g., t(2;X)(p23;q11-12)), MYH9-ALK, NPM-ALK, RanBP2-ALK, SEC31L1-ALK, $TFG_S$-ALK, $TFG_L$-ALK, $TFG_{XL}$-ALK, TPM3-ALK, or TPM4-ALK) that encodes one or more of the amino acids corresponding to: the amino acid at position 1151, the amino acid at position 1152, the amino acid at position 1156, the amino acid at position 1171, the amino acid at position 1174, the amino acid at position 1180, the amino acid at position 1181, the amino acid at position 1196, the amino acid at position 1198, the amino acid at position 1202, the amino acid at position 1206, the amino acid at position 1210, the amino acid at position 1241, the amino acid at position 1268, and the amino acid at position 1269 of SEQ ID NO: 2 or SEQ ID NO: 4. For example, primers may be designed to amplify the kinase domain of nucleic acid encoding an ALK or ALK-fusion protein (e.g., 5'-AGCGATGCAGATG-GAATTGCAGAG-3 (SEQ ID NO: 7) and 5'-CAATAG-GCAGCGCCGTGTTGATTA-3'(SEQ ID NO: 8)). The kinase domain in an ALK protein or an ALK-fusion protein corresponds to the sequence of amino acids 1058 to 1620 in SEQ ID NO: 2 or 4 (encoded by a sequence that corresponds to nucleotides 4083 to 5795 in SEQ ID NO: 1 and nucleotides 3320 to 5032 in SEQ ID NO: 3). Desirably, the primers or probes of the invention are designed to amplify or hybridize a contiguous sequence of nucleotides (e.g., 20 to 6226 nucleotides) within a nucleic acid encoding an ALK or ALK-fusion protein sequence that contains one or more codons for the amino acid corresponding to the amino acid at position 1151 (e.g., nucleotides 4362 to 4364 of SEQ ID NO: 1 or nucleotides 3599-3601 of SEQ ID NO: 3), the amino acid at position 1152 (e.g., nucleotides 4365 to 4367 of SEQ ID NO: 1 or nucleotides 3602 to 3604 of SEQ ID NO: 3), the amino acid at position 1156 (e.g., nucleotides 4377 to 4379 of SEQ ID NO: 1 or nucleotides 3614 to 3616 of SEQ ID NO: 3), the amino acid at position 1171 (e.g., nucleotides 4422 to 4424 of SEQ ID NO: 1 or nucleotides 3659 to 3661 of SEQ ID NO: 3), the amino acid at position 1174 (e.g., nucleotides 4431 to 4433 of SEQ ID NO: 1 or nucleotides 3668 to 3670 of SEQ ID NO: 3), the amino acid at position 1180 (e.g., nucleotides 4449 to 4451 of SEQ ID NO: 1 or nucleotides 3686 to 3688 of SEQ ID NO: 3), the amino acid at position 1181 (e.g., nucleotides 4452 to 4454 of SEQ ID NO: 1 or nucleotides 3689 to 3691 of SEQ ID NO: 3), the amino acid at position 1196 (e.g., nucleotides 4497 to 4499 of SEQ ID NO: 1 or nucleotides 3734 to 3736 of SEQ ID NO: 3), the amino acid at position 1198 (e.g., nucleotides 4503 to 4505 of SEQ ID NO: 1 or nucleotides 3740 to 3742 of SEQ ID NO: 3), the amino acid at position 1202 (e.g., nucleotides 4515 to 4517 of SEQ ID NO: 1 or nucleotides 3752 to 3754 of SEQ ID NO: 3), the amino acid at position 1206 (e.g., nucleotides 4527 to 4529 of SEQ ID NO: 1 or nucleotides 3764 to 3766 of SEQ ID NO: 3), the amino acid at position 1210 (e.g., nucleotides 4539 to 4541 of SEQ ID NO: 1 or nucleotides 3776 to 3778 of SEQ ID NO: 3), the amino acid at position 1241 (e.g., nucleotides 4632 to 4634 of SEQ ID NO: 1 or nucleotides 3869 to 3871 of SEQ ID NO: 3), the amino acid at position 1268 (e.g., nucleotides 4713 to 4715 of SEQ ID NO: 1 or nucleotides 3950 to 3952 of SEQ ID NO: 3), and the amino acid at position 1269 (e.g., nucleotides 4716 to 4718 of SEQ ID NO: 1 or nucleotides 3953-3955 of SEQ ID NO: 3) of SEQ ID NO: 2 or SEQ ID NO: 4. The amino acids at positions 1151, 1152, 1156, 1171, 1174, 1180, 1181, 1196, 1198, 1202, 1206, 1210, 1241, 1268, and 1269 in wild-type ALK protein (SEQ ID NOS: 2 or 4) are T1151, L1152, C1156, I1171, F1174, V1180, R1181, L1196, L1198, G1202, S1206, E1210, E1241, I1268, and G1269 (indicated in bold and underlined in FIG. 9).

The methods of the invention provide primers and probes that may be used to amplify or identify (hybridize under stringent conditions) a nucleic acid (e.g., mRNA) encoding a mutant ALK or ALK fusion protein that contains one or more codons corresponding to the following sequences: nucleotides 4362 to 4364 of SEQ ID NO: 1 (e.g., AAA or AAG); nucleotides 3599-3601 of SEQ ID NO: 3 (e.g., AAA or AAG); nucleotides 4365 to 4367 of SEQ ID NO: 1 (e.g., GTT, GTC, GTA, or GTG); nucleotides 3602 to 3604 of SEQ ID NO: 3 (e.g., GTT, GTC, GTA, or GTG); nucleotides 4377 to 4379 of SEQ ID NO: 1 (e.g., TAT or TAC); nucleotides 3614 to 3616 of SEQ ID NO: 3 (e.g., TAT or TAC); nucleotides 4422 to 4424 of SEQ ID NO: 1 (e.g., TCT, TCC, TCA, TCG, AGT, AGC, ACT, ACC, ACA, ACG, CAT, or CAC); nucleotides 3659 to 3661 of SEQ ID NO: 3 (e.g., TCT, TCC, TCA, TCG, ACT, ACC, ACA, ACG, CAT, or CAC); nucleotides 4431 to 4433 of SEQ ID NO: 1 (e.g., TCT, TCC, TCA, TCG, AGT, or AGC); nucleotides 3668 to 3670 of SEQ ID NO: 3 (e.g., TCT, TCC, TCA, TCG, AGT, or AGC); nucleotides 4449 to 4451 of SEQ ID NO: 1 (e.g., ATG); nucleotides 3686 to 3688 of SEQ ID NO: 3 (e.g., ATG); nucleotides 4452 to 4454 of SEQ ID NO: 1 (e.g., GGT, GGC, GGA, or GGG); nucleotides 3689 to 3691 of SEQ ID NO: 3 (e.g., GGT, GGC, GGA, or GGG); nucleotides 4497 to 4499 of SEQ ID NO: 1 (e.g., CAA or CAG); nucleotides 3734 to 3736 of SEQ ID NO: 3 (e.g., CAA or CAG); nucleotides 4503 to 4505 of SEQ ID NO: 1 (e.g., ATG); nucleotides 3740 to 3742 of SEQ ID NO: 3 (e.g., ATG); nucleotides 4515 to 4517 of SEQ ID NO: 1 (e.g., TCT, TCC, TCA, TCG, AGT, or AGC); nucleotides 3752 to 3754 of SEQ ID NO: 3(e.g., TCT, TCC, TCA, or TCG); nucleotides 4527 to 4529 of SEQ ID NO: 1 (e.g., GGT, GGC, GGA, GGG, ATT, ATC, ATA, AGA, AGG, GCT, GCC, GCA, or GCG); nucleotides 3764 to 3766 of SEQ ID NO: 3 (e.g., GGT, GGC, GGA, GGG, ATT, ATC, ATA, AGA, AGG, GCT, GCC, GCA, or GCG); nucleotides 4539 to 4541 of SEQ ID NO: 1 (e.g., AAA or AAG); nucleotides 3776 to 3778 of SEQ ID NO: 3 (e.g., AAA or AAG); nucleotides 4632 to 4634 of SEQ ID NO: 1 (e.g., AAA or AAG); nucleotides 3869 to 3871 of SEQ ID NO: 3 (e.g., AAA or AAG); nucleotides 4713 to 4715 of SEQ ID NO: 1 (e.g., GTT, GTC, GTA, or GTG); nucleotides 3950 to 3952 of SEQ ID NO: 3 (e.g., GTT, GTC, GTA, or GTG); nucleotides 4716 to 4718 of SEQ ID NO: 1 (e.g., TGT, TGC, TCT, TCC, TCA, TCG, AGT, or AGC); and nucleotides 3953-3955 of SEQ ID NO: 3 (e.g., TGT, TGC, TCT, TCC, TCA, or TCG); or a complement sequence thereof. The corresponding codons in the wild-type ALK nucleic acid sequence are: ACG at nucleotides 4362 to 4364 of SEQ ID NO: 1 and nucleotides 3599 to 3601 of SEQ ID NO: 3; CTG at nucleotides 4365 to 4367 of SEQ ID NO: 1 and nucleotides 3602 to 3604 of SEQ ID NO: 3; TGC at nucleotides 4377 to 4379 of SEQ ID NO: 1 and nucleotides 3614 to 3616 of SEQ ID NO: 3; ATC for nucleotides 4422 to 4424 of SEQ ID NO: 1 and nucleotides 3659 to 3661 of SEQ ID NO: 3; TTC for nucleotides 4431 to 4433 of SEQ ID NO: 1 and nucleotides 3668 to 3670 of SEQ ID NO: 3; GTT for nucleotides 4449 to 4451 of SEQ ID NO: 1 and nucleotides 3686 to 3688 of SEQ ID NO: 3; CGC for nucleotides 4452 to 4454 of SEQ ID NO: 1 and nucleotides 3689 to 3691 of SEQ ID NO: 3; CTG for nucleotides 4497 to 4499 of SEQ ID NO: 1 and nucleotides 3734 to 3736 of SEQ ID NO: 3; CTC for nucleotides 4503 to 4505 of SEQ ID NO: 1 and nucleotides 3740 to 3742 of SEQ ID NO: 3; GGA for nucleotides 4515 to 4517 of SEQ ID NO: 1 and nucleotides 3752 to 3754 of SEQ ID NO: 3; TCC for nucleotides 4527 to 4529 of SEQ ID NO: 1 and nucleotides 3764 to 3766 of SEQ ID NO: 3; GAG for nucleotides 4539 to 4541 of SEQ ID NO: 1 and nucleotides 3776 to 3778 of SEQ ID NO: 3; GAG for nucleotides 4632 to 4634 of SEQ ID NO: 1 and nucleotides 3869 to 3871 of SEQ ID NO: 3; ATT for nucleotides 4713 to 4715 of SEQ ID NO: 1 and nucleotides 3950 to 3952 of SEQ ID NO: 3; and GGA for nucleotides 4716 to 4718 of SEQ ID NO: 1 and nucleotides 3953-3955 of SEQ ID NO: 3 (indicated in bold and underlined in FIG. 8).

Non-limiting exemplary probes of the invention that hybridize to the antisense strand of an ALK or ALK-fusion nucleic acid that contains a sequence encoding a mutation corresponding to amino acid position 1196 (leucine to methionine substitution) of SEQ ID NO: 2 or 4 are: ggt-tcatcctgatggagctcatg (SEQ ID NO: 9); gttcatcctgatggagct-catgg (SEQ ID NO: 11); ttcatcctgatggagctcatggc (SEQ ID NO: 13); cggttcatcctgatggagctcat (SEQ ID NO: 15); ccggt-tcatcctgatggagctca (SEQ ID NO: 17); ggttcatcctgatggagct-catg (SEQ ID NO: 19); and cggttcatcctgatggagctcat (SEQ ID NO: 21).

One skilled in the art may design a variety or probes or primers to hybridize or amplify a nucleic acid sequence (e.g., mRNA or genomic DNA) that encodes an ALK protein, an ALK-fusion protein, a mutant ALK protein, or a mutant ALK-fusion protein containing a contiguous nucleic acid sequence that encodes any of the above-identified codons corresponding to the indicated codons in SEQ ID NO: 1 or SEQ ID NO: 3.

One skilled in the art may identify in a nucleic acid or protein sequence a residue (e.g., amino acid or nucleotide) or codon that corresponds to a residue or codon in SEQ ID NOS: 1-4 using a number of sequence alignment software programs (e.g., NCBI BLAST website). Such software programs may allow for gaps in the alignment of the compared sequences. Using such software, one skilled in the art may identify a nucleotide, amino acid, or amino acid that corresponding to a specific nucleotide, amino acid, or codon in SEQ ID NOS: 1-4.

Also provided by the present application are probes that include variations to the nucleotide sequences shown in SEQ ID NO: 1 or SEQ ID NO: 3, as long as such variations permit detection of the desired mutations in a nucleic acid that encodes an ALK or ALK fusion protein. For example, a probe can have at least 90%, at least 95%, or at least 98% sequence identity to a contiguous sequence of nucleotides present in SEQ ID NO: 1 or SEQ ID NO: 2.

Likewise, probes (e.g., 8 to 50 nucleotides in length) may be designed for use in situ hybridization (e.g., FISH), Southern blotting, Northern blotting, or gene array analysis, that specifically hybridize to a contiguous sequence within an ALK gene, an ALK fusion gene, or an mRNA encoding an ALK protein or an ALK fusion protein, that encodes one or more of the amino acids corresponding to: the amino acid at position 1151, the amino acid at position 1152, the amino acid at position 1156, the amino acid at position 1171, the amino acid at position 1174, the amino acid at position 1180, the amino acid at position 1181, the amino acid at position 1196, the amino acid at position 1198, the amino acid at position 1202, the amino acid at position 1206, the amino acid at position 1210, the amino acid at position 1241, the amino acid at position 1268, and the amino acid at position 1269 of SEQ ID NO: 2 or SEQ ID NO: 4. For example, the probes may be designed to hybridize to a contiguous sequence within the human full-length ALK (human ALK mRNA, Genbank Accession Nos: U62540 and U66559 (SEQ ID NOS: 1 and 3, respectively)), human ALK fusion proteins, a nucleic acid that contains a contiguous sequence of between 60 and 1626 nucleotides that is at least 95% identical to a corresponding sequence in SEQ ID NO: 1 or SEQ ID NO: 3, or a nucleic acid (e.g., mRNA) encoding a mutant ALK or ALK fusion protein (as described herein), or the complement sequence thereof.

Computer software for the design of primers and probes are publicly available, for example, at the NCBI website. The Gene Infinity website also provides a listing of publicly available software programs for the design of probes and primers. Once the appropriate primer or probe sequences have been selected, the probes and primers may be synthesized using commercially available methods and equipment as described in the art (e.g., Koshkin et al., Tetrahedron 54:3607 (1998)). For example, the solid phase phosphoramidate method can be used to produce short LNA probes (Caruthers et al., Cold Spring Harbor Symp. Quant. Biol. 47:411 (1982)). Desirable LNA monomers and their methods of synthesis are also disclosed in U.S. Pat. Nos. 6,043,060 and 6,268,490.

Probes of the invention may further include any number of modifications. Probes may be labeled or conjugated to other functional moieties, e.g., through the attachment of duplex-stabilizing agents such as minor-groove-binders (MGB) or intercalating nucleic acids (INA). Additionally, the modifications may also include addition of non-discriminatory bases, e.g., such as 5-nitroindole, which are capable of stabilizing duplex formation regardless of the nucleobase at the opposing position on the target strand. The modifications may also include the addition of naturally and non-naturally occurring nucleobases including those disclosed in U.S. Pat. No. 3,687,808, in Englisch et al., Angewandte Chemie, International Edition 30:613-722, 1991, and in WO 97/12896.

The probes and primers of invention may contain one or more nucleotide analogue monomers (e.g., LNA) in order to increase the sensitivity and specificity of the primers or probes to bind to the target sequence. For example, the probes and primers of the invention may contain LNA, such as oxy-LNA (e.g., beta-D-oxy-LNA). In the probe or the primer, two nucleotide analogues may be spaced 2, 3, or 4 nucleotides apart. Desirably, the probes of the invention may be modified to have stable modified nucleotides at the 5' and 3' ends of the primer or the probe with nucleotides having phosphodiester or phosphorothioate bonds in the center of the probe to enhance probe stability in a cellular environment (Kang et al., Nucleic Acids Res. 32:4411 (2004); and U.S. Patent Application No. 2005/0203042).

The primers and probes of the invention may also contain a modified backbone (e.g., a nucleotide backbone structure other than the naturally occurring ribose-phosphate or deoxyribose-phosphate backbone). Exemplary modified backbones include a ribonucleotide moiety that is substituted at the 2'-position. The substituents at the 2'-position may, for example, be a saturated, unsaturated, unbranched, or branched C1 to C4 alkyl group, e.g., 2'-O-methyl ribose. Another suitable example of a substituent at the 2' position of a modified ribonucleotide moiety is a C1 to C4-alkoxy-C1 to C4 alkyl group. Another modification is a ribonucleotide that is substituted at the 2'-position with a fluoro group.

The probe or primers may also include a further 5' and/or 3'amino group, a 5' and/or 3' ligand, and/or a 5' and/or 3' label, e.g., a fluorescent label (e.g., fluorescein), a radioactive label, or a label that is a complex including an enzyme (e.g., a complex containing digoxigenin). The probe or primer is for example 8 to 30 nucleotides long (e.g., 8 to 50 nucleotides, 8 to 40 nucleotides, 8 to 30 nucleotide, or 8 to 20 nucleotides). An attached ligand may be a drug or a ligand that can be bound by an antibody. Exemplary ligands include biotin, digoxigenin (DIG), and functional groups such as: aromatic groups, heteroaromatic groups, carboxylic acids, carboxylic acid esters, carboxylic acid halides, carboxylic acid azides, carboxylic acid hydrazides, sulfonic acids, sulfonic acid esters, sulfonic acid halides, semicarbizides, thiosemicar-bazides, aldehydes, ketones, primary alcohols, phenols, alkyl halides, thiols, disulphides, primary amines, secondary amines, tertiary amines, hydrazines, epoxides, maleimides, C1-C20 alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-α-alanine, polyglycine, polylysine, peptides, oligo/polysaccharides, toxins, antibiotics, cell poisons, steroids, and affinity ligands, i.e., functional groups or biomolecules that have a specific affinity for sites on particular proteins, antibodies, poly- and oligosaccharides, and other biomolecules. One or more ligands that increase cell membrane permeability may also be included in the probes. Exemplary ligands that increase cell membrane permeability include lipophilic groups (e.g., sterols such as cholesterols, lanosterol, phytosterols, adamantols, fatty acids), peptides (e.g., cell penetrating peptides), charged moieties, functionalized alkyls, functionalized heteroalkyls, or other moieities assisting cellular uptake of oligonucleotides passively or actively.

Probes or primers of the invention may include single labels or a plurality of labels, e.g., a pair of labels that interact with each other either to produce a signal or to produce a change in a signal when hybridized to a target sequence. The probe or primer may include a fluorophore moiety and a quencher moiety, positioned in such a way that the hybridized state of the probe can be distinguished from the unhybridized state of the probe by an increase in the fluorescent signal from the probe or primer. The probe or primer may have, in addition to a sequence that hybridizes to a sequence in a target molecule, first and second complementary sequences which specifically hybridize to each other when the probe or primer is not hybridized to a sequence in a target molecule, bringing the quencher molecule in sufficient proximity to the report molecule to quench fluorescence of the reporter molecule. Hybridization of the target molecule distances the quencher from the fluorophore moiety and results in a signal proportional to the amount of hybridization.

Labels as used herein refer to any atom or molecule which can be used to provide a detectable (preferably quantifiable) signal and which can be attached to the probe or primer of the invention. Labels may provide signals detectable by fluorescence, radioactivity, colorimetric (UV/vis spectroscopy), X-ray diffraction or absorption, magnetism, enzymatic activity, and the like or adhere to complexes that generate such signals. The label may be detectable either by itself or as a part of a detection series. Non-limiting examples of functional parts of labels are biotin, digoxigenin (DIG), fluorescent groups (groups which are able to absorb electromagnetic radiation, e.g., light or X-rays, of a certain wavelength, and which subsequently re-emits the energy absorbed as radiation of longer wavelength, e.g., DANSYL (5-dimethylamino)-1naphthalenesulfonyl), DOXYL (N-oxyl-4,4-dimethyloxazolidine), PROXYL (N-oxyl-2,2,5,5-tetramethylpyrrolidone), TEMPO (N-oxyl-2,2,6,6-tetramethylpiperidine), dinitrophenyl, acridines, coumarins, Cy3, and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, rare earth metals, radioisotopic labels, chemiluminescence labels, and spin labels. Desirable labels include biotin, fluorescein, Texas Red, rhodamine, dinitrophenyl, digoxigenin, Ruthenium, Europium, Cy5, and Cy3.

Many synthetic approaches may be used to add the above moieties, ligands, and labels to probes and primers. The flexibility of the phosphoroamidite synthesis approach facilitates the production of probes and primers carrying all commercially available linkers, fluorophores, and labeling-molecules available for this standard chemistry. Probes and primers may also be labeled by enzymatic reactions, e.g., by phosphorylation using T4 polynucleotide kinase and gamma-$^{32}$P-ATP or by using terminal deoxynucleotidyl transferase (DTT) and any given digoxigenin-conjugated nucleotide triphosphate (dNTP) or dideoxynucleotide triphosphate (ddNTP).

In a specific example, a mutation-specific probe, as described herein, includes an acceptor fluorophore quencher at one end of the probe and a donor fluorophore at the other end of the probe. In this example, the probe does not emit significant donor emission when hybridized to the target nucleic acid molecule (because the quence is in sufficient proximity to the donor to reduce fluorescence emission by the donor), and the donor emission increases when the hybridization complex is disrupted during melting. Therefore, presence of the target target nucleic acid (containing the ALK mutation) can be detected by forming a hybridization complex between a mutation-specific probe containing both a quencher and a donor fluorophore, then increasing the temperature sufficient to melt or disrupt the hybridization complex, and monitoring the melting curve to determine if a target mutation is present. When using such a mutation-specific probe, an anchor probe is not needed to practice the method of identifying a mutation.

The invention further provides compositions containing a mutation-specific probe and an anchor probe. In particular examples, the composition includes a first nucleic acid probe and a second nucleic acid probe, wherein each probe includes a different fluorophore, such as a FRET pair (for example, when one of the probes includes a FRET donor and the other includes a FRET acceptor). If desired, the end of the probe not including the fluorophore can be blocked to significantly decrease extension (for example, if the probes are included in an amplification reaction). One of the probes is referred to as a mutation-specific probe (first probe), the other is referred to as an anchor probe (second probe), which is generally longer than the mutation-specific probe. The probes recognize adjacent sequences in ALK or ALK-fusion nucleic acids (e.g., adjacent nucleic acid sequences encoding the kinase domain of an ALK or ALK-fusion nucleic acid). The first probe (mutation-specific probe) hybridizes to the nucleic acid sequence encoding one or mutations in the ALK or ALK-fusion protein. The anchor probe (second probe) hybridizes to a sequence downstream of the nucleic acid sequence encoding the one or more mutations recognized by the mutation-specific probe (first probe). For example, the probes can be separated by at least 1 nucleotide, such as 1-2 nucleotides. The mutation-specific probe can be designed so that a single base mismatch (such as a nucleotide substitution encoding for a mutation) will result in a melting temperature ($T_m$) shift of at least 3° C., such as 4° C., at least 6° C., or at least 8° C., such as 4-10° C.

Particular examples of mutation-specific probes are described herein and include probes having at least 90%, 95%, 98%, or 99% identity to a nucleotide sequence corresponding to a nucleic acid sequence that encodes the kinase domain of an ALK or ALK-fusion gene (nucleotides 4083 to 5795 of SEQ ID NO: 1 or nucleotides 3320 to 5032 of SEQ ID NO: 3), or the complement sequence thereof. The anchor probe (second probe) may contain a donor fluorophore (thereby permitting detection of the change in acceptor fluorophore emission during melting) or may contain an acceptor fluorophore (thereby permitting detection of the change in acceptor fluorophore emission on the anchor probe during melting, wherein a decrease in acceptor fluorophore emission indicates that the mutation-specific probe is no longer hybridized to the target nucleic acid). Non-limiting examples of mutation-specific probes and anchor probes that hybridize to the antisense sequence of a nucleic acid encoding a codon corresponding to nucleotides 4497 to 4499 of SEQ ID NO: 1 or 3734 to 3736 of SEQ ID NO: 3 are: ggttcatcctgatggagctcatg (SEQ ID NO: 9)/cgggggggagacctcaagtccttcctcc (SEQ ID NO: 10); gttcatcctgatggagctcatgg (SEQ ID NO: 11)/gggggggagacctcaagtccttcctccg (SEQ ID NO: 12); ttcatcctgatggagctcatggc (SEQ ID NO: 13)/gggggagacctcaagtccttcctccga (SEQ ID NO: 14); cggttcatcctgatggagctcat (SEQ ID NO: 15)/gcgggggggagacctcaagtccttcctc (SEQ ID NO: 16); ccggttcatcctgatggagctca (SEQ ID NO: 17)/ggcgggggggagacctcaagtccttcct (SEQ ID NO: 18); ggttcatcctgatggagctcatg (SEQ ID NO: 19)/gggggggagacctcaagtccttcctccg (SEQ ID NO: 20); and cggttcatcctgatggagctcat (SEQ ID NO: 21)/cgggggggagacctcaagtccttcctcc (SEQ ID NO: 22).

The probe sequence can be varied slightly by moving the probes a few nucleotides upstream or downstream from the nucleotide positions that hybridize in the target ALK or ALK-fusion nucleic acid. However, the mutation-specific probe will target the one or more codons corresponding the mutant amino acids in ALK (SEQ ID NOS: 2 or 4) described above.

For example, the acceptor fluorophore can be attached to the 3'-end of the mutation-specific probe (first probe) and the donor fluorophore can be attached to the 3'-end of the anchor probe. Appropriate donor/acceptor fluorophore pairs can be selected using routine methods. In one example, the donor emission wavelength is one that can significantly excite the acceptor, thereby generating a detectable emission from the acceptor. Non-limiting examples of donor/acceptor FRET pairs include fluorescein as the donor and LightCycler Red 640 (LC-Red 640), LC-Red 705, JA286, Cy5, or Cy5.5 as the acceptor.

The acceptor fluorophore can be a dark quencher that significantly decreases the detectable emission when in sufficient proximity to the donor fluorophore. With this approach, when the mutation-specific probe and the anchor probe are hybridized to the target ALK or ALK-fusion nucleic acid, no significant donor emission signal is detected. However, during melting, when the probes are released from the target ALK or ALK-fusion nucleic acid, the emission signal from the donor increases, because it is no longer quenched by the dark quencher. Exemplary dark quenchers include Dabcyl, QSY7, QSY33, BLACK HOLE QUENCHERS™, ECLIPSE™, and IOWA BLACK™.

The probes of the invention may be covalently bonded to a solid support, e.g., by reaction of a nucleoside phorphoramidite with an activated solid support, and subsequent reaction of a nucleoside phosphoramide with an activated nucleotide or nucleic acid bound to the solid support. Preferably, the solid support or the oligonucleotide probe bound to the solid support is activated by illumination, a photogenerated acid, or electric current. The oligonucleotide probe may contain a spacer, e.g., a randomized nucleotide sequence or a non-base sequence, such as hexaethylene glycol, between the reactive group and the rest of the oligonucleotide probe. Such covalently bonded oligonucleotide probes are highly useful for large-scale detection and expression profiling of mRNA expression. The probes may also have a photochemically active group, a thermochemically active group, a chelating group, a reporter group, or a ligand that facilitates the direct or indirect detection of the probe or the immobilization of the probe onto a solid support. The photochemically active group, the thermochemically active group, the chelating group, the reporter group, or the ligand may include a spacer having a chemically cleavable group; or the thermochemically active group, the chelating group, the reporter group, or the ligand may be attached via the biradical of at least one of the nucleotide analogues of the probe.

The solid support may contain a material, e.g., selected from borosilicate glass, soda-lime glass, polysterene, polycarbonate, polypropylene, polyethylene, polyethylene-glycol terephthalate, polyvinylacetate, polyvinylpyrrolidinone, polymethylmethacrylate and polyvinylchloride, preferably polystyrene and polycarbonate. The solid support may be in the form of a specimen tube, a vial, a slide, a sheet, a film, a bead, a disc, a plate, a ring, a rod, a net, a filter, a tray, a microtiter plate, a stick, or a multi-bladed stick.

One or more probes or primers of the invention may be assembled in a kit with packaging and/or labeling to provide instructions for the identification of a mutation in an ALK gene, an ALK-fusion gene, or an mRNA encoding an ALK protein or an ALK-fusion protein. The kits provided by the invention may be used to isolate, purify, amplify, detect, identify, quantify, or capture a nucleic acid encoding an ALK gene, an ALK-fusion gene, or an mRNA encoding an ALK protein or an ALK-fusion protein. Desirably, the kits of the invention contain one or more probes and primers that specifically amplify or identify a contingous sequence in a nucleic acid (e.g., mRNA) encoding an ALK protein or an ALK fusion protein that encodes one or more of the amino acids corresponding to: the amino acid at position 1151, the amino acid at position 1152, the amino acid at position 1156, the amino acid at position 1171, the amino acid at position 1174, the amino acid at position 1180, the amino acid at position 1181, the amino acid at position 1196, the amino acid at position 1198, the amino acid at position 1202, the amino acid at position 1206, the amino acid at position 1210, the amino acid at position 1241, the amino acid at position 1268, and the amino acid at position 1269 of SEQ ID NO: 2 or SEQ ID NO: 4 (as described above), or the complementary sequence thereof.

Kits of the invention can include a pair of probes, such as a first probe (mutation-specific probe) and a second probe (anchor probe) (as described above), wherein the probes hybridize to adjacent regions in an ALK or an ALK-fusion nucleic acid. In particular examples, the probes are provided in separate vessels.

Kits of the invention can further include at least one other component, such as a component that can be used to amplify the target ALK or ALK-fusion nucleic acid or an ALK or ALK-fusion nucleic acid (control). Exemplary components include a pair of nucleic amplification primers (e.g., mutation-specific probe and an anchor probe), a polymerizing agent (e.g., a thermostable DNA polymerase), deoxynucleoside triphosphates, a buffer suitable for use in a nucleic acid amplification reaction, or combinations thereof. Particular examples of primers and probes that hybridize to or amplify an ALK or ALK-fusion nucleic acid encoding a mutant ALK or ALK-fusion protein are described above.

Once a mutation is identified using the methods of the invention (as is described above), the mutation is analyzed for association with an increased risk of developing a proliferative disorder. In this respect, the present invention provides a method of detecting the presence of a mutation in the human ALK gene in a biological sample.

Levels of ALK expression (e.g., DNA, mRNA, or protein) in a biological sample can be determined by using any of a number of standard techniques that are well known in the art or described herein. Exemplary biological samples include plasma, blood, sputum, pleural effusion, bronchoalveolar lavage, or biopsy, such as a lung biopsy and lymph node biopsy. For example, ALK expression in a biological sample (e.g., a blood or tissue sample) from a patient can be monitored by standard northern blot analysis or by quantitative PCR (see, e.g., Ausubel et al., supra; *PCR Technology: Principles and Applications for DNA Amplification*, H.A. Ehrlich, Ed., Stockton Press, NY; Yap et al., Nucl. Acids. Res. 19:4294 (1991)).

Mismatch detection assays also provide an opportunity to diagnose an ALK-mediated predisposition to a disease before the onset of symptoms. For example, a patient with an ALK mutation that suppresses normal ALK biological activity or expression may show no clinical symptoms of an ALK-related disease, and yet possess a higher than normal probability of developing a cancer. Given such a diagnosis, patients can take precautions to minimize their exposure to adverse environmental factors and to carefully monitor their medical condition (for example, through frequent physical examinations). As mentioned above, this type of diagnostic approach can also be used to detect ALK mutations in mutagenesis screens.

The ALK diagnostic assays described above can be carried out using any biological sample (for example, a blood, sputum, or tissue sample) in which ALK is normally expressed. Identification of a mutant ALK gene can also be assayed using these sources for test samples. Alternatively, an ALK mutation, particularly as part of a diagnosis for predisposition to an ALK-associated disease, can be tested for using a DNA sample from any cell, for example, by mismatch detection techniques. Preferably, the DNA sample is subjected to PCR amplification prior to analysis.

In yet another diagnostic approach of the invention, an immunoassay is used to detect or monitor ALK protein expression in a biological sample. ALK-specific polyclonal or monoclonal antibodies (produced as described below) can be used in any standard immunoassay format (e.g., ELISA, Western blot, or RIA; see, e.g., Ausubel et al., supra) to measure ALK or ALK fusion protein polypeptide levels. These levels are compared to wild-type ALK levels. For example, an increase in ALK production may be indicative of a condition or a predisposition to a condition involving increased ALK biological activity. Exemplary antibodies to detect ALK include highly specific monoclonal antibodies (see, e.g., Mino-Kenudson et al., Clin. Cancer Res. 16:1561 (2010), incorporated herein by reference); ALK1[23], ALKc[22], Clone 5A4 anti-ALK antibodies (Thermo Fisher Scientific, Fremont Calif.); and rabbit mAb ALK/p80 (clone SP8; Thermo Fisher Scientific) Immunohistochemical techniques can also be utilized for ALK detection. For example, a tissue sample can be obtained from a patient, sectioned, and stained for the presence of ALK using an anti-ALK antibody (see below) and any standard detection system (e.g., one that includes a secondary antibody conjugated to horseradish peroxidase). General guidance regarding such techniques can be found in, e.g., Bancroft et al., *Theory and Practice of Histological Techniques*, Churchill Livingstone, 1982, and Ausubel et al., supra.

In a preferred example, a combined diagnostic method can be employed that includes an evaluation of ALK protein production (for example, by immunological techniques or the protein truncation test (Hogerrorst et al., Nat. Genet. 10:208 (1995)), and a nucleic acid molecule-based detection technique designed to identify more subtle ALK mutations (for example, point mutations). As described above, a number of mismatch detection assays are available to those skilled in the art, and any preferred technique can be used. Mutations in ALK can be detected that either result in loss of ALK expression or loss of normal ALK biological activity.

Furthermore, antibodies against a protein produced by the gene included in the mutation, for example the ALK protein. Antibodies may be used to detect altered expression levels of the protein, including a lack of expression, or a change in its mobility on a gel, indicating a change in structure or size. In addition, antibodies may be used for detecting an alteration in the expression pattern or the sub-cellular localization of the protein. Such antibodies include ones that recognize both the wild-type and mutant protein, as well as ones that are specific for either the wild-type or an altered form of the protein, for example, one encoded by a polymorphic ALK gene. Monoclonal antibodies may be prepared using the ALK or ALK fusion proteins described above and standard hybridoma technology (see, e.g., Kohler et al., Nature 256:495 (1975); Kohler et al., Eur. J. Immunol. 6:511 (1976); Kohler et al., Eur. J. Immunol. 6:292 (1976); Hammerling et al., In *Monoclonal Antibodies and T Cell Hybridomas*, Elsevier, New York, N.Y., 1981; Ausubel et al., supra). Once produced, monoclonal antibodies are also tested for specific ALK protein recognition by Western blot or immunoprecipitation analysis (by the methods described in, for example, Ausubel et al., supra).

Antibodies used in the methods of the invention may be produced using amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (CABIOS 4:181 (1988)). These fragments can be generated by standard techniques, e.g., by the PCR, and cloned into the pGEX expression vector (Ausubel et al., supra). GST fusion proteins are expressed in *E. coli* and purified using a glutathione agarose affinity matrix as described in Ausubel et al. supra).

Synthesis

Compounds of formula I can be prepared using known methods and materials, e.g., as disclosed in detail in International patent applications WO 2004/080980, WO 2005/016894, WO 2006/021454, WO 2006/021457, WO 2009/143389, and WO 2009/126515. For instance, compounds of formula I in which $R^e$ is H and $R^d$ is H, Cl, $CF_3$, or $CH_3$, can be synthesized from 2,4-dichloropyrimidine, 2,4,5-trichloropyrimidine, 2,4-dichloro-5-(trifluoromethyl)pyrimidine, or 2,4-dichloro-5-methylpyrimidine, respectively, as described in PCT Publication No. WO/2009/143389 (see, for example, Schemes 1A and 1B below).

Scheme 1A

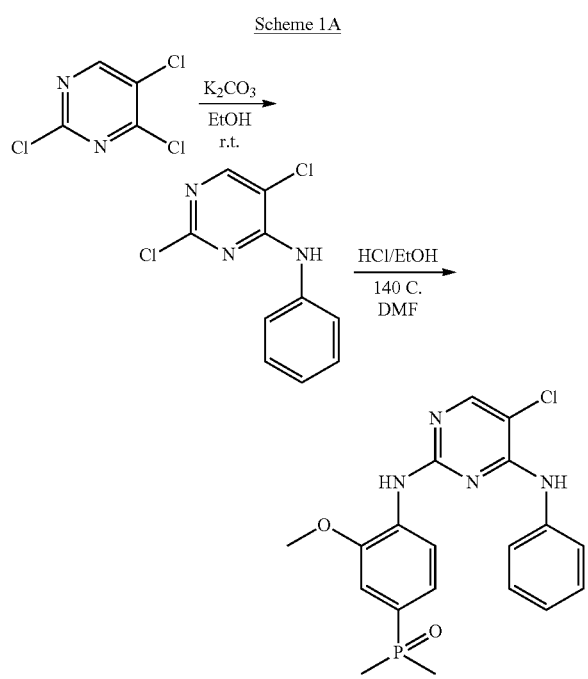

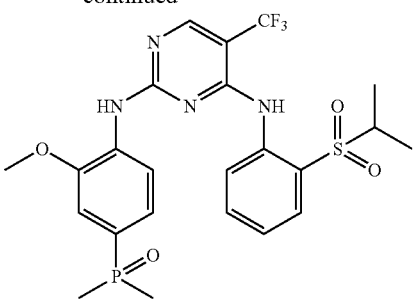

Compounds of formula I in which $R^d$ and $R^e$, together with the pyrimidine ring atoms to which they are attached, form a 5- or 6-membered ring containing one or two heteroatoms can be synthesized as described in PCT Publication No. WO2009/126515. See, for example, Scheme 2, which describes the synthesis of a starting material from which compounds of formula (I) can be synthesized. In Scheme 2, X is $CH_3$ or H.

Scheme 1B

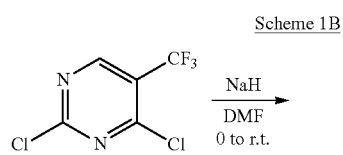

Scheme 2

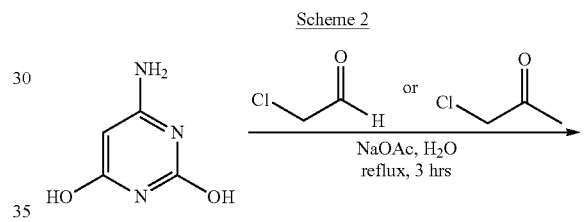

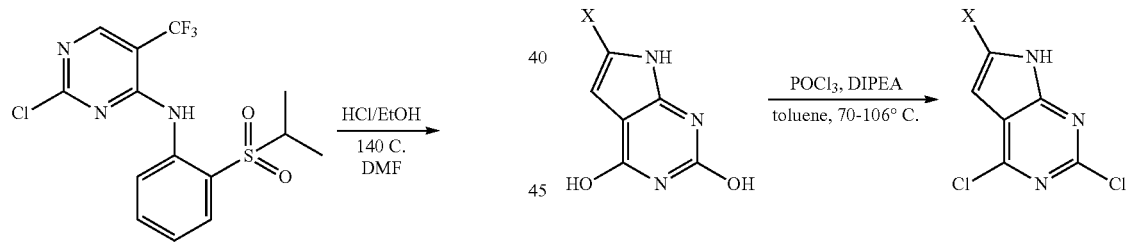

A detailed description for the synthesis of compound 1 is provided in Scheme 3.

Scheme 3

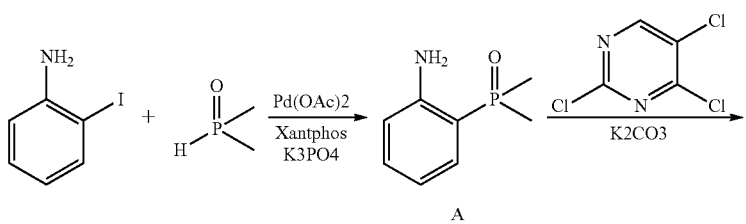

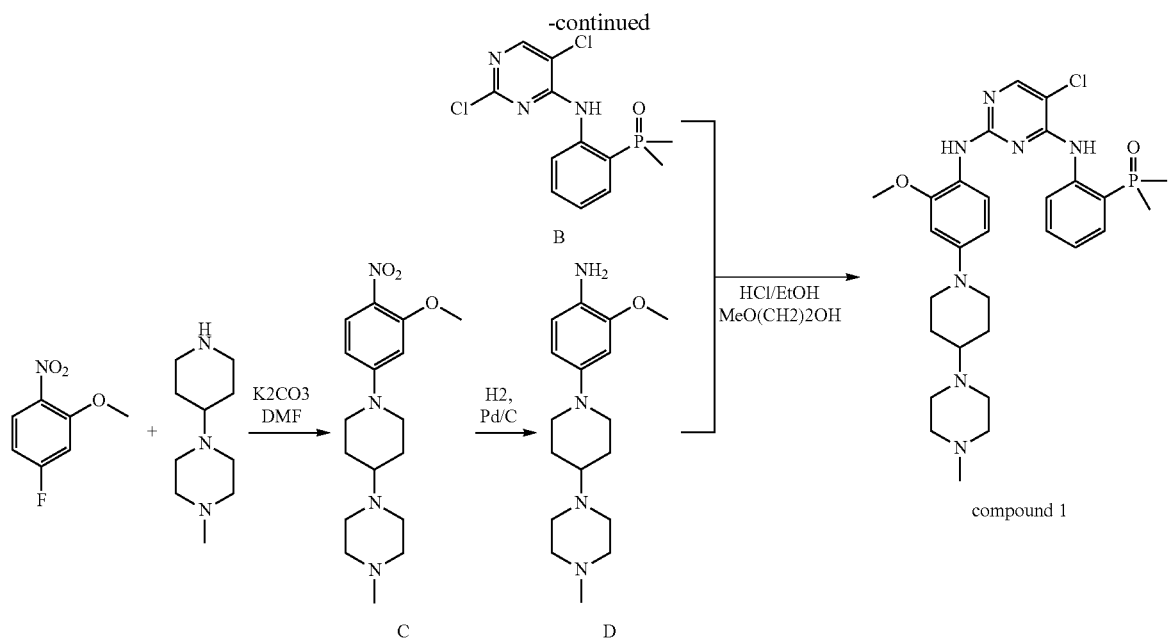

compound 1

Synthesis of A:

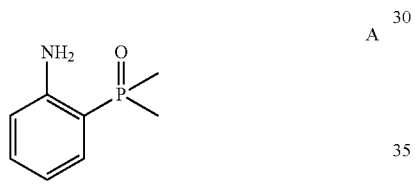

A

To a solution of 2-iodoaniline (1.0 eq) and dimethylphosphine oxide (1.1 eq) in DMF were added potassium phosphate (1.1 eq), palladium acetate/Xantphos (catalytic). The reaction was stirred at 150° C. for 3 hours and cooled to room temperature. The solvent was evaporated and the residue was worked up with DCM/water. The crude product was purified with a column (EtOAc/MeOH 10:1) to give A as a brown solid (80% yield).

Synthesis of B:

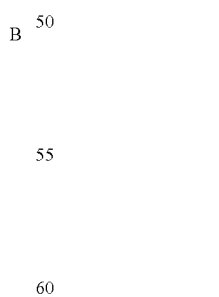

B 2,4,5-Trichloropyrimidine (1.57 eq), A (1.0 eq), and potassium carbonate (3.14 eq) in DMF were stirred at 60° C. for 5 hours and then cooled to r.t. The mixture was filtered and the filtrate was concentrated. The residue was purified with ISCO (DCM/MeOH 20:1) to give B as a yellow solid (61% yield).

Synthesis of C:

C

5-Fluoro-2-nitroanisole (1.0 eq), 1-methyl-4-(piperidin-4-yl)piperazine (1.0 eq), and potassium carbonate (2.0 eq) in DMF were stirred at 120° C. for 6 hours and then cooled to r.t. The mixture was filtered and evaporated. The crude product was crystallized from ethanol to give C as a yellow solid (72% yield).

Synthesis of D:

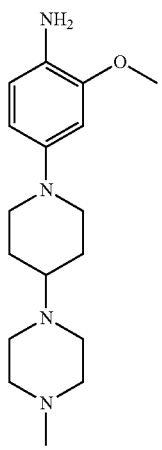

Palladium on activated carbon was added to a solution of C in ethanol under nitrogen. The suspension was then shaken under hydrogen (50 psi) for 3 hours. The mixture was filtered and the filtration was evaporated to give D as a purple solid in a quantitative yield.

Synthesis of compound 1:

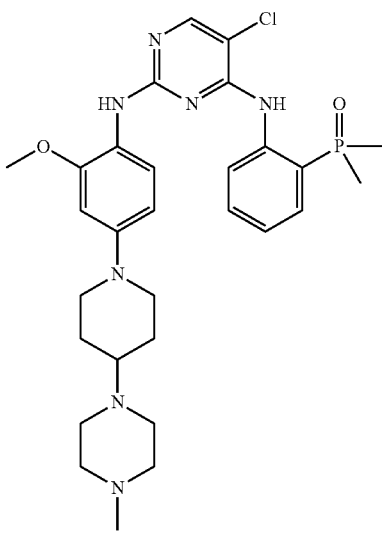

A solution of B (1.0 eq), D (1.4 eq), and 2.5 M HCl in ethanol (excess) in 2-methoxyethanol was sealed and heated at 120° C. with stirring for 5.5 hours and then cooled to r.t. The reaction was repeated 5 times and combined. The mixture was filtered and evaporated. Saturated $Na_2CO_3$ was added, followed by DCM with stirring strongly. The layers were separated and the aqueous layer was extracted with DCM. The organics were dried, evaporated and chromatographed [EtOAc/MeOH (7M ammonia) 20:1] to give a yellow solid. EtOAc was added and the suspension was refluxed for 30 minutes. After cooled to room temperature, filtration gave a solid, which was dissolved in DCM, filtered, and evaporated to afford compound 1 as an off-white solid (66% yield).

Formulation

Compounds of formula (I) can be formulated for any route of administration (e.g., orally, rectally, parenterally, intracisternally, intravaginally, intraperitoneally, topically (as by transdermal patch, powders, ointments, or drops), sublingually, bucally, as an oral or nasal spray) effective for use in the methods of the invention. For use in the methods of the invention, compounds of formula (I) are preferably formulated in dosage unit form for ease of administration and uniformity of dosage. For example, a compound of formula (I) can be formulated for as a capsule for oral administration containing nominally 10 mg, 50 mg, 100 mg, 150 mg, 250 mg, 500 mg, or any dosage amounts described herein as the free base or acid addition salt of compound 1 (e.g., the hydrochloride salt). The unit dosage forms of the invention can include compound 1, or a salt thereof, formulated with fillers, flow enhancers, lubricants, and/or disintegrants as needed. For example, a unit dosage form can include colloidal silicon dioxide (a flow enhancer), lactose anhydrous (a filler), magnesium stearate (a lubricant), microcrystalline cellulose (a filler), and/or sodium starch glycolate (a disintegrant). Compound 1 and the inactive ingredients can be formulated utilizing, for example, conventional blending, and encapsulation processes. Alternatively, compounds of formula (I) are formulated as described in PCT Publication Nos. WO2009/143389 and WO2009/126515.

Therapy

Compounds of formula (I) can be useful for treating ALK-driven cancers. In particular, the compounds can be useful for treating ALK-driven cancers that express ALK mutants and for treating ALK-driven cancers that are refractory to one or more of crizotinib, CH5424802 and ASP3026.

Such cancers can include, among others, cancers of the breast, non small cell lung cancer (NSCLS), neural tumors such as glioblastomas and neuroblastomas; esophaegeal carcinomas, soft tissue cancers such as rhabdomyosarcomas, among others); various forms of lymphoma such as a non-Hodgkin's lymphoma (NHL) known as anaplastic large-cell lymphoma (ALCL), various forms of leukemia; and including cancers which are ALK mediated.

In common with other RTKs, translocations affect the ALK gene, resulting in expression of oncogenic fusion kinases—the most common of which is NPM-ALK. For example, approximately sixty percent of anaplastic large cell lymphomas (ALCL) are associated with a chromosome mutation that generates a fusion protein consisting of nucleophosmin (NMP) and the intracellular domain of ALK. (Armitage et al., Cancer: principle and practice of oncology, 6$^{th}$ Edition, 2001, 2256-2316; Kutok et al., J. Clin. Oncol. 20:3691 (2002); and Wan et al., Blood 107:1617 (2006)). This mutant protein, NMP-ALK, possesses a constitutively active tyrosine kinase domain that is responsible for its oncogenic property through activation of downstream effectors (Falini et al., Blood, 94:3509 (1999); and Morris et al., Brit. J. Haematol. 113:275 (2001)). Experimental data have demonstrated that the aberrant expression of constitutuvely active ALK is directly implicated in the pathogenesis of ALCL and that inhibition of ALK can markedly impair the growth of ALK positive lymphoma cells (Kuefer et al., Blood 90:2901 (1997); Bai et al., Exp. Hematol. 29:1082 (2001); Slupianek et al., Cancer Res. 61:2194 (2001); and Turturro et al., Clin. Cancer Res. 8:240 (2002)). The constitutively activated chimeric ALK has also been demonstrated in about 60% of inflammatory myofibroblastic tumors (IMTs), a slow growing sarcoma that mainly affects children and young adults (Lawrence et al., Am. J. Pathol. 157:377 (2000)). Furthermore, recent reports have also described the occurrence of a variant ALK fusion, TPM4-ALK, in cases of squamous cell carcinoma (SCC) of the esophagus (Jazzi et al., World J. Gastroenterol. 12:7104 (2006); Du et al., J. Mol. Med. 85:863 (2007); and Aklilu M., Semin. Radiat. Oncol. 17:62 (2007)). Thus, ALK is one of the few examples of an RTK implicated in oncogenesis in both non-hematopoietic and hematopoietic malignancies. More recently it has been shown that a small inversion within chromosome 2p results in the formation of a fusion gene comprising portions of the echinoderm microtubule-associated protein-like 4 (EML4) gene and the anaplastic lymphoma kinase (ALK) gene in non-small-cell lung cancer (NSCLC) cells (Soda et al., Nature 448:561 (2007)).

The present invention is based in part upon the discovery that ALK-driven tumors can develop kinase domain mutations, which impair inhibitor binding. The present invention is also based upon the discovery that compounds of formula (I) can be used to treat ALK-driven cancers that express ALK mutants and for treating ALK-driven cancers that are refractory to one or more of crizotinib, CH5424802 and ASP3026. Compounds of formula (I) can also be used in a maintenance role to prevent recurrence of cancer in patients in need of such a treatment.

The effective systemic dose of a compound of formula (I) will typically be in the range of an average daily dose of from 10 mg to 2,000 mg of compound 1 per kg of patient body weight, administered in single or multiple doses. Generally, compound 1 may be administered to patients in need of such treatment in a daily dose range of about 50 to about 2,000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

When one or more of crizotinib, CH5424802 and ASP3026 is used in combination with a compound of formula (I), each component of the combination therapy may be administered at their monotherapy dosing levels and schedules. For example, crizotinib has been administered orally for the treatment of NSCLC at 250 mg BID.

The effective systemic dose of compound 1 will typically be in the range of an average daily dose of from 10 mg to 2,000 mg of compound 1 per kg of patient body weight, administered in single or multiple doses. Generally, compound 1 may be administered to patients in need of such treatment in a daily dose range of about 50 to about 2,000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

Alternatively, one or more of crizotinib, CH5424802 and ASP3026 is used in combination with a compound of formula (I) with a reduced dosing level in one or both components.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Experimental

Reagents: Compound 1 was synthesized by ARIAD Pharmaceuticals. Crizotinib was either synthesized by ARIAD Pharmaceuticals or purchased from Wuxi Howfond Biopharma, Co., Ltd., a chemical CRO company.

In vitro mutagenesis screen: Ba/F3 cells expressing native EML4-ALK were treated overnight with 100 µg/ml N-ethyl-N-nitrosourea (ENU, Sigma-Aldrich), pelleted, resuspended in fresh media, and distributed into 96-well plates at a density of $5*10^4$ cells/well in 200 µl media supplemented with graded concentrations of Compound 1 or crizotinib. The wells were observed for media color change and cell growth twice a week throughout the 28-35 day experiment. The content of outgrown wells were transferred to 24-well plates and expanded in media supplemented with Compound 1 or crizotinib at the same concentration as in the initial 96-well plate. At confluence, cells in 24-well plate were collected by centrifuge for DNA extraction and for further characterization. Genomic DNA was extracted from cell pellets using DNEasy 96 Blood & Tissue kit (Qiagen). The ALK kinase region was amplified using primer:

5'-AGCGATGCAGATGGAATTGCAGAG-3' and
5'-CAATAGGCAGCGCCGTGTTGATTA-3'.

PCR products were purified by QIAquick PCR purification kit (Qiagen) and sequenced by MGH DNA sequencing Core.

Mapping mutation sites onto model of inhibitor bind ALK: A homology model of ALK was built and optimized based on the crystal structure of activated insulin kinase (PDB code: 3irk) with Prime (Schrodinger software package). Crizotinib was docked into ALK by using the Glide SP procedure with refinement option (Schrodinger) and the top scored pose was chosen for further analysis.

Re-introduce mutation into Ba/F3 cells: pMSCVneo plasmid encoding EML4-ALK mutations were generated with QuickChange site-directed mutagenesis kit (Stratagene) according to manufacturer's instruction using pMSCVneo encoding native EML4-ALK as the template. Each mutation was confirmed by DNA sequencing. Ba/F3 cells expressing EML4-ALK mutants were generated by infecting Ba/F3 parental cells (supplemented with IL-3 in media) with retrovirus encoding EML4-ALK mutations followed by selection with G418 and cultured in the absence of IL-3.

In vitro viability assay: Ba/F3 parental and Ba/F3 cells expressing EML4-ALK either from ENU-isolated clones or from re-introduced lines were plated in 96-well plates and treated with compounds for 72 h. Cell viability (IC50) was assessed using CellTiter 96 AQueous One (Promega) and plotted as percent viable relative to vehicle treated cells using XLfit.

Inhibition of ALK phosphorylation: EML4-ALK expressing Ba/F3 cells either from ENU-isolated clones or from re-introduced lines were treated with increasing concentrations of Compound 1 or crizotinib for 2 hours. Cell lysates were prepared and loaded onto PathScan Sandwich ELISA kit (Cell Signaling) for p-ALK and for total ALK. IC50 was determined as the concentration of compound required to decrease ALK phosphorylation by 50% comparing to vehicle control.

In vivo efficacy: Ba/F3 cells expressing native or mutant EML4-ALK were implanted into the right flank of SCID Beige mice (10×10$^6$ cells/mice). When the average tumor volume reached ~200 mm$^3$, either vehicle or compound was administered by once daily oral gavage for 8-12 days. Mean tumor volume (±SE) was then calculated for each group.

Pharmacodynamics/Pharmacokinetics: For pharmacodynamic analysis, 6 or 24 hours after treating tumor-bearing mice with a single dose of vehicle or compound, tumors were collected, homogenized, and analyzed by ELISA. Inhibitor concentrations in plasma were determined by an LC/MS/MS method. Calibration standards were prepared in blank mouse plasma. Internal standards were added to all plasma samples and the samples were deproteinized before analysis.

Example 1

EML-4-ALK Mutants Recovered by Accelerated In Vitro Mutagenesis

Figure 2A:
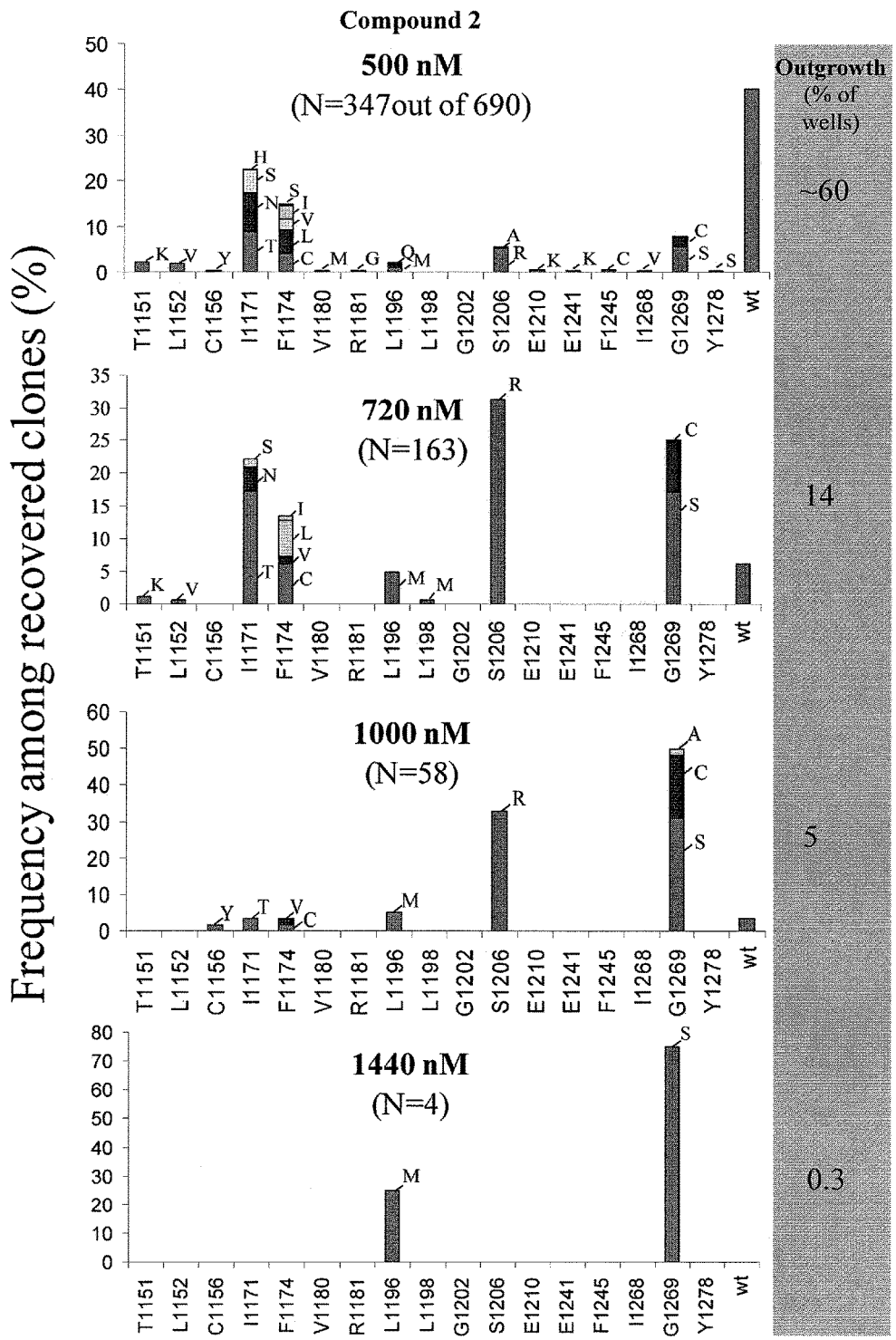
FIGS. 2A and 2B show an in vitro mutagenesis screen with frequency among recovered clones.
Figure 2B:
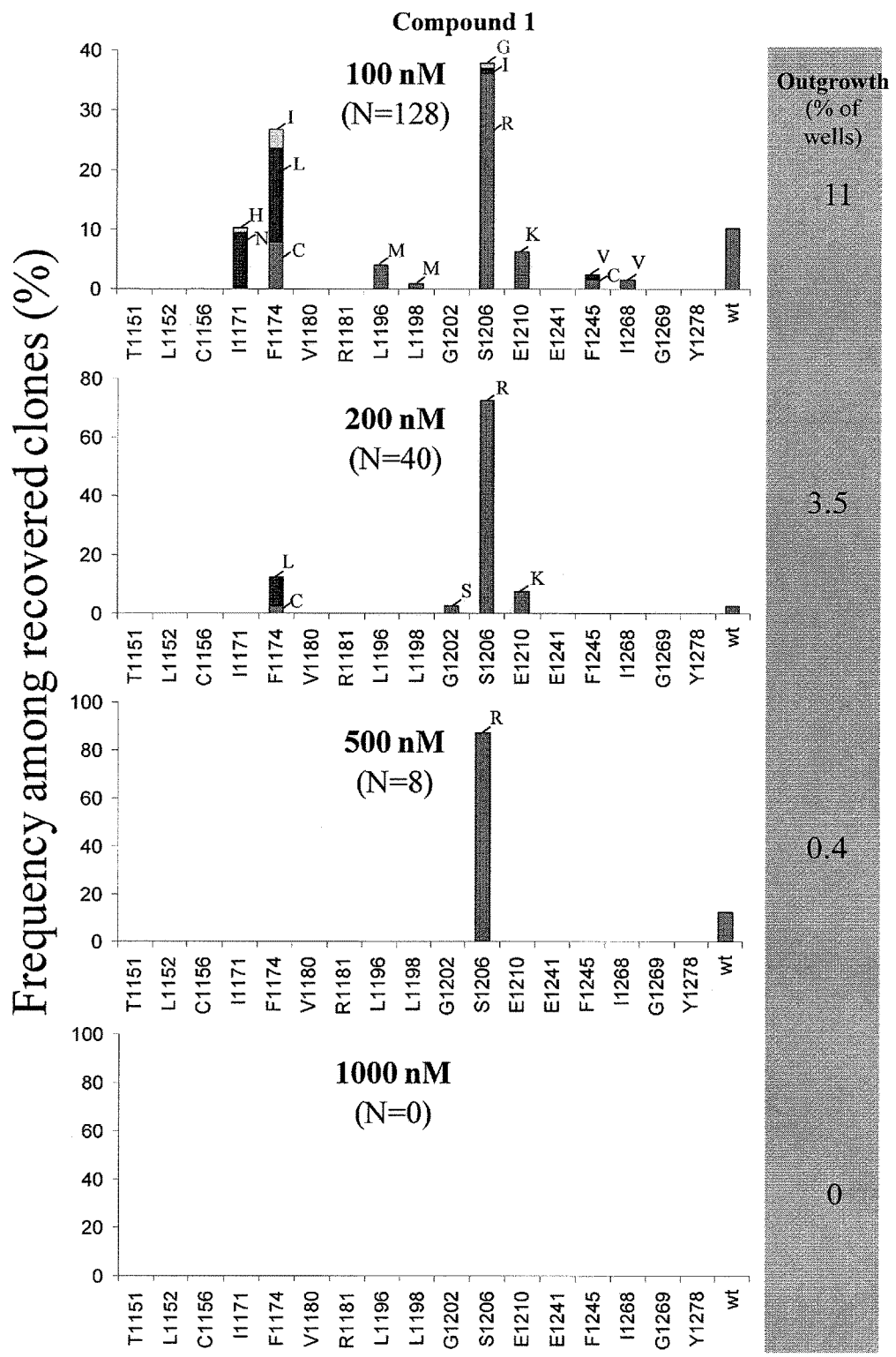
Figure 3:
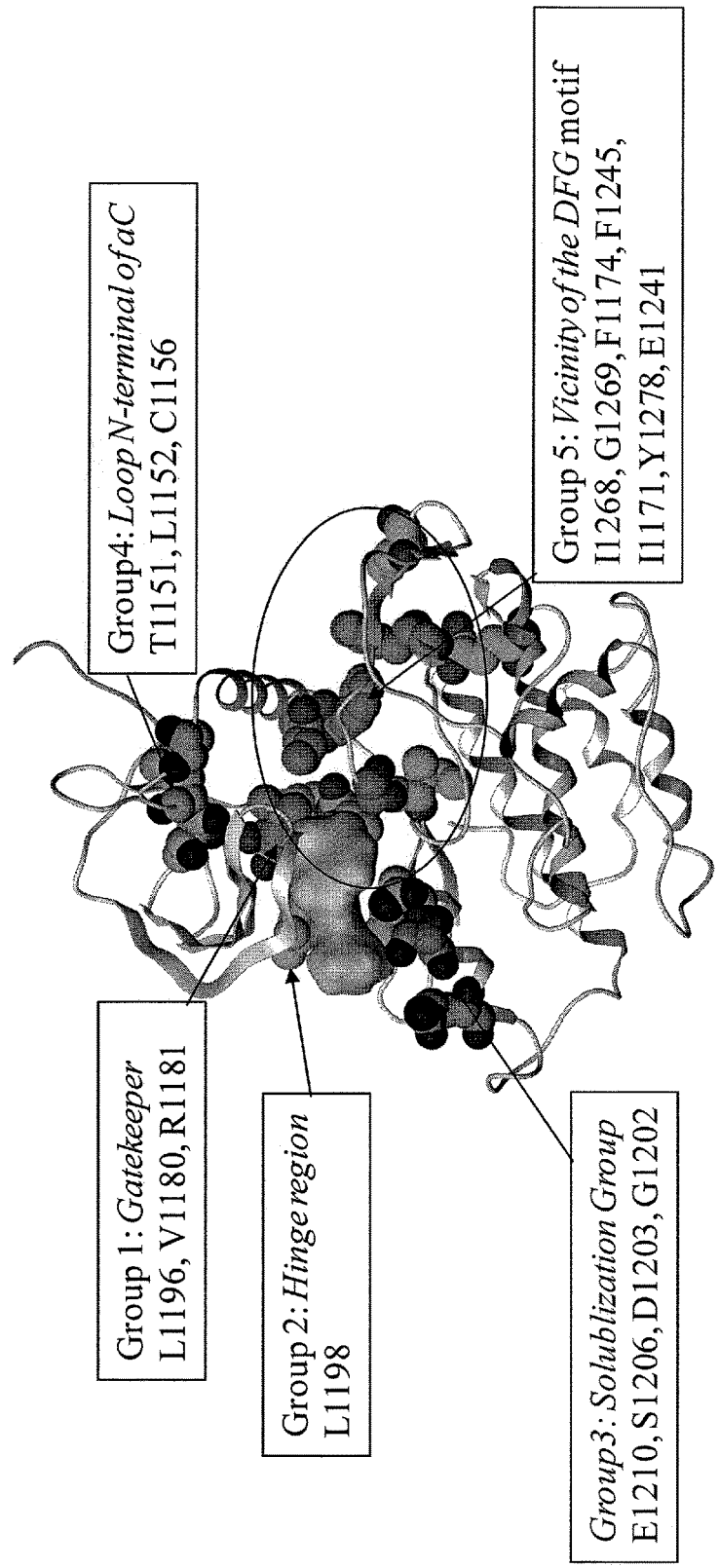
FIG. 3 is a homology model of crizotinib bound to ALK.

FIG. 1 provides a schematic illustration of accelerated in vitro mutagenesis. Details of this protocol are provided in the Experimental section above. EML4-ALK mutants were recovered in the presence of inhibitors, either Compound 1 or crizotinib. FIGS. 2A-2B provide the frequency among recovered clones for crizotinib (FIG. 2A) and for Compound 1 (FIG. 2B). Mutagenesis was repeated 2 additional times with similar results. With respect to Compound 1, one additional mutation (D1203N) was observed at 100 nM Compound 1 completely suppressed the emergence of resistance at 1000 nM, where two mutants were observed for crizotinib at 1440 nM. FIG. 3 is a model of crizotinib bound to ALK. Various groups are provided and mutation sites are provided, based on the interaction of crizotinib with ALK.

Example 2

In Vitro Inhibition of EML-4-ALK Mutants

Figure 4A:
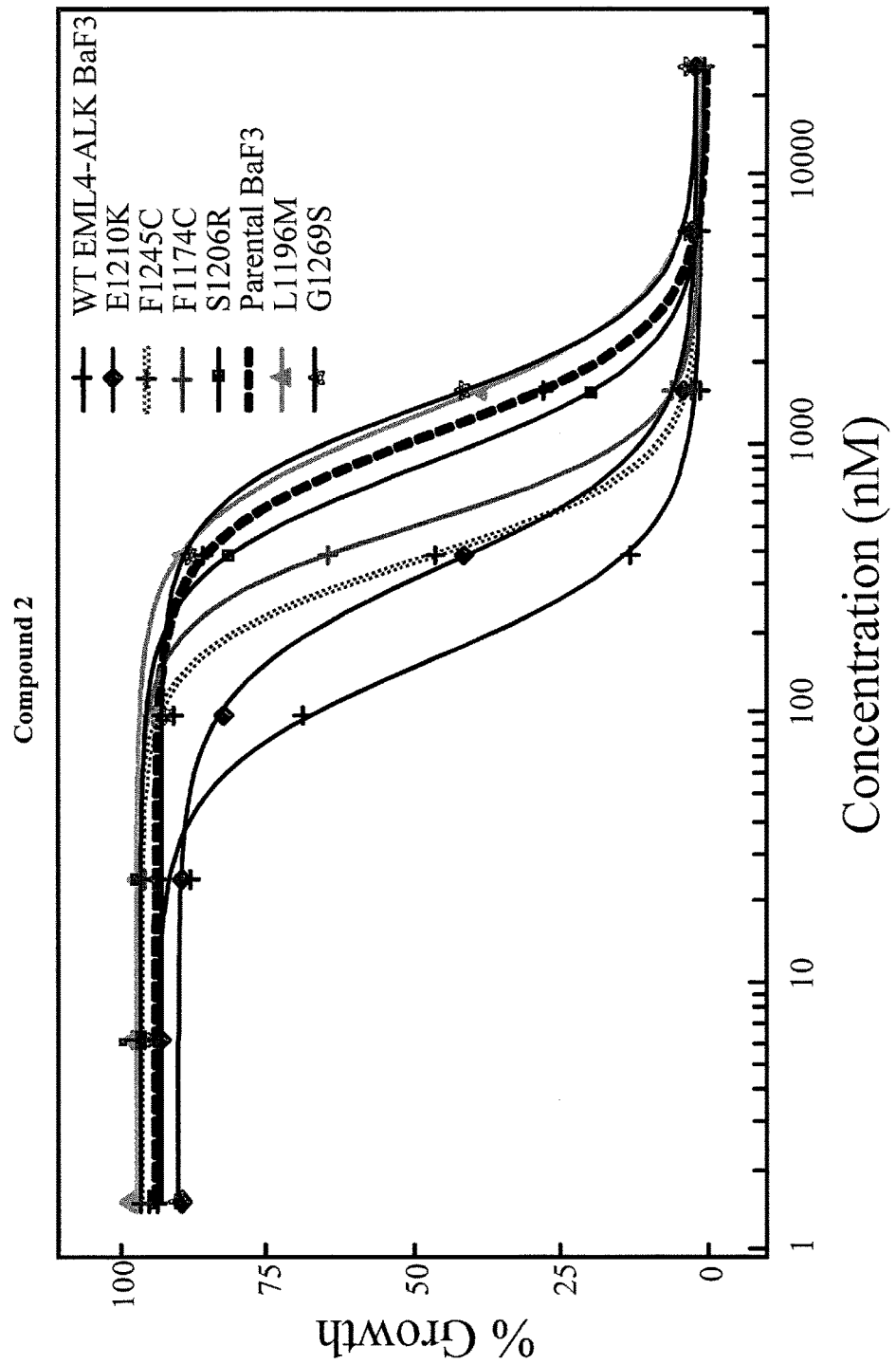
FIGS. 4A and 4B show the effect of compound 1 and crizotinib in a cellular proliferation assay with different EML-4-ALK mutants.
Figure 4B:
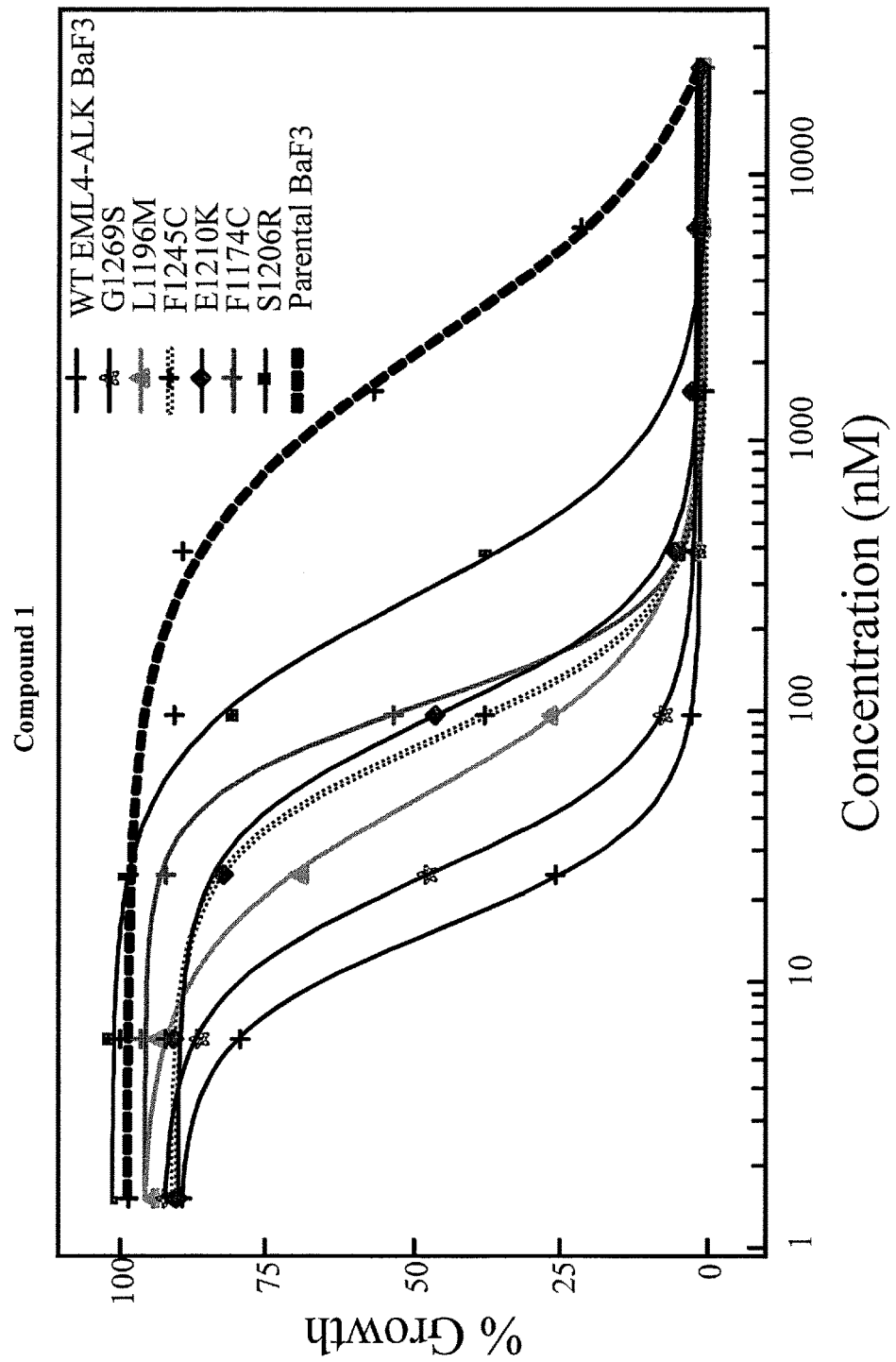

Compound 1 and crizotinib were assessed by using cellular proliferation assays. Table 1 shows IC50 values for Ba/F3 cellular proliferation assays. FIG. 4A shows a representative proliferation curve for crizotinib with different EML-4-ALK mutants. FIG. 4B shows a representative proliferation curve for Compound 1.

TABLE 1

IC50 values for Ba/F3 cellular proliferation assays

| Ba/F3 line | Compound 2 | | | Compound 1 | | |
|---|---|---|---|---|---|---|
| | IC50s (nM) | | TI** | IC50s (nM) | | TI** |
| Parental* | 1210 ± 334 | | 1 | 2189 ± 410 | | 1 |
| Nat veEML4-ALK | 139 ± 30 | | 9 | 11 ± 4 | | 205 |
| EML4-ALK Mutants: | ENU-clone | Re-introduced | | ENU-clone | Re-introduced | |
| 11171T | 395 ± 199 | 413 ± 62 | 3 | 22 ± 11 | 18 ± 4 | 102 |
| F1 174C | 478 ± 31 | 319 ± 90 | 3 | 68 ± 31 | 51 ± 14 | 32 |
| L1196M | 1131 ± 296 | 1215 ± 708 | 1 | 45 ± 23 | 40 ± 19 | 49 |
| S1206R | 711 ± 250 | 728 ± 362 | 2 | 194 ± 84 | 158 ± 86 | 1 |
| E1210K | 315 ± 124 | 297 ± 92 | 4 | 64 ± 33 | 86 ± 21 | 34 |
| F1245C | 41 ± 90 | 269 ± 194 | 3 | 44 ± 29 | 34 ± 28 | 50 |
| G1269S | 1141 ± 527 | 1196 ± 649 | 1 | 16 ± 6 | 16 ± 5 | 141 |

*Parental Ba/F3 cells lack EML4-ALK and therefore require IL-3 for growth.
**Therapeutic Index (TI) = Parental IC50 / EML4-ALK IC50.
(n = 5)

Compound 1 was also evaluated against crizotinib, ASP3026, and CH5424802 in a similar cellular proliferation assay, in this case using Ba/F3 cells expressing a different set of EML4-ALK mutations. In this study, the mutations are resistance-conferring ALK mutations identified by mutagenesis screening and/or from clinical samples of crizotinib-resistant cancers. The results are provided in Table 2.

TABLE 2

IC$_{50}$ (nM) values for Ba/F3 cellular proliferation assays

| Ba/F3 cell line | Compound 1 | crizotinib | ASP3026 | CH5424802 |
|---|---|---|---|---|
| Ba/F3 parental | 4580 ± 1553 | 2065 ± 373 | >10000 ± 0 | >10000 ± 0 |
| EML4-ALK | 17 ± 4 | 137 ± 49 | 129 ± 021 | 15 ± 8 |
| 1151 T insertion[1]* | 244 ± 16 | 1336 ± 4902 | 5939 ± 2278 | 455 ± 143 |
| L1152R* | 17 ± 5 | 911 ± 136 | 5934 ± 2156 | 105 ± 35 |
| C1156Y* | 150 ± 9 | 2323 ± 117 | 2555 ± 86 | 194 ± 39 |
| F1174L* | 95 ± 5 | 449 ± 117 | 978 ± 132 | 81 ± 4 |
| L1196M* | 99 ± 21 | 870 ± 143 | 1902 ± 448 | 220 ± 49 |
| G1202R* | 379 ± 68 | 874 ± 53 | 1856 ± 550 | 1009 ± 137 |
| D1203N* | 144 ± 8 | 693 ± 51 | 854 ± 164 | 85 ± 17 |
| S1206Y* | 88 ± 3 | 509 ± 85 | 518 ± 74 | 58 ± 11 |
| G1269A* | 24 ± 4 | 798 ± 62 | 264 ± 65 | 103 ± 15 |
| S1206A | 120 ± 29 | 391 ± 21 | 1679 ± 556 | 150 ± 23 |

TABLE 2-continued

IC$_{50}$ (nM) values for Ba/F3 cellular proliferation assays

| Ba/F3 cell line | Compound 1 | crizotinib | ASP3026 | CH5424802 |
|---|---|---|---|---|
| F1174V | 107 ± 37 | 347 ± 77 | 1662 ± 141 | 102 ± 60 |
| I1171S | 61 ± 8 | 348 ± 27 | 948 ± 60 | 1132 ± 313 |
| I1171N | 123 ± 29 | 586 ± 63 | 1201 ± 19 | >10000 |
| V1180L | 19 ± 4 | 201 ± 6 | 183 ± 13 | >10000 |

[1]Insertion of a threonine at position 1151. Mutations that were identified clinically as conferring resistance or were so identified by screening and later confirmed clinically are marked with *.

Figure 12:
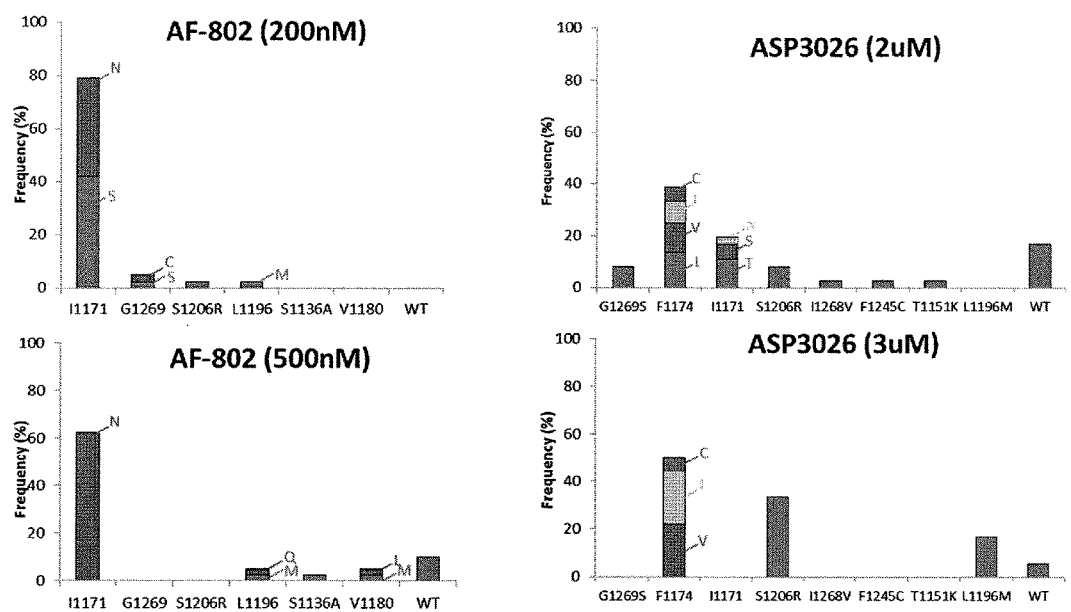
FIG. 12 is a series of bar graphs depicting the emergence of cells resistant to CH5424802 ("AF-802") and ASP3026. Selection of BaF3 cells expressing EML4-ALK using various concentrations of AF-802 and ASP3026 led to the identification of the mutations identified in the bar graphs. These compounds are susceptible to mutational weaknesses.

In addition to the mutations already known to confer crizotinib-resistance clinically, a number of mutations were observed that could also lead to tumors resistant to treatment with ASP3026 or CH5424802 (see FIG. 12). For example, the I1171N, I1171S, and V1180L mutants are particularly resistant to CH5424802. Importantly, in the case of compound 1, no ALK mutation, not even the 1151 T insertion, raises the IC$_{50}$ value for compound 1 beyond a trough concentrations achievable with clinically relevant doses of compound 1.

Compound 1 also inhibited ALK phosphorylation in Ba/F3 cell lines expressing the EML4-ALK mutations. Table 3 shows ALK phosphorylation in cell lysates from cell lines exposed to Compound 1 or crizotinib.

TABLE 3

ALK phosphorylation in Ba/F3 cell lines

| | Crizotinib | | Compound 1 | |
|---|---|---|---|---|
| EML4-ALK | IC50s (nM) | | IC50s (nM) | |
| Native | 74 ± 48 | | 5.3 ± 3.8 | |
| Mutants: | ENU-clone | Re-introduced | ENU-clone | Re-introduced |
| F1174C | 696 ± 514 | | 12 ± 4 | |
| L1196M | 1291 ± 704 | 817 ± 324 | 15 ± 8 | 7.6 ± 0.2 |
| S1206R | 1012 ± 347 | 172 ± 71 | 170 ± 135 | 17 ± 2 |
| E1210K | 335 ± 106 | | 76 ± 25 | |
| F1245C | 364 ± 223 | | 7 ± 4 | |
| G1269S | 1353 ± 733 | 1005 ± 24 | 17 ± 5 | 8.6 ± 0.1 |

(n = 2 or 3)

Example 3

In Vivo Inhibition of EML-4-ALK Mutants

Figure 5A:
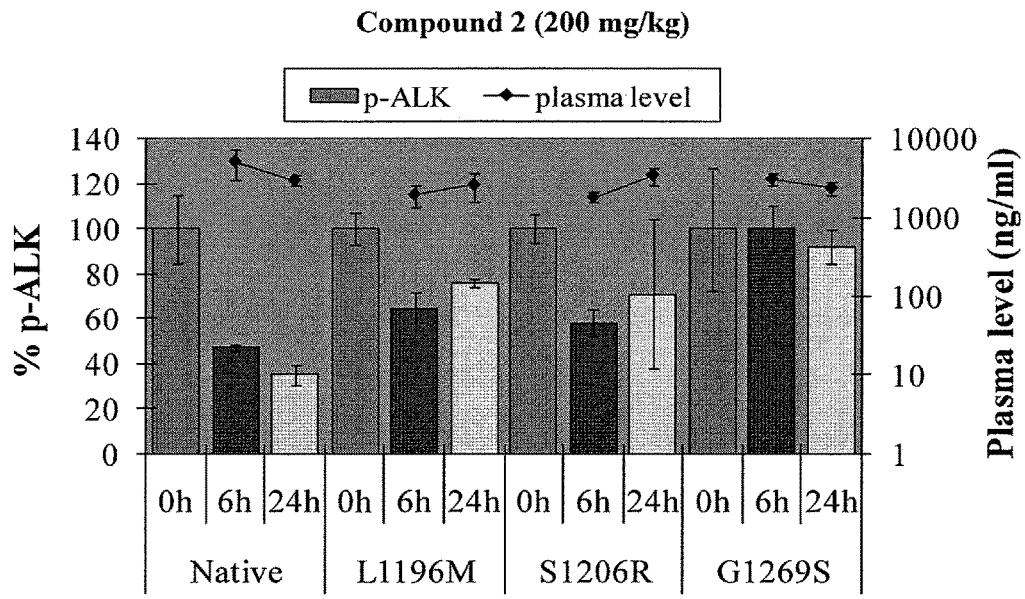
FIGS. 5A and 5B show the effect of compound 1 and crizotinib for ALK phosphorylation in EML4-ALK mutant tumors in vivo.
Figure 5B:
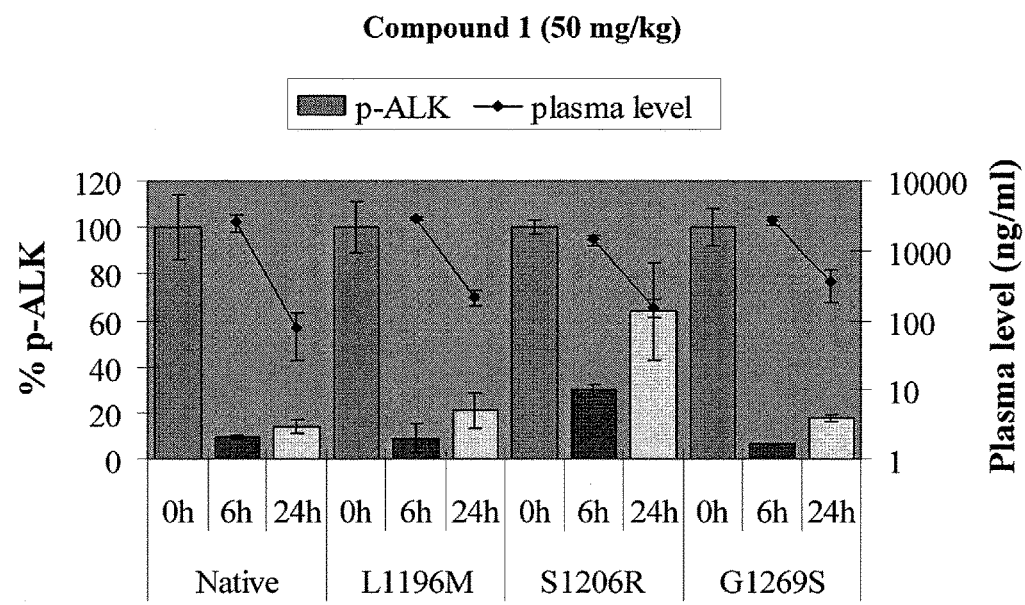
Figure 6A:
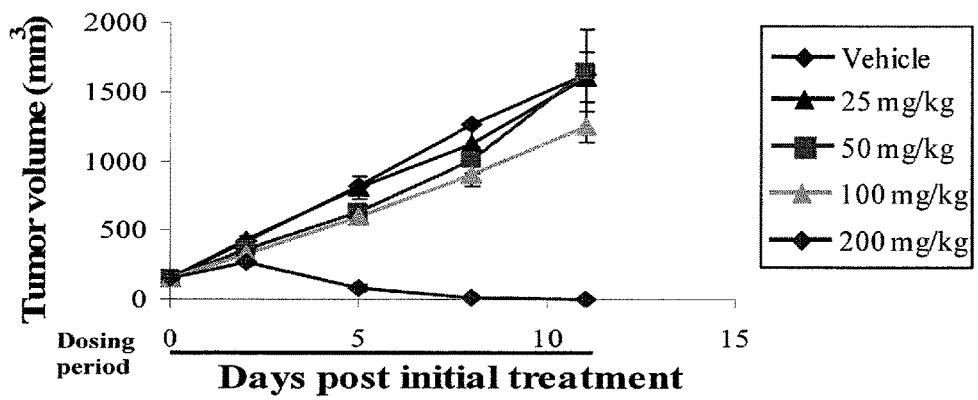
FIGS. 6A-6D show the effect of various dosages of crizotinib on a xenograft model. Data is provided for native EML4-ALK (FIG. 6A) and for the L1196M (FIG. 6B), S1206R (FIG. 6C), and G1269S (FIG. 6D) mutants.
Figure 6B:
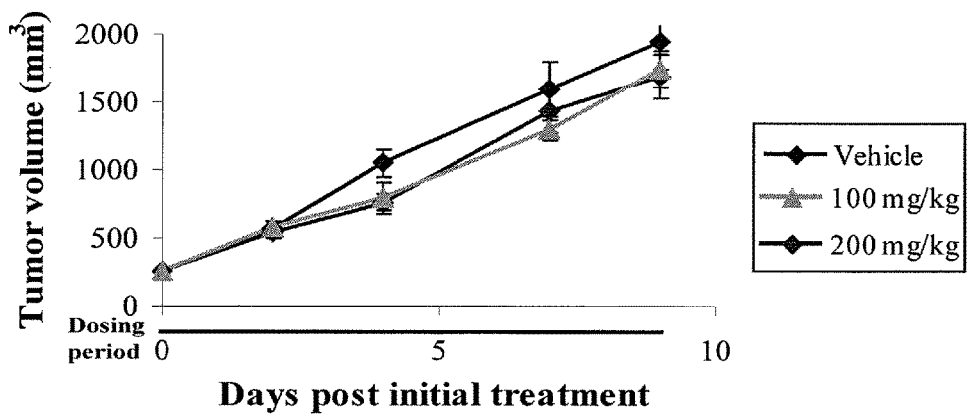
Figure 6C:
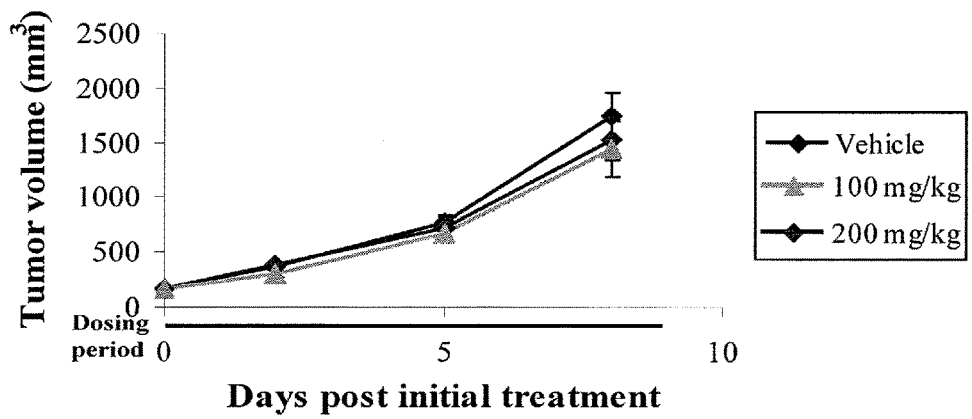
Figure 6D:
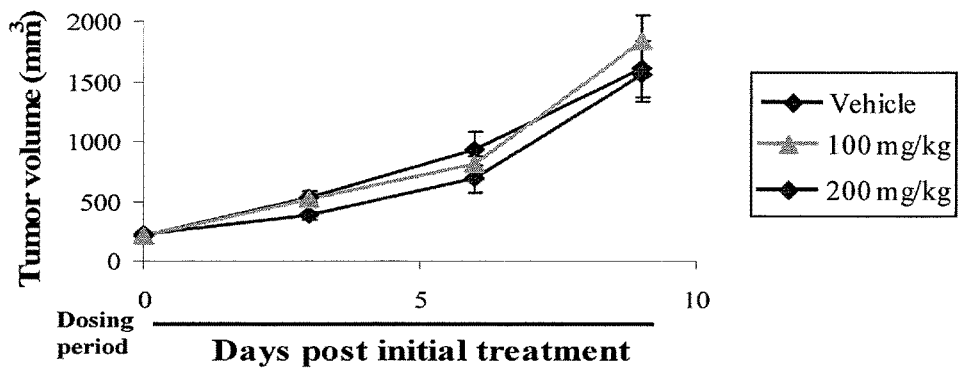
Figure 7A:
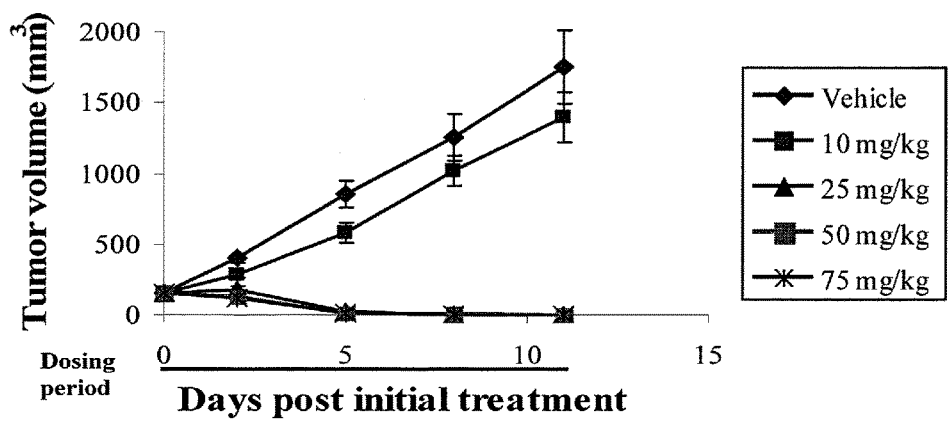
FIGS. 7A-7D show the effect of various dosages of compound 1 on a xenograft model. Data is provided for native EML4-ALK (FIG. 7A) and for the L1196M (FIG. 7B), S1206R (FIG. 7C), and G1269S (FIG. 7D) mutants.
Figure 7B:
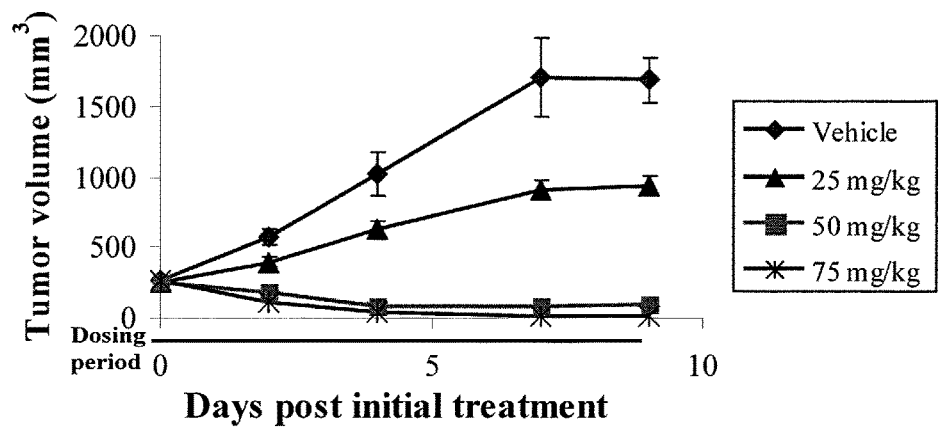
Figure 7C:
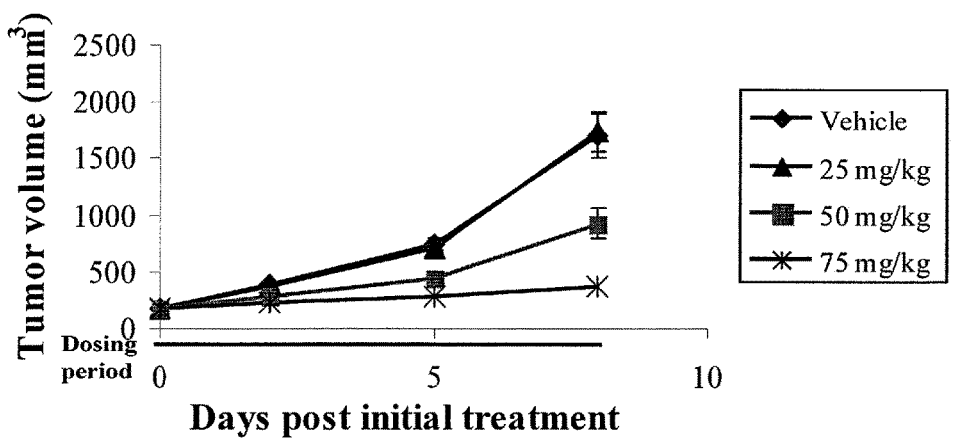
Figure 7D:
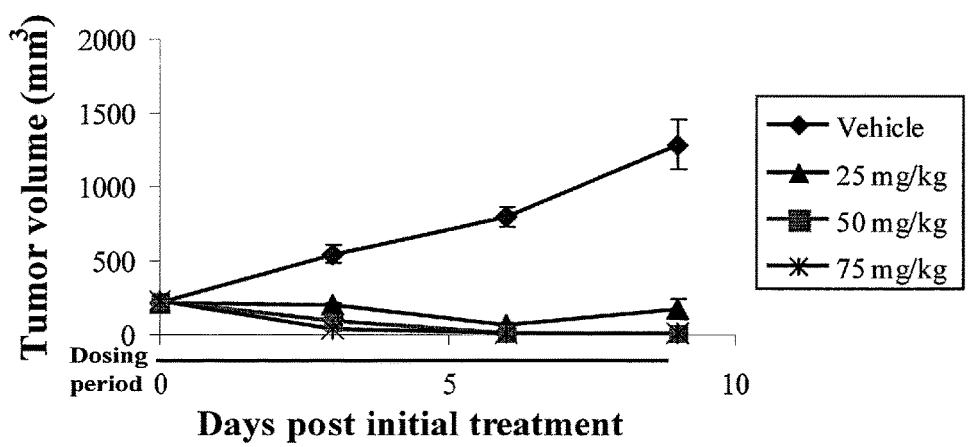

In vivo experiments for pharmacodynamics/pharmacokinetics were also conducted. FIG. 5A shows in vivo experiments for ALK phosphorylation in EML4-ALK mutant tumors in vivo, as well as inhibitors concentrations in plasma. As shown in FIG. 5B, Compound 1 inhibited ALK phosphorylation in EML4-ALK mutant tumors in vivo.

Xenograft models were also used to determine efficacy of Compound 1 and crizotinib. FIGS. 6A-6D shows tumor volume after treatment with crizotinib for native EML4-ALK (FIG. 6A) and for the L1196M (FIG. 6B), S1206R (FIG. 6C), and G1269S (FIG. 6D) mutants.

Compound 1 is efficacious in crizotinib-resistant EML4-ALK mutant mouse xenograft models. FIGS. 7A-7D shows tumor volume after treatment with Compound 1 for native EML4-ALK (FIG. 7A) and for the L1196M (FIG. 7B), S1206R (FIG. 7C), and G1269S (FIG. 7D) mutants.

Summary

Eighteen different mutants were recovered in the crizotinib screen. Eight mutants were common to both Compound 1 and crizotinib. Eight were unique for crizotinib.

For crizotinib, resistant mutations were identified at concentrations up to 1440 nM, which inhibited >90% parental Ba/F3 cell proliferation. The most frequently occurring mutations all conferred certain degree of resistance with IC50s of 311-1419 nM in the viability assay. Three mutations conferred strongest resistance: L1196M (gate keeper), S1206R, and G1269S. The results from in vitro experiments were indistinguishable from parental Ba/F3 in cell viability assays (711-1141 nM). In vivo results provided that crizotinib was completely inefficacious in xenograph mouse model, even at a dosing of 200 mg/kg. Other mutations (I1171T, F1174C, G1210K and F1245C) resulted in in vitro IC50 values of 315-478 nM.

For Compound 1, ten mutants were recovered in the screen. Two mutants (G1202S and D1203) were unique for Compound 1. These mutants were rare and only appeared at low concentrations. Four mutations overlapped with ALK mutations detected in neuroblastoma patients: T1151, I1171, F1174, and F1245.

Compound 1 was able to overcome all mutations that confer resistance to crizotinib, ASP3026 or CH542802. Compound 1 completely suppressed the emergence of resistance at 1000 nM, and only one mutation (S1206R) recovered at 500 nM. Compound 1 also remained active against three mutants that conferred complete resistance to crizotinib. The results from in vitro experiments provided IC50s ranging from 23-269 nM in cell viability assays, accompanied by inhibition of ALK phosphorylation. In vitro data for L1196M and G1269S included IC50 values of 45 nM and 16 nM. For other mutations (I1171T, F1174C, G1210K and F1245C), in vitro IC50 values were <70 nM. For S1206R, potent in vitro (IC50: 194 nM) and in vivo (75 mg/kg) activity was observed against mutant that confers greatest resistance to Compound 1.

Pharmacokinetic/pharmacodynamic data revealed that Compound 1 sustained p-ALK inhibition (80-90% for L1196M and G1269S, 40-60% for S1206R) for 24 hrs after single dose of 50 mg/kg. In vivo results provided complete tumor regression at 50 and 75 mg/kg dosing of Compound 1 for the L1196M and G1269S mutants, and tumor growth inhibition at 75 mg/kg for the S1206R mutant.

The crizotinib screen was extended using CH5424802 and ASP-3026 to identify additional mutations, including among others amino acid substitutions for S1136, T1151, I1268, I1171, F1174, V1180, L1196, S1206, F1245, I1268, and G1269. Specific mutations identified included among others, I1171N, I1171S, I1171T, G1269C, G1269S, L1196M, F1174{C, I, V and L}, and others. As described above, compounds of Formula I, and in particular, Compound 1, retain potency against the various mutant ALK proteins, even in cases of profound resistance of the mutant to crizotinib, CH5424802 or ASP-3026.

Conclusion

Based on the results disclosed herein, and the validation of crizotinib-resistant mutations in the clinical setting, a reasonable prediction is that resistance will arise in the clinic based on its modest potency, narrow therapeutic window (or therapeutic index), and reported clinical achievable plasma level (median $C_{trough}$:~225 ng/ml at MTD). In contrast, Compound 1 appears to be a more robust ALK inhibitor, may to provide a more complete clinical response and may suppress the emergence of resistance more effectively than inhibitors of wild-type ALK such as crizotinib, CH5424802 or ASP-3026.

Example 4

Inhibition of Crizotinib-Resistant Tumors with Compound 1 In Vivo

Figure 11A:
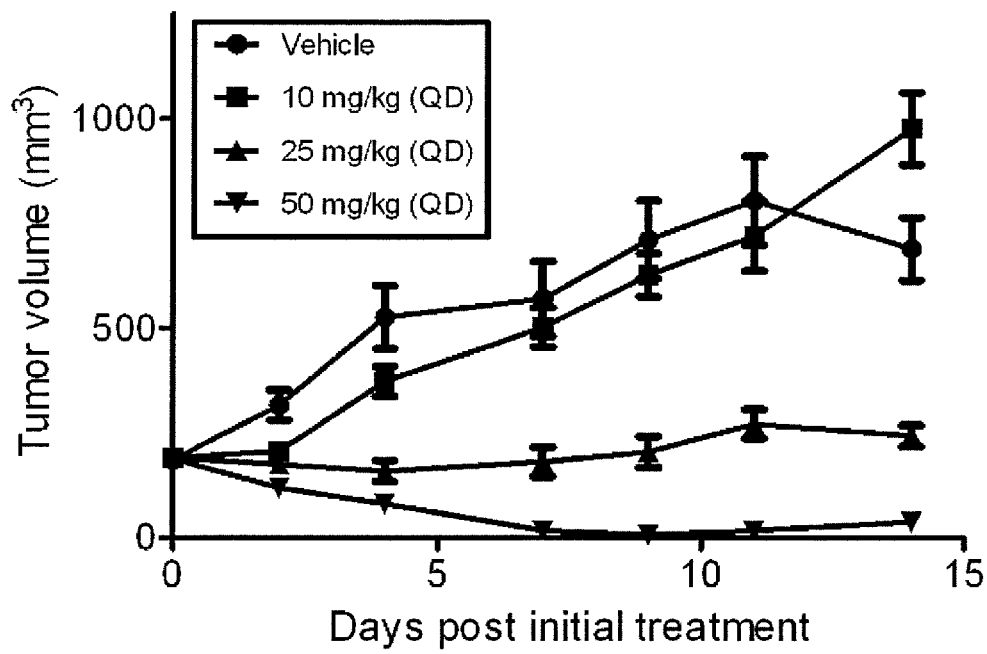
FIGS. 11A and 11B are graphs depicting the efficacy of compound 1 (FIG. 11A) and crizotinib (FIG. 11B) to L1196M mutant-driven tumors in a xenograft model. The tumors respond to treatment with compound 1, but crizotinib has no effect.
Figure 11B:
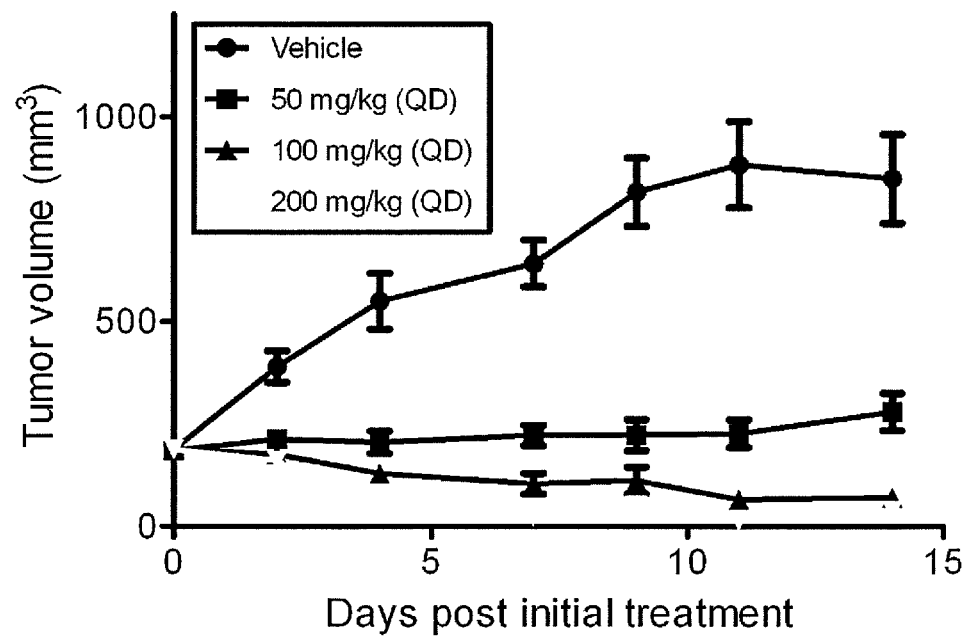

Xenograft models were also used to determine efficacy of compound 1 against crizotinib-resistant tumors (L1196M mutant-driven tumors). The results are depicted in FIG. 11A (showing response to therapy with compound 1) and 11B (showing no response to therapy with crizotinib).

Tumor growth regression was observed in animals treated with compound 1.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for treating an ALK-driven cancer in a subject comprising the steps of:
   a) providing a subject having an ALK-driven cancer characterized by the presence of a mutation in anaplastic lymphoma kinase (ALK), wherein said mutation is selected from mutations corresponding to the amino acid positions in SEQ ID NO: 2 for: (i) a substitution for isoleucine to threonine at amino acid position 1171; (ii) a substitution for phenylalanine to cysteine at amino acid position 1174; (iii) a substitution for leucine to methionine at amino acid position 1196; (iv) a substitution for serine with arginine at amino acid position 1206; (v) a substitution for glutamic acid to lysine at amino acid position 1210; (vi) a substitution for phenylalanine to cysteine at amino acid position 1245; (vii) a substitution for glycine to serine at amino acid position 1269; and (viii) a substitution for valine to leucine at amino acid position 1180; and b) administering to said subject a therapeutically effective amount of compound of formula (I), or a pharmaceutically acceptable salt thereof:

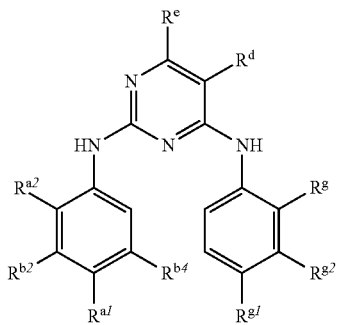

(I)

wherein
$R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two or three heteroatoms, independently selected from N, S and O, wherein the 5- or 6-membered ring is substituted by $R^h$;

$R^h$ is H, $C_{1-4}$ alkyl, or halo;

$R^{a2}$ is H, $C_{1-6}$ alkoxy, $C_{3-6}$ alkenyloxy, or $C_{3-6}$ cycloalkyloxy;

$R^g$ is —P(O)($R^{3A}$)($R^{3B}$);

each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;

$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;

$R^{g1}$ is H, F, or a 5 or 6 member heterocyclic ring comprising 1 or 2 N atoms, the heterocyclic ring being unsubstituted or substituted;

$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy,
—OC(O)N($R^{5A}$)($R^{5B}$), —$NR^{5C}$C(O)$OR^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

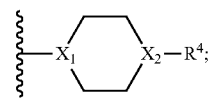

each Y is, independently, a bond, —O—, —S— or —$NR^1$—;

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl.

2. The method of claim 1, wherein said ALK is full-length ALK.

3. The method of claim 1, wherein said ALK is an ALK-fusion product.

4. A method for treating an ALK-driven cancer expressing an ALK-fusion protein in a subject comprising the steps of:

a) providing a subject having an ALK-driven cancer characterized by the presence of a mutation in said ALK-fusion protein, wherein said mutation is selected from mutations corresponding to the amino acid positions in SEQ ID NO: 2 for: (i) a substitution for phenylalanine with valine at amino acid position 1174; and (ii) a substitution for tyrosine with serine at amino acid position 1278; and b) administering to said subject a therapeutically effective amount of compound of formula (I), or a pharmaceutically acceptable salt thereof:

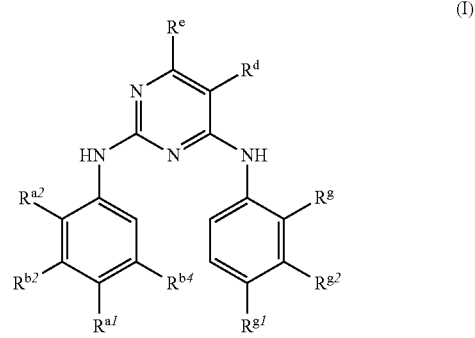

(I)

wherein
$R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two, or three heteroatoms, independently selected from N, S and O, wherein the 5- or
6-membered ring is substituted by $R^h$;
$R^h$ is H, $C_{1-4}$ alkyl, or halo;
$R^{a2}$ is H, $C_{1-6}$ alkoxy, $C_{3-6}$ alkenyloxy, or $C_{3-6}$ cycloalkyloxy;
$R^g$ is —P(O)($R^{3A}$)($R^{3B}$);
each of $R^{3A}$ and $R^{3B}$, is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;
$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;
$R^{g1}$ is H, F, or a 5 or 6 member heterocyclic ring comprising 1 or 2 N atoms, the heterocyclic ring being unsubstituted or substituted;
$R^{b2}$ is H, F, or is a 5 or 6 member heterocyclic ring containing 1, 2 or 3 N or O atoms, the heterocyclic ring being unsubstituted or substituted;
$R^{b4}$ halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy,
—OC(O)N($R^{5A}$)($R^{5B}$), —NR$^{5C}$C(O)OR$^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;
each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;
$R^{a1}$ combines with $R^{b4}$ to form a 6 member heterocyclic ring, or is H, halo, —CN, —NO$_2$, —R$^1$, —OR$^2$, —O—NR$^1$R$^2$, —NR$^1$R$^2$, —NR$^1$—NR$^1$R$^2$, —NR$^1$—OR$^2$, —C(O)YR$^2$, —OC(O)YR$^2$, —NR$^1$C(O)YR$^2$, —SC(O)YR$^2$, —NR$^1$C(=S)YR$^2$, —OC(=S)YR$^2$, —C(=S)YR$^2$, —YC(=NR$^1$)YR$^2$, —YC(=N—OR$^1$)YR$^2$, —YC(=N—NR$^1$R$^2$)YR$^2$, —YP(=O)(YR$^1$)(YR$^2$), —NR$^1$SO$_2$R$^2$, —S(O)$_x$R$^2$, —SO$_2$NR$^1$R$^2$, —NR$^1$SO$_2$NR$^1$R$^2$, or

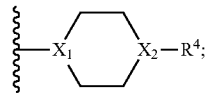

each Y is, independently, a bond, —O—, —S— or —NR$^1$—;
each occurrence of R$^1$ and R$^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and
$R^4$ is selected from alkyl, alkenyl, alkynyl, cycloalkyl, cycloalkenyl, cycloalkynyl, aryl, heteroalkyl, heterocyclic and heteroaryl.

5. A method of inhibiting the proliferation of a cell expressing an ALK mutant, wherein said ALK mutant is characterized by the presence of a mutation in anaplastic lymphoma kinase (ALK) selected from mutations corresponding to the amino acid positions in SEQ ID NO: 2 for: (i) a substitution for threonine to lysine at amino acid position 1151; (ii) a substitution for leucine to valine at amino acid position 1152; (iii) a substitution for cysteine to tyrosine at amino acid position 1156; (iv) a substitution for isoleucine with serine at amino acid position 1171; and (v) a substitution for glycine to cysteine, serine, or alanine at amino acid position 1269,
said method comprising contacting said cell with a compound of formula (I), or a pharmaceutically acceptable salt thereof:

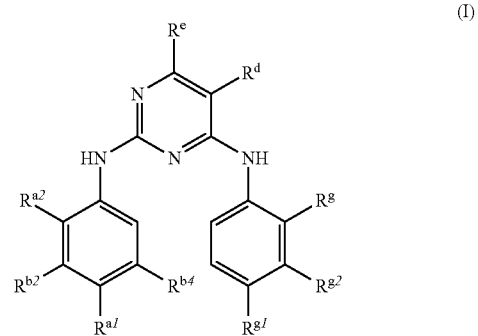

wherein
$R^d$ is H, $C_{1-4}$ alkyl, or halo; and $R^e$ is H; or $R^d$ and $R^e$, together with the pyrimidine ring atoms to which they are attached, form a 5- or 6-membered ring containing one or two heteroatoms, independently selected from N, S and O, wherein the 5- or 6-membered ring is substituted by $R^h$;
$R^h$ is H, $C_{1-4}$ alkyl, or halo;
$R^{a2}$ is H, $C_{1-6}$ alkoxy, $C_{3-6}$ alkenyloxy, or $C_{3-6}$ cycloalkyloxy;
$R^g$ is —P(O)($R^{3A}$)($R^{3B}$);
each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;
$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;
$R^{g1}$ is H, F, or a 5 or 6 member heterocyclic ring comprising 1 or 2 N atoms, the heterocyclic ring being unsubstituted or substituted;
$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy, —OC(O)N($R^{5A}$)($R^{5B}$), —$NR^{5C}$C(O)$OR^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

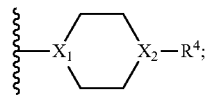

each Y is, independently, a bond, —O—, —S— or —$NR^1$—;

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl, in an amount sufficient to inhibit said proliferation.

6. A method of inhibiting the proliferation of a cell expressing a mutant ALK-fusion protein, wherein said mutant ALK-fusion protein is characterized by the presence of a mutation in said ALK-fusion protein selected from mutations corresponding to the amino acid positions in SEQ ID NO: 2 for: (i) a substitution for phenylalanine with valine at amino acid position 1174; and (ii) a substitution for tyrosine with serine at amino acid position 1278, said method comprising contacting said cell with a compound of formula (I), or a pharmaceutically acceptable salt thereof:

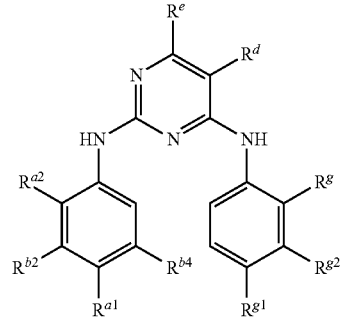

(I)

wherein $R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two, or three heteroatoms, independently selected from N, S and O, wherein the 5- or 6-membered ring is substituted by $R^h$;

$R^h$ is H, $C_{1-4}$ alkyl, or halo;

$R^{a2}$ is H, $C_{1-6}$ alkoxy, $C_{3-6}$ alkenyloxy, or $C_{3-6}$ cycloalkyloxy;

$R^g$ is —P(O)($R^{3A}$)($R^{3B}$);

each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;

$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;

$R^{g1}$ is H, F, or a 5 or 6 member heterocyclic ring comprising 1 or 2 N atoms, the heterocyclic ring being unsubstituted or substituted;

$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy, —OC(O)N($R^{5A}$)($R^{5B}$), —$NR^{5C}$C(O)$OR^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC (=S)YR², —C(=S)YR², —YC(=NR¹)YR², —YC(=N—OR¹)YR², —YC(=N—NR¹R²)YR², —YP(=O)(YR¹)(YR²), —NR¹SO₂R², —S(O)ᵣR², —SO₂NR¹R², —NR¹SO₂NR¹R², or

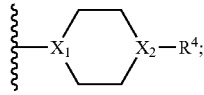

each Y is, independently, a bond, —O—, —S— or —NR¹—;
each occurrence of R¹ and R² is, independently, selected from H, alkyl, alkenyl, alkynyl, cycloalkyl, cycloalkenyl, cycloalkynyl, aryl, heteroalkyl, heterocyclic and heteroaryl;
each of X₁ and X₂ is, independently, selected from CH and N; and
R⁴ is selected from alkyl, alkenyl, alkynyl, cycloalkyl, cycloalkenyl, cycloalkynyl, aryl, heteroalkyl, heterocyclic and heteroaryl,
in an amount sufficient to inhibit said proliferation.

7. A method of treating an ALK-driven cancer refractory to one or more of crizotinib, CH5424802 and ASP3026 in a subject, said method comprising administering to said subject a compound of formula I:

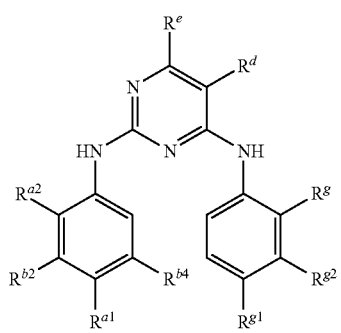

wherein
R$^d$ is H, C₁₋₄ alkyl, or halo; and R$^e$ is H; or R$^d$ and R$^e$, together with the pyrimidine ring atoms to which they are attached, form a 5- or 6-membered ring containing one, two, or three heteroatoms, independently selected from N, S and O, wherein the 5- or 6-membered ring is substituted by R$^h$;
R$^h$ is H, C₁₋₄ alkyl, or halo;
R$^{a2}$ is H, C₁₋₆ alkoxy, C₃₋₆ alkenyloxy, or C₃₋₆ cycloalkyloxy;
R$^g$ is —P(O)(R$^{3A}$)(R$^{3B}$);
each of R$^{3A}$ and R$^{3B}$ is, independently, selected from H, alkyl, alkenyl, alkynyl, cycloalkyl, cycloalkenyl, cycloalkynyl, and heteroalkyl, or R$^{3A}$ and R$^{3B}$, together with the atoms to which they are attached, combine to form a 5- or 6-membered heterocyclic ring which is unsubstituted or substituted;
R$^{g2}$ is H, halo, CN, alkyl, alkenyl, alkynyl, cycloalkyl, cycloalkenyl, cycloalkynyl, heteroalkyl, or, R$^{g2}$ and R$^g$ together with the atoms to which they are attached form a 5- to 7-member heterocyclic ring comprising 1-3 hetero atoms independently selected from P, N, O and S, the heterocyclic ring being unsubstituted or substituted;

R$^{g1}$ is H, F, or a 5 or 6 member heterocyclic ring comprising 1 or 2 N atoms, the heterocyclic ring being unsubstituted or substituted;
R$^{b2}$ is H, F, or is a 5 or 6 member heterocyclic ring containing 1, 2 or 3 N or O atoms, the heterocyclic ring being unsubstituted or substituted;
R$^{b4}$ is H, halo, CN, alkyl, alkenyl, alkynyl, cycloalkyl, cycloalkenyl, cycloalkynyl, heteroalkyl, C₁₋₆ alkoxy, C₃₋₆ alkenyloxy, or C₃₋₆ cycloalkyloxy, —OC(O)N(R$^{5A}$)(R$^{5B}$), —NR$^{5C}$C(O)OR$^{5D}$; a 5 or 6 member heterocyclic ring comprising 1, 2 or 3 N or O atoms, the heterocyclic ring being unsubstituted or substituted, or, R$^{b4}$ and R$^{a1}$ together with the atoms to which they are attached form a 6 member heterocyclic ring comprising 1, 2 or 3 N or O atoms which is unsubstituted or substituted;
each of R$^{5A}$, R$^{5B}$, R$^{5C}$, and R$^{5D}$ is, independently, selected from H, alkyl, alkenyl, alkynyl, and heteroalkyl, or R$^{5A}$ and R$^{5B}$, together with the atoms to which they are attached, combine to form a 5- or 6-membered heterocyclic ring which is unsubstituted or substituted;
R$^{a1}$ combines with R$^{b4}$ to form a 6 member heterocyclic ring, or is H, halo, —CN, —NO₂, —R¹, —OR², —O—NR¹R², —NR¹R², —NR¹—NR¹R², —NR¹—OR², —C(O)YR², —OC(O)YR², —NR¹C(O)YR², —SC(O)YR², —NR¹C(=S)YR², —OC(=S)YR², —C(=S)YR², —YC(=NR¹)YR², —YC(=N—OR¹)YR², —YC(=N—NR¹R²)YR², —YP(=O)(YR¹)(YR²), —NR¹SO₂R², —S(O)ᵣR², —SO₂NR¹R², —NR¹SO₂NR¹R², or

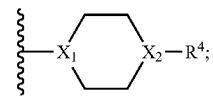

each Y is, independently, a bond, —O—, —S— or —NR¹—;
each occurrence of R¹ and R² is, independently, selected from H, alkyl, alkenyl, alkynyl, cycloalkyl, cycloalkenyl, cycloalkynyl, aryl, heteroalkyl, heterocyclic and heteroaryl;
each of X₁ and X₂ is, independently, selected from CH and N; and
R⁴ is selected from alkyl, alkenyl, alkynyl, cycloalkyl, cycloalkenyl, cycloalkynyl, aryl, heteroalkyl, heterocyclic and heteroaryl,
or a pharmaceutically acceptable salt thereof, in an amount sufficient to treat said cancer, and wherein the term CH5424802 refers to the compound,

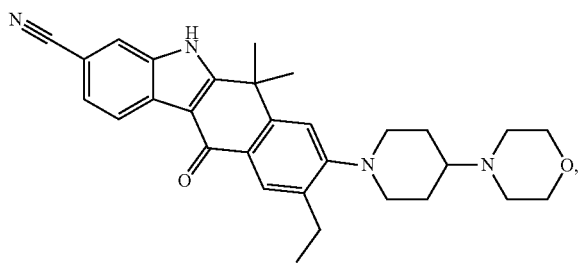 [SMILES: CCc1cc2c(cc1N1CCC(N3CCOCC3)CC1)C(C)(C)c1[nH]c3cc(C#N)ccc3c1C2=O]

and the term ASP3026 refers to the compound,

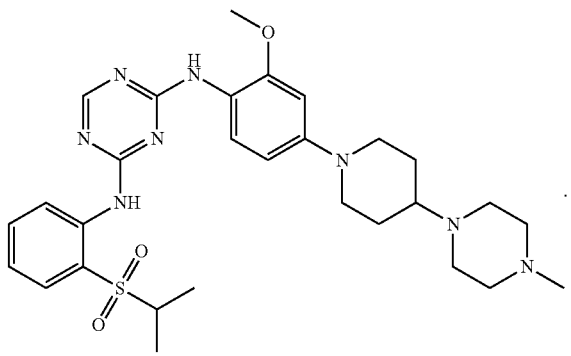 [SMILES: COc1cc(N2CCC(N3CCN(C)CC3)CC2)ccc1Nc1ncnc(Nc2ccccc2S(=O)(=O)C(C)C)n1]

8. A method of treating an ALK-driven cancer in a subject intolerant to one or more of crizotinib, CH5424802 and ASP3026, said method comprising administering to said subject a compound of formula I:

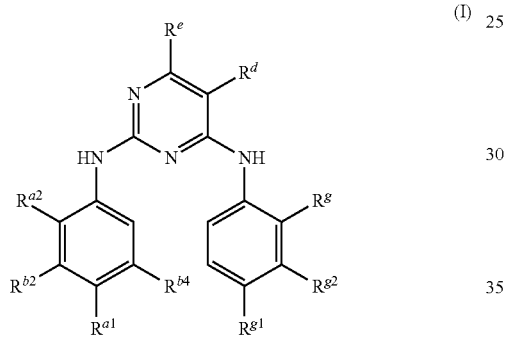

wherein $R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two, or three heteroatoms, independently selected from N, S and O, wherein the 5- or 6-membered ring is substituted by $R^h$;

$R^h$ is H, $C_{1-4}$ alkyl, or halo;

$R^{a2}$ is H, $C_{1-6}$ alkoxy, $C_{3-6}$ alkenyloxy, or $C_{3-6}$ cycloalkyloxy;

$R^g$ is $-P(O)(R^{3A})(R^{3B})$;

each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;

$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;

$R^{g1}$ is H, F, or a 5 or 6 member heterocyclic ring comprising 1 or 2 N atoms, the heterocyclic ring being unsubstituted or substituted;

$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy, $-OC(O)N(R^{5A})(R^{5B})$, $-NR^{5C}C(O)OR^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, $-CN$, $-NO_2$, $-R^1$, $-OR^2$, $-O-NR^1R^2$, $-NR^1R^2$, $-NR^1-NR^1R^2$, $-NR^1-OR^2$, $-C(O)YR^2$, $-OC(O)YR^2$, $-NR^1C(O)YR^2$, $-SC(O)YR^2$, $-NR^1C(=S)YR^2$, $-OC(=S)YR^2$, $-C(=S)YR^2$, $-YC(=NR^1)YR^2$, $-YC(=N-OR^1)YR^2$, $-YC(=N-NR^1R^2)YR^2$, $-YP(=O)(YR^1)(YR^2)$, $-NR^1SO_2R^2$, $-S(O)_rR^2$, $-SO_2NR^1R^2$, $-NR^1SO_2NR^1R^2$, or

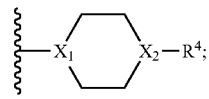

each Y is, independently, a bond, $-O-$, $-S-$ or $-NR^1-$;

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl, or a pharmaceutically acceptable salt thereof, in an amount sufficient to treat said cancer, and wherein the term CH5424802 refers to the compound,

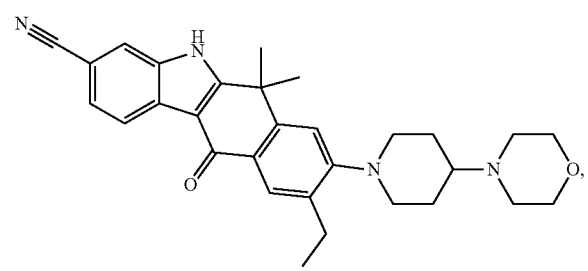 [SMILES: CCc1cc2c(cc1N1CCC(N3CCOCC3)CC1)C(C)(C)c1[nH]c3cc(C#N)ccc3c1C2=O]

and the term ASP3026 refers to the compound,

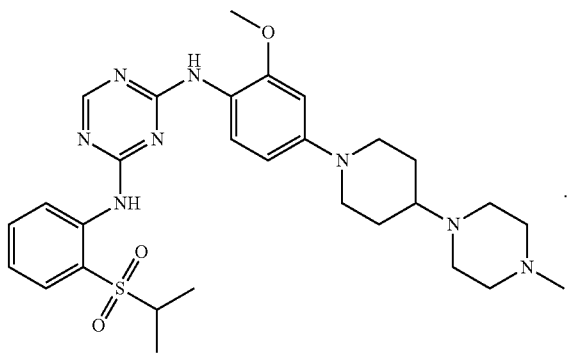 [SMILES: COc1cc(N2CCC(N3CCN(C)CC3)CC2)ccc1Nc1ncnc(Nc2ccccc2S(=O)(=O)C(C)C)n1]

9. A method of treating an ALK-driven cancer refractory to an inhibitor of wild-type ALK in a subject, said method comprising administering to said subject a compound of formula I:

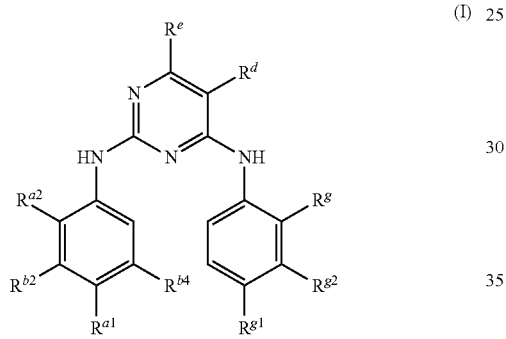

(I)

wherein $R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two, or three heteroatoms, independently selected from N, S and O, wherein the 5- or 6-membered ring is substituted by $R^h$;

$R^h$ is H, $C_{1-4}$ alkyl, or halo;

$R^{a2}$ is H, $C_{1-6}$ alkoxy, $C_{3-6}$ alkenyloxy, or $C_{3-6}$ cycloalkyloxy;

$R^g$ is —P(O)($R^{3A}$)($R^{3B}$);

each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;

$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;

$R^{g1}$ is H, F, or a 5 or 6 member heterocyclic ring comprising 1 or 2 N atoms, the heterocyclic ring being unsubstituted or substituted;

$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy, —OC(O)N($R^{5A}$)($R^{5B}$), —$NR^{5C}$C(O)O$R^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, —CN, —$NO_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

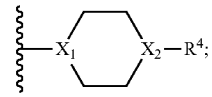

each Y is, independently, a bond, —O—, —S— or —$NR^1$—;

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl, or a pharmaceutically acceptable salt thereof, in an amount sufficient to treat said cancer.

10. A method for treating an ALK-driven cancer in a subject comprising the steps of (a) providing a subject having an ALK-driven cancer characterized by the presence of a mutation in anaplastic lymphoma kinase (ALK), and (b) administering to said subject a therapeutically effective amount of compound 1, having the following structure,

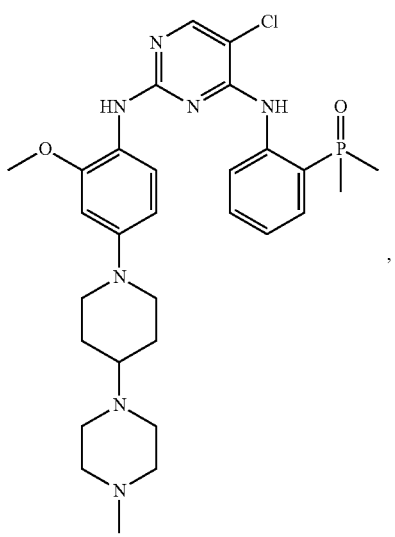

or a pharmaceutically acceptable salt thereof.

11. The method of claim 10, wherein said ALK is full-length ALK.

12. The method of claim 10, wherein said ALK is an ALK-fusion product.

13. The method of claim 10, wherein said mutation is selected from mutations corresponding to the amino acid positions in SEQ ID NO: 2 for:
(i) a substitution for threonine at amino acid position 1151; (ii) a substitution for leucine at amino acid position 1152; (iii) a substitution for cysteine at amino acid position 1156; (iv) a substitution for isoleucine at amino acid position 1171; (v) a substitution for phenylalanine at amino acid position 1174; (vi) a substitution for valine at amino acid position 1180; (vii) a substitution for arginine at amino acid position 1181; (viii) a substitution for leucine at amino acid position 1196; (ix) a substitution for leucine at amino acid position 1198; (x) a substitution for glycine at amino acid position 1202; (xi) a substitution for aspartic acid at amino acid position 1203; (xii) a substitution for serine at amino acid position 1206; (xiii) a substitution for glutamic acid at amino acid position 1210; (xiv) a substitution for glutamic acid at amino acid position 1241; (xv) a substitution for phenylalanine at amino acid position 1245; (xvi) a substitution for isoleucine at amino acid position 1268; (xvii) a substitution for glycine at amino acid position 1269; and (xviii) insertion of an amino acid following amino acid position 1151.

14. The method of claim 13, wherein said mutation is selected from mutations corresponding to the amino acid positions in SEQ ID NO: 2 for: (i) a substitution for leucine to arginine at amino acid position 1152; (ii) a substitution for cysteine to tyrosine at amino acid position 1156; (iii) a substitution for isoleucine to serine at amino acid position 1171; (iv) a substitution for isoleucine to asparagine at amino acid position 1171; (v) a substitution for isoleucine to threonine at amino acid position 1171; (vi) a substitution for phenylalanine to leucine at amino acid position 1174; (vii) a substitution for phenylalanine to cysteine at amino acid position 1174; (viii) a substitution for valine to leucine at amino acid position 1180; (ix) a substitution for leucine to methionine at amino acid position 1196; (x) a substitution for glycine to arginine at amino acid position 1202; (xi) a substitution for aspartic acid to asparagine at amino acid position 1203; (xii) a substitution for serine to tyrosine at amino acid position 1206; (xiii) a substitution for serine with arginine at amino acid position 1206; (xiv) a substitution for glutamic acid to lysine at amino acid position 1210; (xv) a substitution for phenylalanine to cysteine at amino acid position 1245; (xvi) a substitution for glycine to alanine at amino acid position 1269; (xvii) a substitution for glycine to serine at amino acid position 1269; and (xviii) insertion of threonine following position 1151.

15. A method for treating an ALK-driven cancer in a subject comprising the steps of:
a) providing a subject having an ALK-driven cancer characterized by the presence of a mutation in anaplastic lymphoma kinase (ALK), wherein said mutation is selected from mutations corresponding to the amino acid positions in SEQ ID NO: 2 for: ((i) a substitution for leucine to arginine at amino acid position 1152; (ii) a substitution for cysteine to tyrosine at amino acid position 1156; (iii) a substitution for isoleucine to serine at amino acid position 1171; (iv) a substitution for isoleucine to asparagine at amino acid position 1171; (v) a substitution for isoleucine to threonine at amino acid position 1171; (vi) a substitution for phenylalanine to leucine at amino acid position 1174; (vii) a substitution for phenylalanine to cysteine at amino acid position 1174; (viii) a substitution for valine to leucine at amino acid position 1180; (ix) a substitution for leucine to methionine at amino acid position 1196; (x) a substitution for aspartic acid to asparagine at amino acid position 1203; (xi) a substitution for serine with arginine at amino acid position 1206; (xii) a substitution for glutamic acid to lysine at amino acid position 1210; (xiii) a substitution for phenylalanine to cysteine at amino acid position 1245; (xiv) a substitution for glycine to alanine at amino acid position 1269; and (xv) a substitution for glycine to serine at amino acid position 1269; and
b) administering to said subject a therapeutically effective amount of compound of formula (I), or a pharmaceutically acceptable salt thereof:

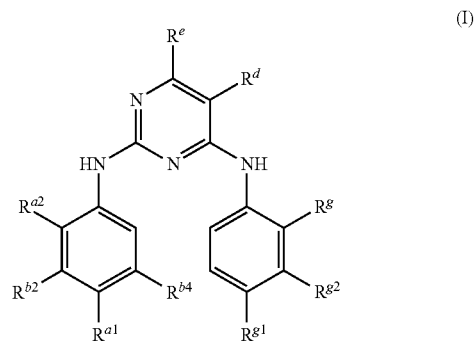

(I)

wherein $R^d$ is H, $C_{1-4}$ alkyl, or halo; and $R^e$ is H; or $R^d$ and $R^e$, together with the pyrimidine ring atoms to which they are attached, form a 5- or 6-membered ring containing one, two or three heteroatoms, independently selected from N, S and O, wherein the 5- or 6-membered ring is substituted by $R^h$;

$R^h$ is H, $C_{1-4}$ alkyl, or halo;

$R^{a2}$ is H, $C_{1-6}$ alkoxy, $C_{3-6}$ alkenyloxy, or $C_{3-6}$ cycloalkyloxy;

$R^g$ is —P(O)($R^{3A}$)($R^{3B}$);

each of $R^{3A}$ and $R^{3B}$ is, independently, selected from H, alkyl, alkenyl, alkynyl, cycloalkyl, cycloalkenyl, cycloalkynyl, and heteroalkyl, or $R^{3A}$ and $R^{3B}$, together with the atoms to which they are attached, combine to form a 5- or 6-membered heterocyclic ring which is unsubstituted or substituted;

$R^{g2}$ is H, halo, CN, alkyl, alkenyl, alkynyl, cycloalkyl, cycloalkenyl, cycloalkynyl, heteroalkyl, or, $R^{g2}$ and $R^g$ together with the atoms to which they are attached form a 5- to 7-member heterocyclic ring comprising 1-3 hetero atoms independently selected from P, N, O and S, the heterocyclic ring being unsubstituted or substituted;

$R^{g1}$ is H, F, or a 5 or 6 member heterocyclic ring comprising 1 or 2 N atoms, the heterocyclic ring being unsubstituted or substituted;

$R^{b2}$ is H, F, or is a 5 or 6 member heterocyclic ring containing 1, 2 or 3 N or O atoms, the heterocyclic ring being unsubstituted or substituted;

$R^{b4}$ is H, halo, CN, alkyl, alkenyl, alkynyl, cycloalkyl, cycloalkenyl, cycloalkynyl, heteroalkyl, $C_{1-6}$ alkoxy, $C_{3-6}$ alkenyloxy, or $C_{3-6}$ cycloalkyloxy, —OC(O)N($R^{5A}$)($R^{5B}$), —$NR^{5C}$C(O)O$R^{5D}$; a 5 or 6 member heterocyclic ring comprising 1, 2 or 3 N or O atoms, the heterocyclic ring being unsubstituted or substituted, or, $R^{b4}$ and $R^{a1}$ together with the atoms to which they are attached form a 6 member heterocyclic ring comprising 1, 2 or 3 N or O atoms which is unsubstituted or substituted;

each of $R^{5A}$, $R^{5B}$, $R^{5C}$, and $R^{5D}$ is, independently, selected from H, alkyl, alkenyl, alkynyl, and heteroalkyl, or $R^{5A}$ and $R^{5B}$, together with the atoms to which they are attached, combine to form a 5- or 6-membered heterocyclic ring which is unsubstituted or substituted;

$R^{a1}$ combines with $R^{b4}$ to form a 6 member heterocyclic ring, or is H, halo, —CN, —NO$_2$, —$R^1$, —$OR^2$, —O—$NR^1R^2$, —$NR^1R^2$, —$NR^1$—$NR^1R^2$, —$NR^1$—$OR^2$, —C(O)$YR^2$, —OC(O)$YR^2$, —$NR^1$C(O)$YR^2$, —SC(O)$YR^2$, —$NR^1$C(=S)$YR^2$, —OC(=S)$YR^2$, —C(=S)$YR^2$, —YC(=$NR^1$)$YR^2$, —YC(=N—$OR^1$)$YR^2$, —YC(=N—$NR^1R^2$)$YR^2$, —YP(=O)($YR^1$)($YR^2$), —$NR^1SO_2R^2$, —S(O)$_rR^2$, —$SO_2NR^1R^2$, —$NR^1SO_2NR^1R^2$, or

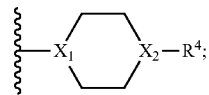

each Y is, independently, a bond, —O—, —S— or —$NR^1$—;

each occurrence of $R^1$ and $R^2$ is, independently, selected from H, alkyl, alkenyl, alkynyl, cycloalkyl, cycloalkenyl, cycloalkynyl, aryl, heteroalkyl, heterocyclic and heteroaryl;

each of $X_1$ and $X_2$ is, independently, selected from CH and N; and $R^4$ is selected from alkyl, alkenyl, alkynyl, cycloalkyl, cycloalkenyl, cycloalkynyl, aryl, heteroalkyl, heterocyclic and heteroaryl.

16. The method of claim 15, wherein said ALK is full-length ALK.

17. The method of claim 15, wherein said ALK is an ALK-fusion product.

* * * * *